US012618853B2

(12) United States Patent
Tousi

(10) Patent No.: US 12,618,853 B2
(45) Date of Patent: May 5, 2026

(54) METHODS FOR ANALYZING CHAIN MISPAIRING IN MULTISPECIFIC BINDING PROTEINS

(71) Applicant: Sanofi, Paris (FR)

(72) Inventor: Fatemeh Tousi, Dedham, MA (US)

(73) Assignee: Sanofi, Paris (FR)

( * ) Notice: Subject to any disclaimer, the term of this patent is extended or adjusted under 35 U.S.C. 154(b) by 836 days.

(21) Appl. No.: 16/889,404

(22) Filed: Jun. 1, 2020

(65) Prior Publication Data

US 2021/0123926 A1 Apr. 29, 2021

Related U.S. Application Data

(60) Provisional application No. 62/926,313, filed on Oct. 25, 2019.

(30) Foreign Application Priority Data

May 28, 2020 (EP) .................................... 20315271

(51) Int. Cl.
*G01N 33/68* (2006.01)
*C07K 16/00* (2006.01)
(Continued)

(52) U.S. Cl.
CPC ......... *G01N 33/6854* (2013.01); *C07K 16/00* (2013.01); *C12P 21/02* (2013.01);
(Continued)

(58) Field of Classification Search
CPC ........... G01N 33/6854; G01N 33/5005; G01N 33/6848; G01N 2030/027; C07K 16/00;
(Continued)

(56) References Cited

U.S. PATENT DOCUMENTS 10,626,169 B2 4/2020 Beil et al.
10,882,922 B2 1/2021 Yang
(Continued)

FOREIGN PATENT DOCUMENTS

WO 2012061558 A2 5/2012
WO 2012135345 A1 10/2012
(Continued)

OTHER PUBLICATIONS

Vandenheede et al., "Denaturing and Native Size-Exclusion Chromatography Coupled to High-Resolution Mass Spectrometry for Detailed Characterization of Monoclonal Antibodies and Antibody-Drug Conjugates," LCGC Europe, vol. 32(6), pp. 304-311, published Jun. 1, 2019. (Year: 2019).*
(Continued)

*Primary Examiner* — Shafiqul Haq
*Assistant Examiner* — Nam P Nguyen
(74) *Attorney, Agent, or Firm* — MORRISON & FOERSTER LLP

(57) ABSTRACT

Provided herein are methods for monitoring production of a multispecific binding protein and one or more mispaired species by a cell line, as well as methods of production and screening related thereto. In some embodiments, the methods comprise detecting an amount (e.g., a relative amount) of a multispecific binding protein and one or more mispaired species in a cell culture medium by size-exclusion ultra-performance liquid chromatography and mass spectrometry (SE-UPLC-MS). In some embodiments, the multispecific binding protein is a multispecific antibody, antibody fragment, or Fc fusion protein.

18 Claims, 31 Drawing Sheets

Specification includes a Sequence Listing.

Heavy chain mis-pairing          Light chain mis-pairing

(51) Int. Cl.

| | |
|---|---|
| *C12P 21/02* | (2006.01) |
| *G01N 30/02* | (2006.01) |
| *G01N 33/50* | (2006.01) |
| *B01D 15/34* | (2006.01) |
| *B01D 15/38* | (2006.01) |

(52) U.S. Cl.
CPC ......... *G01N 33/5005* (2013.01); *B01D 15/34* (2013.01); *B01D 15/3809* (2013.01); *C07K 2317/31* (2013.01)

(58) Field of Classification Search
CPC ..... C07K 2317/31; C12P 21/02; B01D 15/34; B01D 15/3809
See application file for complete search history.

(56) References Cited

U.S. PATENT DOCUMENTS

| | | |
|---|---|---|
| 11,129,905 B2 | 9/2021 | Yang et al. |
| 11,186,649 B2 | 11/2021 | Wu et al. |
| 11,192,960 B2 | 12/2021 | Yang et al. |
| 11,254,737 B2 | 2/2022 | Beil et al. |
| 11,365,261 B2 | 6/2022 | Cameron et al. |
| 11,530,268 B2 | 12/2022 | Wu et al. |
| 11,613,576 B2 | 3/2023 | Beil et al. |
| 11,779,651 B2 | 10/2023 | Yang et al. |
| 11,932,704 B2 | 3/2024 | Yang |
| 12,227,573 B2 | 2/2025 | Beil et al. |
| 2015/0315296 A1 | 11/2015 | Schaefer |
| 2017/0320967 A1 | 11/2017 | Yang |
| 2018/0237511 A1 | 8/2018 | Beil |
| 2019/0054182 A1 | 2/2019 | Yang |
| 2019/0106504 A1 | 4/2019 | Wu |
| 2020/0054765 A1 | 2/2020 | Yang |
| 2020/0140552 A1 | 5/2020 | Wu |
| 2020/0317761 A1 | 10/2020 | Beil et al. |
| 2020/0399369 A1 | 12/2020 | Asokan |
| 2021/0061925 A1 | 3/2021 | Yang et al. |
| 2022/0041746 A1 | 2/2022 | Cameron et al. |
| 2022/0119553 A1 | 4/2022 | Yang et al. |
| 2022/0226495 A1 | 7/2022 | Yang et al. |
| 2022/0275102 A1 | 9/2022 | Cameron et al. |
| 2023/0220079 A1 | 7/2023 | Beil et al. |
| 2024/0279362 A1 | 8/2024 | Yang |
| 2025/0250337 A1 | 8/2025 | Beil et al. |
| 2025/0250338 A1 | 8/2025 | Beil et al. |
| 2025/0312475 A1 | 10/2025 | Yang et al. |

FOREIGN PATENT DOCUMENTS

| | | | |
|---|---|---|---|
| WO | 2017074878 A1 | 5/2017 | |
| WO | 2017180913 A2 | 10/2017 | |
| WO | 2018151841 A1 | 8/2018 | |
| WO | WO-2019060718 A1 * | 3/2019 | ........... A61K 39/395 |
| WO | 2019074973 A2 | 4/2019 | |
| WO | 2020076853 A1 | 4/2020 | |
| WO | 2020210386 A1 | 10/2020 | |
| WO | 2020210392 A1 | 10/2020 | |
| WO | 2021080649 A1 | 4/2021 | |

OTHER PUBLICATIONS

Tousi et al., "Intact Protein Mass Spectrometry of Cell Culture Harvest Guides Cell Line Development for Trispecific Antibodies", Anal. Chem. 2020, vol. 92, pp. 2764-2769 (Year: 2020).*

U.S. Appl. No. 18/054,734, Wu et al., filed Nov. 11, 2022.

Baeuerle, P.A. et al. (Jun. 15, 2009, e-pub. Jun. 9, 2009). "Review—Bispecific T-Cell Engaging Antibodies for Cancer Therapy," Cancer Res. 69(12):4941-4944.

Chothia, C. et al. (Aug. 20, 1987). "Canonical Structures for the Hypervariable Regions of Immunoglobulins," J. Mol. Biol. 196(4):901-917.

Chothia, C. et al. (Dec. 21/28, 1989). "Conformations of Immunoglobulin Hypervariable Regions," Nature 342 (6252):877-883.

Chusainow, J. et al. (Mar. 1, 2009, e-pub. Oct. 8, 2008). "A study of Monoclonal Antibody-Producing CHO Cell Lines: What Makes A Stable High Producer?" Biotechnology And Bioengineering 102(4):1182-1196.

Correnti, C.E. et al. (May 2018, e-pub. Jan. 31, 2018). "Simultaneous Multiple Interaction T-Cell Engaging (SMITE) Bispecific Antibodies Overcome Bispecific T-Cell Engager (Bite) Resistance Via CD28 Co-Stimulation," Leukemia 32(5):1239-1243.

Graf, T. et al. (Dec. 1, 2018). "Development of a Multi-Product SE-UHPLC Method for the Determination of Size-Variants in Bispecific Antibody Formats", LCGC North America 36(12):870-879, 12 pages.

Haberger, M. et al. (2016, e-pub. Jan. 28, 2016). "Rapid Characterization of Biotherapeutic Proteins by Size-Exclusion Chromatography Coupled to Native Mass Spectrometry," MAbs 8(2):331-339.

International Search Report and Written Opinion of the Searching Authority mailed on Sep. 14, 2020, for Patent Application No. PCT/US2020/035587, filed Jun. 1, 2020, 16 pages.

Kitazawa, T. et al. (Oct. 2012, e-pub. Sep. 30, 2012). "A Bispecific Antibody to Factors IXa and X Restores Factor VIII Hemostatic Activity In a Hemophilia A Model," Nature Medicine 18(10):1570-1574.

Krah, S. et al. (Oct. 2017, e-pub. Jan. 27, 2017). "Engineering Bispecific Antibodies With Defined Chain Pairing," New Biotechnology 39:167-173.

Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.

MacCallum, R.M. et al. (1996). "Antibody-Antigen Interactions: Contact Analysis and Binding Site Topography," J. Mol. Biol. 262:732-745.

Martin, A.C.R. (2010). "Protein Sequence and Structure Analysis of Antibody Variable Domains," Chapter 3 In Antibody Engineering, vol. 2. Kontermann R., Dübel S., eds. Springer-Verlag, Berlin, pp. 33-51.

Masui, S. et al. (Mar. 1, 2005). "An Efficient System to Establish Multiple Embryonic Stem Cell Lines Carrying an Inducible Expression Unit," Nucleic Acids Res. 33(4):e43, pp. 1-8.

Niwa, H. et al. (Dec. 1991). "Efficient Selection for High-Expression Transfectants with a Novel Eukaryotic Vector," Gene. 108(2):193-199.

Padlan, E.A. et al. (Jun. 2017). "Identification of Specificity-Determining Residues in Antibodies," FASEB J. 9 (1):133-139.

Ridgway, J.B.B. et al. (1996). "'Knobs-into-holes' Engineering of Antibody CH3 Domains for Heavy Chain Heterodimerization," Protein Eng. 9(7):617-621.

Schachner, L. et al. (Nov. 21, 2016). "Characterization of Chain Pairing Variants of Bispecific IgG Expressed in a Single Host Cell By High Resolution Native and Denaturing Mass Spectrometry," Anal Chem. 88 (24):12122-12127.

Schaefer, W. et al. (Jan. 2016, e-pub. Dec. 9, 2015). "Heavy and Light Chain Pairing of Bivalent Quadroma and Knobs-Into-Holes Antibodies Analyzed by UHR-ESI-QTOF Mass Spectrometry," MABS 8(1):49-55.

Spiess, C. et al. (Sep. 13, 2013). "Development of a Human IgG4 Bispecific Antibody for Dual Targeting of Interleukin-4 (IL-4) and Interleukin-13 (IL-13) Cytokines," The Journal of Biological Chemistry 288(37):26583-26593.

Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," Nucleic Acids Res. 22(22):4673-4680.

Tousi, F. et al. (2019). "Intact Protein Mass Spectrometry Guiding Cell Line Development for Tri-specific Antibodies," Poster presented at 67th ASMS Conference on Mass Spectrometry & Allied Topics, Framingham, MA, Jun. 2-6, 2019, 18 pages.

Tousi, F. et al. (2020, e-pub. Jan. 15, 2020). "Intact Protein Mass Spectrometry of Cell Culture Harvest Guides Cell Line Development for Trispecific Antibodies," Anal Chem. 92(3):2764-2769, 8 pages.

(56) References Cited

OTHER PUBLICATIONS

U.S. Appl. No. 17/515,227, Yang et al., filed Oct. 29, 2021.

U.S. Appl. No. 17/737,814, filed May 5, 2022, for Dabdoubi et al.

Wang, C. et al. (Sep. 2018). "A Systematic Approach for Analysis and Characterization of Mispairing in Bispecific Antibodies With Asymmetric Architecture," MABS 10(8):1226-1235.

Woods, R.J. et al. (September/Oct. 2013, e-pub. Jun. 24, 2013). "LC-MS Characterization and Purity Assessment of a Prototype Bispecific Antibody," mAbs 5(5):711-722.

Xu, L. et al. (Oct. 6, 2017; e-pub. Sep. 20, 2017). "Trispecific Broadly Neutralizing HIV Antibodies Mediate Potent SHIV Protection in Macaques," Science 358(6359):85-90, 17 pages.

Yin, Y. et al. (2016, e-pub. Nov. 1, 2016). "Precise Quantification of Mixtures of Bispecific IgG Produced in Single Host Cells by Liquid Chromatography-Orbitrap High-Resolution Mass Spectrometry," MAbs 8(8):1467-1476.

U.S. Appl. No. 18/183,107, Beil et al., filed Mar. 13, 2023.

U.S. Appl. No. 18/433,295, Yang et al., filed Feb. 5, 2024.

U.S. Appl. No. 18/458,060, filed Aug. 29, 2023, for Yang et al.

U.S. Appl. No. 19/012,409, Beil et al., filed Jan. 7, 2025.

U.S. Appl. No. 18/960,890, filed Nov. 26, 2024, for Yang et al.

U.S. Appl. No. 19/012,367, Beil et al., filed Jan. 7, 2025.

* cited by examiner

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Gly Gly Gly Ser Gly Gly Gly Gly Ser
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Gly Gly Gly Gly Ser Gly Gly Gly Gly Ser Gly Gly Gly Gly Ser
1               5                   10                  15

<210> SEQ ID NO 3
```

-continued

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Thr Lys Gly Pro Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Gly Gln Pro Lys Ala Ala Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Gly Ser Gly Ser Ser Gly Ser Gly Gly
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Asp Lys Thr His Thr
1               5
```

METHODS FOR ANALYZING CHAIN MISPAIRING IN MULTISPECIFIC BINDING PROTEINS

CROSS REFERENCE TO RELATED APPLICATIONS

This application claims priority to U.S. Provisional Application No. 62/926,313, filed Oct. 25, 2019, and EP Application No. EP20315271.5, filed May 28, 2020, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952032800SEQLIST.TXT, date recorded: May 29, 2020, size: 2 KB).

FIELD

The disclosure relates to methods for monitoring production of a multispecific binding protein and one or more mispaired species by a host cell, as well as methods of production and screening related thereto. The disclosure further relates to methods for monitoring production of an antibody or antibody derivative and one or more weight variant species by a host cell, as well as methods of production and screening related thereto.

BACKGROUND

Multi-specific antibodies that bind two or more different epitopes on the same or different antigens have become attractive therapeutic options in immune-oncology in recent years (Baeuerle, P. A. & Reinhardt, C., *Cancer Res* 2009, 69 (12), 4941-4). Multi-targeting has been used for different purposes, such as achieving enhanced drug specificity or mimicking natural ligands in signaling pathways, for example in hemophilia treatments through simultaneous binding to receptor pairs on the surface of the same cell (Kitazawa, T. et al. *Nat Med* 2012, 18 (10), 1570-4). A prominent application is the T-cell engager (TCE) concept where one arm of the molecule activates T-cells via CD3/ CD28 receptor binding and the other arm targets a tumor antigen for tumor killing (Krah, S. et al. *N Biotechnol* 2017, 39 (Pt B), 167-173; Correnti, C. E. et al. *Leukemia* 2018, 32 (5), 1239-1243).

IgG-like tri-specific antibodies (tsAb) are comprised of two different heavy chains and two different light chains, commonly expressed in a single host cell followed by intracellular chain assembly. While this method of production eliminates the need to have two separate cell lines and purification processes, it can generate unwanted mispaired species in addition to the desired tsAb. In the absence of rational design and with random association of the subunits, the theoretical yield of the correctly paired species is only 12.5% (FIG. 1B). Forced heterodimerization of the heavy chains has been successfully accomplished through protein engineering approaches such as the knobs-into-holes design (Ridgway, J. B. et al. *Protein Eng* 1996, 9 (7), 617-21). However, cognate pairing of the light chains to the correct heavy chains remains a significant challenge in tsAb production.

As such, there remains a need for methods for monitoring or analyzing production of a multispecific binding protein and one or more mispaired species. In addition, there remains a need for methods for monitoring or analyzing production of antibody or antibody derivatives that comprise multiple species varying in molecular weight (e.g., with different chemical modifications, such as chemically modified cysteine or other residues, or with different glycoforms).

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

To meet these and other needs, provided herein are methods for monitoring production of a multispecific binding protein and one or more mispaired species (e.g., by a cell line). These methods provide, inter alia, a high throughput analytical platform based on denaturing SEC-LC-Intact MS for identification and relative quantitation of chain mispairing and other IgG-related species. Advantageously, these methods allow for intact MS analysis of mAb-related species (e.g., multispecific binding proteins, antibodies, Fc fusion proteins, antibody fragments, and so forth) directly from a clarified cell harvest, bypassing time consuming and expensive purification (e.g., protein A affinity chromatography) and buffer exchange steps. As such, these methods can be used to rapidly screen a large number of clones for potential production cell lines.

In some embodiments, provided herein are methods for monitoring production of a multispecific binding protein and one or more mispaired species, the methods comprising: detecting, by size-exclusion ultra-performance liquid chromatography and mass spectrometry (SE-UPLC-MS), an amount of a multispecific binding protein and one or more mispaired species in a cell culture medium comprising the multispecific binding protein and the one or more mispaired species. In some embodiments, the multispecific binding protein comprises an association of two or more polypeptide chains comprising at least a first polypeptide chain and a second polypeptide chain different from the first polypeptide chain, and the one or more mispaired species comprise two or more polypeptide chains comprising at least one of the first and second polypeptide chains in an association other than that of the multispecific binding protein.

In some embodiments, the multispecific binding protein is a multispecific antibody comprising a first antibody heavy chain, a first antibody light chain, a second antibody heavy chain different from the first antibody heavy chain, and a second antibody light chain different from the first antibody light chain. In some embodiments, the multispecific binding protein is a bispecific antibody, antibody fragment, or Fc fusion protein. In some embodiments, the multispecific binding protein is a trispecific antibody, antibody fragment, or Fc fusion protein. In some embodiments, the one or more mispaired species comprises one or more of: an association of four polypeptide chains of the multispecific antibody that comprises two of the first antibody heavy chains; an association of four polypeptide chains of the multispecific antibody that comprises two of the second antibody heavy chains; an association of four polypeptide chains of the multispecific antibody that comprises two of the first antibody light chains; and an association of four polypeptide chains of the multispecific antibody that comprises two of the second antibody light chains. In some embodiments, the multispecific binding protein comprises four polypeptide chains that form the three antigen binding sites, wherein a first polypeptide chain of the binding protein comprises a structure represented by the formula:

$$V_{L2}\text{-}L_1\text{-}V_{L1}\text{-}L_2\text{-}C_L \qquad [I]$$

and a second polypeptide chain of the binding protein comprises a structure represented by the formula:

$$V_{H1}\text{-}L_3\text{-}V_{H2}\text{-}L_4\text{-}C_{H1}\text{-hinge-}C_{H2}\text{---}C_{H3} \qquad [II]$$

and a third polypeptide chain of the binding protein comprises a structure represented by the formula:

$$V_{H3}\text{---}C_{H1}\text{-hinge-}C_{H2}\text{---}C_{H3} \qquad [III]$$

and a fourth polypeptide chain of the binding protein comprises a structure represented by the formula:

$$V_{L3}\text{---}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair, wherein $V_{H1}$ and $V_{L1}$ form a first antigen binding site, wherein $V_{H2}$ and $V_{L2}$ form a second antigen binding site, and wherein $V_{H3}$ and $V_{L3}$ form a third antigen binding site. In some embodiments, the one or more mispaired species comprise one or more of: an association of four polypeptide chains of the binding protein that comprises two polypeptide chains according to formula I; an association of four polypeptide chains of the binding protein that comprises two polypeptide chains according to formula II; an association of four polypeptide chains of the binding protein that comprises two polypeptide chains according to formula III; and an association of four polypeptide chains of the binding protein that comprises two polypeptide chains according to formula IV.

In some embodiments, detecting the amount of the multispecific binding protein and the one or more mispaired species comprises deconvoluting one or more MS spectra obtained by the MS. In some embodiments, a relative amount of the multispecific binding protein as compared to the one or more mispaired species is detected. In some embodiments, a relative amount of the multispecific binding protein as compared to an amount of one or more individual mispaired species is detected. In some embodiments, a relative amount of the multispecific binding protein as compared to an overall amount of mispaired species is detected. In some embodiments, the methods further comprise, prior to detection, providing or obtaining (e.g., from a cell line that produces the multispecific binding protein and one or more mispaired species) a cell culture medium comprising the multispecific binding protein and one or more mispaired species. In some embodiments, the methods further comprise, prior to detection, separating the cell culture medium from a cell line that produces the multispecific binding protein and one or more mispaired species. In some embodiments, prior to detection, the cell culture medium is separated from the cell line by centrifugation. In some embodiments, the cell culture medium is subjected to SE-UPLC without a prior chromatographic separation. In some embodiments, the cell culture medium is subjected to SE-UPLC without prior protein A affinity chromatography. In some embodiments, the MS is intact MS. In some embodiments, the MS is quadrupole time-of-flight (QToF) MS. In some embodiments, the SE-UPLC is denaturing SE-UPLC. In some embodiments, the SE-UPLC is directly coupled to the MS. In some embodiments, the methods further comprise, prior to SE-UPLC-MS, contacting the multispecific binding protein and one or more mispaired species with a protease. In some embodiments, the protease is IdeS or IdeZ. In some embodiments, SE-UPLC is performed with an initial flow rate of less than about 0.4 mL/min. In some embodiments, SE-UPLC is performed with an initial flow rate of about 0.1 mL/min. In some embodiments, SE-UPLC is performed with a flow rate of about 0.1 mL/min for the first 25 minutes, followed by a flow rate of about 0.4 mL/min (e.g., for minutes 25-33). In some embodiments, SE-UPLC is performed using isocratic elution with a mobile phase. In some embodiments, the mobile phase comprises a solution comprising 30:70 acetonitrile:water. In some embodiments, the mobile phase comprises formic acid and trifluoroacetic acid (TFA). In some embodiments, the mobile phase comprises about 0.05% formic acid and about 0.05% trifluoroacetic acid (TFA). In some embodiments, detecting the amount of the multispecific binding protein and one or more mispaired species is accomplished in about 33 minutes or less. In some embodiments, In some embodiments, the method is accomplished in about 33 minutes or less. In some embodiments, the MS is capable of resolving a mass difference of about 300 Da between the multispecific binding protein and the one or more mispaired species, or between two mispaired species. In some embodiments, the MS is capable of resolving a mass difference of about 162 Da between the multispecific binding protein or mispaired species and one of more glycoforms.

In some embodiments, the cell line is a mammalian cell line. In some embodiments, the cell line is a Chinese hamster ovary (CHO) cell line. In some embodiments, prior to detection, the cell line is cultured with the cell culture medium in a continuous cell culture, e.g., in a stirred tank bioreactor. In some embodiments, prior to detection, the cell line is cultured with the cell culture medium in a batch cell culture.

In some embodiments, provided herein are methods for producing a multispecific binding protein, the methods comprising: (a) culturing a cell line comprising one or more polynucleotides encoding the multispecific binding protein in a cell culture medium under conditions suitable for production of the multispecific binding protein and one or more mispaired species by the cell line; (b) separating, from the cell line, the cell culture medium comprising the multispecific binding protein and one or more mispaired species;

(c) detecting an amount of the multispecific binding protein and one or more mispaired species in the cell culture medium by size-exclusion ultra-performance liquid chromatography and mass spectrometry (SE-UPLC-MS); and (d) removing at least a portion of one or more of the mispaired species from the multispecific binding protein produced by the cell line, or determining one or both of quality and purity of the multispecific binding protein produced by the cell line. In some embodiments, the multispecific binding protein comprises an association of two or more polypeptide chains comprising at least a first polypeptide chain and a second polypeptide chain different from the first polypeptide chain. In some embodiments, the one or more mispaired species comprise two or more polypeptide chains comprising at least one of the first and second polypeptide chains in an association other than that of the multispecific binding protein.

In some embodiments, the multispecific binding protein is a multispecific antibody comprising a first antibody heavy chain, a first antibody light chain, a second antibody heavy chain different from the first antibody heavy chain, and a second antibody light chain different from the first antibody light chain. In some embodiments, the multispecific binding protein is a bispecific antibody or Fc fusion protein. In some embodiments, the multispecific binding protein is a trispecific antibody or Fc fusion protein. In some embodiments, the one or more mispaired species comprises one or more of: an association of four polypeptide chains of the multispecific antibody that comprises two of the first antibody heavy chains; an association of four polypeptide chains of the multispecific antibody that comprises two of the second antibody heavy chains; an association of four polypeptide chains of the multispecific antibody that comprises two of the first antibody light chains; and an association of four polypeptide chains of the multispecific antibody that comprises two of the second antibody light chains. In some embodiments, the multispecific binding protein comprises four polypeptide chains that form the three antigen binding sites, wherein a first polypeptide chain of the binding protein comprises a structure represented by the formula:

$$V_{L2}\text{-}L_1\text{-}V_{L1}\text{-}L_2\text{-}C_L \qquad [I]$$

and a second polypeptide chain of the binding protein comprises a structure represented by the formula:

$$V_{H1}\text{-}L_3\text{-}V_{H2}\text{-}L_4\text{-}C_{H1}\text{-hinge-}C_{H2}\text{---}C_{H3} \qquad [II]$$

and a third polypeptide chain of the binding protein comprises a structure represented by the formula:

$$V_{H3}\text{---}C_{H1}\text{-hinge-}C_{H2}\text{---}C_{H3} \qquad [III]$$

and a fourth polypeptide chain of the binding protein comprises a structure represented by the formula:

$$V_{L3}\text{---}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair, wherein $V_{H1}$ and $V_{L1}$ form a first antigen binding site, wherein $V_{H2}$ and $V_{L2}$ form a second antigen binding site, and wherein $V_{H3}$ and $V_{L3}$ form a third antigen binding site. In some embodiments, the one or more mispaired species comprise one or more of: an association of four polypeptide chains of the binding protein that comprises two polypeptide chains according to formula I; an association of four polypeptide chains of the binding protein that comprises two polypeptide chains according to formula II; an association of four polypeptide chains of the binding protein that comprises two polypeptide chains according to formula III; and an association of four polypeptide chains of the binding protein that comprises two polypeptide chains according to formula IV.

In some embodiments, detecting the amount of the multispecific binding protein and one or more mispaired species comprises deconvoluting one or more MS spectra obtained by MS. In some embodiments, detecting the multispecific binding protein and one or more mispaired species comprises assessing overall titer of the multispecific binding protein produced by the cell line. In some embodiments, detecting the multispecific binding protein and one or more mispaired species comprises assessing overall titer of the mispaired species produced by the cell line. In some embodiments, a relative amount of the multispecific binding protein as compared to the one or more mispaired species is detected. In some embodiments, a relative amount of the multispecific binding protein as compared to an amount of one or more individual mispaired species is detected. In some embodiments, a relative amount of the multispecific binding protein as compared to an overall amount of mispaired species is detected. In some embodiments, the cell culture medium is separated from the cell line by centrifugation. In some embodiments, the cell culture medium is subjected to SE-UPLC in (c) without a prior chromatographic separation. In some embodiments, the cell culture medium is subjected to SE-UPLC in (c) without prior protein A affinity chromatography. In some embodiments, the MS is intact MS. In some embodiments, the MS is quadrupole time-of-flight (QToF) MS. In some embodiments, the SE-UPLC is denaturing SE-UPLC. In some embodiments, the SE-UPLC is directly coupled to the MS. In some embodiments, the methods further comprise, after culturing the cell line and prior to detection, contacting the multispecific binding protein and one or more mispaired species with a protease. In some embodiments, the protease is IdeS or IdeZ. In some embodiments, SE-UPLC is performed with an initial flow rate of less than about 0.4 mL/min. In some embodiments, SE-UPLC is performed with an initial flow rate of about 0.1 mL/min. In some embodiments, SE-UPLC is performed with a flow rate of about 0.1 mL/min for the first 25 minutes, followed by a flow rate of about 0.4 mL/min. In some embodiments, SE-UPLC is performed using isocratic elution with a mobile phase. In some embodiments, the mobile phase comprises a solution comprising 30:70 acetonitrile:water. In some embodiments, the mobile phase comprises formic acid and trifluoroacetic acid (TFA). In some embodiments, the mobile phase comprises about 0.05% formic acid and about 0.05% trifluoroacetic acid (TFA). In some embodiments, detection is accomplished in about 33 minutes or less. In some embodiments, the method is accomplished in about 33 minutes or less. In some embodiments, the MS is capable of resolving a mass difference of about 300 Da between the multispecific binding protein and the one or more mispaired species, or between two mispaired species. In some embodiments, the MS is capable of resolving a mass difference of about 162 Da between the multispecific binding protein or mispaired species and one of more glycoforms.

In some embodiments, the cell line is a mammalian cell line. In some embodiments, the cell line is a Chinese hamster ovary (CHO) cell line. In some embodiments, the cell line is cultured in a continuous cell culture (e.g., in a stirred tank bioreactor). In some embodiments, the cell line is cultured in a batch cell culture.

In some embodiments, provided herein are methods for screening a plurality of cell lines for production of a multispecific binding protein, the methods comprising: detecting an amount of a multispecific binding protein produced by a first cell line of the plurality according to the method of any one of the above embodiments; and detecting an amount of the multispecific binding protein produced by a second cell line of the plurality according to the method of any one of the above embodiments.

In some embodiments, the methods further comprise: comparing the amount of multispecific binding protein produced by the first cell line with the amount of multispecific binding protein produced by the second cell line; and based on the comparison, selecting the cell line that produced the higher amount of the multispecific binding protein. In some embodiments, the methods further comprise: detecting an amount of one or more mispaired species produced by the first cell line according to the method of any one of the above embodiments; and detecting an amount of one or more mispaired species produced by the second cell line according to the method of any one of the above embodiments. In some embodiments, the methods further comprise: after detecting the amount of one or more mispaired species produced by the first and second cell lines: comparing the amount of the one or more mispaired species produced by the first cell line with the amount of the one or more mispaired species produced by the second cell line; and based on the comparison, selecting the cell line that produced the higher ratio of multispecific binding protein to one or more mispaired species. In some embodiments, the cell line is selected based on a higher ratio of multispecific binding protein to the amount of one or more individual mispaired species. In some embodiments, the cell line is selected based on a higher ratio of multispecific binding protein to the overall amount of mispaired species.

In some embodiments, provided herein are methods for monitoring production of an antibody or antibody derivative and one or more weight variant species, the methods comprising: detecting, by size-exclusion ultra-performance liquid chromatography and mass spectrometry (SE-UPLC-MS), an amount of an antibody or antibody derivative and one or more weight variant species in a cell culture medium comprising the antibody or antibody derivative and one or more weight variant species, wherein the antibody or antibody derivative and one or more weight variant species differ in molecular weight. In some embodiments, provided herein are methods for producing an antibody or antibody derivative, the methods comprising: (a) culturing a cell line comprising one or more polynucleotides encoding the an antibody or antibody derivative in a cell culture medium under conditions suitable for production of the antibody or antibody derivative and one or more weight variant species by the cell line; (b) separating, from the cell line, the cell culture medium comprising the antibody or antibody derivative and one or more weight variant species; (c) detecting an amount of the antibody or antibody derivative and one or more weight variant species in the cell culture medium by size-exclusion ultra-performance liquid chromatography and mass spectrometry (SE-UPLC-MS); and (d) removing at least a portion of one or more of the weight variant species from the antibody or antibody derivative produced by the cell line, or determining one or both of quality and purity of the antibody or antibody derivative produced by the cell line.

In some embodiments, provided herein are methods for screening a plurality of cell lines for production of an antibody or antibody derivative, the methods comprising: detecting an amount of an antibody or antibody derivative produced by a first cell line of the plurality according to the method of any one of the above embodiments; and detecting an amount of the antibody or antibody derivative produced by a second cell line of the plurality according to the method of any one of the above embodiments. In some embodiments, the methods further comprise: comparing the amount of antibody or antibody derivative produced by the first cell line with the amount of antibody or antibody derivative produced by the second cell line; and based on the comparison, selecting the cell line that produced the higher amount of the antibody or antibody derivative. In some embodiments, the methods further comprise: detecting an amount of one or more weight variant species produced by the first cell line according to the method of any one of the above embodiments; and detecting an amount of one or more weight variant species produced by the second cell line according to the method of any one of the above embodiments. In some embodiments, the methods further comprise: after detecting the amount of one or more weight variant species produced by the first and second cell lines: comparing the amount of the one or more weight variant species produced by the first cell line with the amount of the one or more weight variant species produced by the second cell line; and based on the comparison, selecting the cell line that produced the higher ratio of antibody or antibody derivative to one or more weight variant species, or selecting the cell line that produced a higher relative proportion of a single weight variant species relative to a total amount of antibody or antibody derivative and one or more weight variant species produced. In some embodiments, the amount of an antibody or antibody derivative and/or one or more weight variant species according to any of the embodiments herein refers to a relative amount (e.g., as compared to one or more other species, or as compared to a total amount of antibody/species produced).

In some embodiments, the antibody or antibody derivative comprises a cysteine residue at position 293 (Cys293). In some embodiments, the antibody or antibody derivative and the one or more weight variant species comprise species with a free cysteine (e.g., not disulfide bonded with another cysteine of the antibody or antibody derivative) that has been cysteinylated, N-acetyl cysteinylated, or glutathionylated. In some embodiments, the antibody or antibody derivative is not N-glycosylated (e.g., in the antibody Fc region). In some embodiments, the antibody or antibody derivative comprises a mutation in the Fc region that reduces or eliminates N-glycosylation. In some embodiments, the antibody or antibody derivative comprises an N300A mutation (EU index). In some embodiments, the antibody or antibody derivative is N-glycosylated (e.g., in the antibody Fc region), and the method further comprises (e.g., prior to SE-UPLC-MS), removing the antibody N-glycosylation. In some embodiments, removing the antibody N-glycosylation comprises treating the antibody with a peptide:N-glycosidase enzyme (e.g., PNGase F). In some embodiments, detecting the amount of the antibody or antibody derivative and one or more weight variant species comprises deconvoluting one or more MS spectra obtained by the MS. In some embodiments, the methods further comprise, prior to detection, providing or obtaining (e.g., from a cell line that produces the antibody or antibody derivative and one or more weight variant species) a cell culture medium comprising the antibody or antibody derivative and one or more weight variant species. In some embodiments, the methods further comprise, prior to detection, separating the cell culture medium from a cell line that produces the antibody or antibody derivative and one or more weight variant species. In some embodiments, prior to detection, the cell culture medium is separated from the cell line by centrifugation. In some embodiments, the cell culture medium is subjected to SE-UPLC without a prior chromatographic separation. In some embodiments, the cell culture medium is subjected to SE-UPLC without prior protein A affinity chromatography. In some embodiments, the MS is intact MS. In some embodiments, the MS is quadrupole time-of-flight (QToF) MS. In some embodiments, the SE-UPLC is denaturing SE-UPLC. In some embodiments, the SE-UPLC is directly coupled to the MS. In some embodiments, the one or more weight variant species represent species of the antibody or antibody derivative comprising a chemically modified cysteine residue. In some embodiments, the antibody or antibody derivative and one or more weight variant species differ in molecular weight by at least 119 Da. In some embodiments, the MS is capable of resolving a mass difference among cysteinylated (119 Da mass shift), N-acetyl cysteinylated (161 Da mass shift), and glutathionylated (305 Da mass shift) species. the antibody or antibody derivative and one or more weight variant species differ in molecular weight by at least 162 Da. In some embodiments, the antibody or antibody derivative is N-glycosylated (e.g., in the antibody Fc region), and the one or more weight variant species represent glycoforms of the antibody or antibody derivative. In some embodiments, the MS is capable of resolving a mass difference of about 162 Da between the antibody or antibody derivative and one of more weight variant species that represent glycoforms of the antibody or antibody derivative. In some embodiments, the antibody or antibody derivative is a multispecific antibody.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 3A shows a ranking of anti-CD38 trispecific binding protein-producing clones by percentage of correct tsAb mass (purity). FIG. 3B shows the productivity of each clone (normalized titer) in the same order as depicted in FIG. 3A (i.e., ranked by purity).

FIG. 4A shows a representative base peak chromatogram for denaturing SEC-intact MS analysis of a tsAb clarified harvest fluid. FIG. 4B shows combined spectra under each chromatographic peak. FIG. 4C shows a zoom-in of deconvoluted mass spectrum for a mixture of anti-CD38 trispecific binding protein and anti-HER2 trispecific binding protein resolving light chain mispaired species from two constructs with Δmass=302 Da.

FIG. 9A) and production of correctly paired product (% correct mass; FIG. 9B) of 50 cell clones producing anti-HIV\CD28\CD3 trispecific grown under batch culture conditions.

FIG. 10A) and in an ambr15 bioreactor (fed-batch condition; FIG. 10B).

FIG. 11A shows identification of Cys293 capping status of species using direct intact MS analysis. This antibody contained an N300A mutation that ablated N-glycosylation of the Fc region. FIG. 11B shows identification of Cys293 capping status using direct intact MS analysis of an antibody treated with PNGase F to remove N-glycans prior to analysis.

DETAILED DESCRIPTION

Figure 1A:
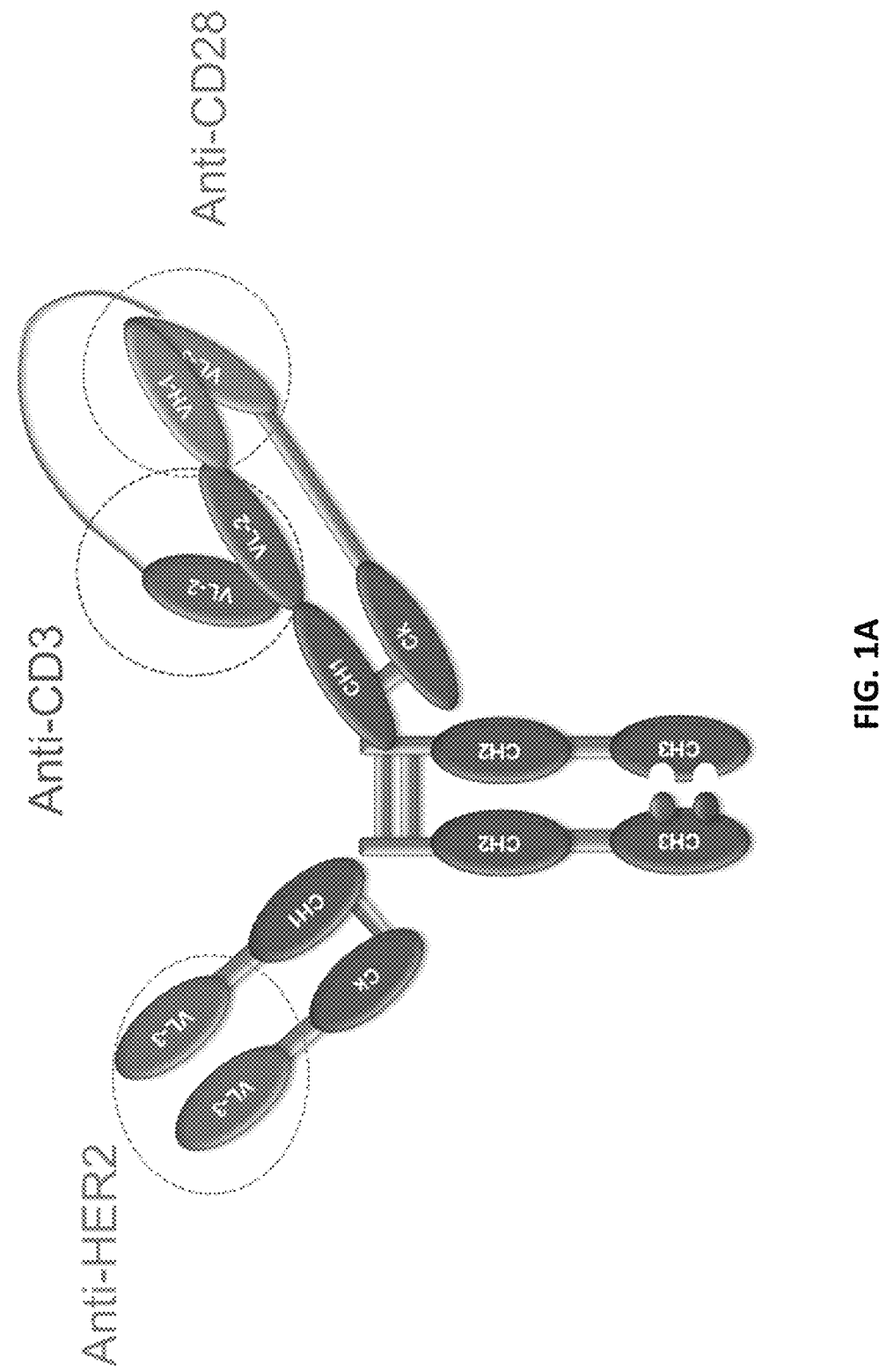
FIG. 1A provides a schematic representation of a trispecific binding protein comprising four polypeptide chains that form three antigen binding sites that bind three target proteins: CD28, CD3, and HER2. A first pair of polypeptides possess dual variable domains having a cross-over orientation (VH1-VH2 and VL2-VL1) forming two antigen binding sites that recognize CD3 and CD28 (CODV), and a second pair of polypeptides possess a single variable domain (VH3 and VL3) forming a single antigen binding site that recognizes HER2 (Fab). The trispecific binding protein shown in FIG. 1A uses a constant region with a "knobs-into-holes" mutation, where the knob is on the second pair of polypeptides with a single variable domain.

The disclosure provides, inter alia, methods for monitoring production of a multispecific binding protein and one or more mispaired species, e.g., a multispecific antibody, antibody fragment, Fc fusion protein, or other multispecific binding protein that comprises an association of two or more polypeptide chains comprising at least a first polypeptide chain and a second polypeptide chain different from the first polypeptide chain, and one or more mispaired species that comprise two or more polypeptide chains comprising at least one of the first and second polypeptide chains in an association other than that of the multispecific binding protein. Similar methods can be applied to production of a multispecific binding protein, screening cell lines for production of a multispecific binding protein, or in the production of antibodies or Fc fusion proteins, as well as production of an antibody or antibody derivative (e.g., produced with one or more weight variant species), or screening cell lines for production of an antibody or antibody derivative (e.g., produced with one or more weight variant species). Advantageously, these methods allow for intact MS analysis of mAb-related species directly in the clarified harvest, bypassing time consuming and expensive purification (e.g., protein A affinity chromatography) and buffer exchange steps. As such, these methods can be used to rapidly screen a large number of clones for potential production cell lines.

The following description sets forth exemplary methods, parameters, and the like. It should be recognized, however, that such description is not intended as a limitation on the scope of the present disclosure but is instead provided as a description of exemplary embodiments.

Definitions

As utilized in accordance with the present disclosure, the following terms, unless otherwise indicated, shall be understood to have the following meanings. Unless otherwise required by context, singular terms shall include pluralities and plural terms shall include the singular.

It is understood that aspects and embodiments of the disclosure described herein include "comprising," "consisting," and "consisting essentially of" aspects and embodiments.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39; MacCallum, 1996, *J. Mol. Biol.* 262(5): 732-45; and Lefranc, 2003, *Dev. Comp. Immunol.* 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," *In Antibody Engineering*, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Acids Res.* 22: 4673-80. Molecular models are conventionally used to correctly delineate framework and CDR regions and thus correct the sequence-based assignments.

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the $V_H$ and $C_{H1}$ domains of one heavy chain, wherein the $V_H$—$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a $F(ab')_2$ molecule.

The term "binding protein" as used herein refers to a non-naturally occurring (or recombinant or engineered) molecule that specifically binds to at least one target antigen. In some embodiments, the binding protein comprises two or more antigen-binding domains. In some embodiments, the binding protein is a multispecific antibody, antibody fragment, or Fc fusion protein. In some embodiments, the binding protein is a bispecific antibody or antibody fragment. In some embodiments, the binding protein is a trispecific antibody or antibody fragment. In some embodiments, the binding protein is a trispecific binding protein, e.g., as described infra. In some embodiments, the binding protein comprises one or two Fc regions fused to one, two, three, or more antigen binding domains or other polypeptides (e.g., an Fc fusion protein). In some embodiments, the binding protein is a dual variable domain (DVD) immunoglobulin, e.g., as described in WO2012061558. In some embodiments, the binding protein comprises dual variable domains having a cross-over orientation, e.g., as described in WO2012135345. In some embodiments, the binding protein comprises four polypeptide chains that form four antigen binding sites, wherein two polypeptide chains have a structure represented by the formula:

$$V_{L1}\text{-}L_1\text{-}V_{L2}\text{-}L_2\text{-}C_L \qquad [I]$$

and two polypeptide chains have a structure represented by the formula:

$$V_{H2}\text{-}L_3\text{-}V_{H1}\text{-}L_4\text{-}C_{H1}\text{-}Fc \qquad [II]$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{R2}$ is a second immunoglobulin heavy chain variable domain;

$C_L$ is an immunoglobulin light chain constant domain;

$C_{H1}$ is the immunoglobulin $C_{H1}$ heavy chain constant domain;

Fc is the immunoglobulin hinge region and $C_{H2}$, $C_{H3}$ immunoglobulin heavy chain constant domains; and $L_1$, $L_2$. $L_3$, and $L_4$ are amino acid linkers; and wherein the polypeptides of formula I and the polypeptides of formula II form a cross-over light chain-heavy chain pair.

A trispecific binding protein of the present disclosure, unless otherwise specified, typically comprises four polypeptide chains that form at least three antigen binding sites, wherein a first polypeptide chain has a structure represented by the formula:

$$V_{L2}\text{-}L_1\text{-}V_{L1}\text{-}L_2\text{-}C_L \qquad [I]$$

and a second polypeptide chain has a structure represented by the formula:

$$V_{H1}\text{-}L_3\text{-}V_{H2}\text{-}L_4\text{-}C_{H1}\text{-hinge-}C_{H2}\text{—}C_{H3} \qquad [II]$$

and a third polypeptide chain has a structure represented by the formula:

$$V_{H3}\text{—}C_{H1} \qquad [III]$$

and a fourth polypeptide chain has a structure represented by the formula:

$$V_{L3}\text{—}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is the immunoglobulin $C_{H1}$ heavy chain constant domain; and hinge is an immunoglobulin hinge region connecting the $C_{H1}$ and $C_{H2}$ domains;

$L_1$, $L_2$, $L_3$ and $L_4$ are amino acid linkers;

and wherein the polypeptide of formula I and the polypeptide of formula II form a cross-over light chain-heavy chain pair.

A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen. A target antigen may have one or more epitopes. With respect to each target antigen recognized by a binding protein, the binding protein is capable of competing with an intact antibody that recognizes the target antigen.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets.

The term "bivalent binding protein" refers to a binding protein that has two binding sites.

The term "trispecific binding protein" refers to a binding protein that specifically binds to three different antigen targets.

The term "trivalent binding protein" refers to a binding protein that has three binding sites. In particular embodiments the trivalent binding protein can bind to one antigen target. In other embodiments, the trivalent binding protein can bind to two antigen targets. In other embodiments, the trivalent binding protein can bind to three antigen targets.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, NJ). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "specifically binds" as used herein refers to the ability of a binding protein or an antigen-binding fragment thereof to bind to an antigen containing an epitope with an Kd of at least about $1 \times 10^{-6}$ M, $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, or more, and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described herein are referred to as $L_1$, which is located on the light chain between the C-terminus of the $V_{L2}$ and the N-terminus of the $V_{L1}$ domain; and $L_2$, which is located on the light chain between the C-terminus of the $V_{L1}$ and the N-terminus of the $C_L$ domain. The heavy chain linkers are known as $L_3$, which is located between the C-terminus of the $V_{H1}$ and the N-terminus of the $V_{H2}$ domain; and $L_4$, which is located between the C-terminus of the $V_{H2}$ and the N-terminus of the $C_{H1}$ domain.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-,α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, α-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:
(1) hydrophobic: Met, Ala, Val, Leu, Ile, Phe, Trp, Tyr, Pro;
(2) polar hydrophilic: Arg, Asn, Asp, Gln, Glu, His, Lys, Ser, Thr;
(3) aliphatic: Ala, Gly, Ile, Leu, Val, Pro;
(4) aliphatic hydrophobic: Ala, Ile, Leu, Val, Pro;
(5) neutral hydrophilic: Cys, Ser, Thr, Asn, Gln;
(6) acidic: Asp, Glu;
(7) basic: His, Lys, Arg;
(8) residues that influence chain orientation: Gly, Pro;
(9) aromatic: His, Trp, Tyr, Phe; and
(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

Methods

Certain aspects of the present disclosure relate to methods for monitoring production of a multispecific binding protein and one or more mispaired species. In some embodiments, the methods comprise detecting an amount of the product (e.g., an antibody, antibody fragment, Fc fusion protein, or multispecific binding protein and one or more mispaired species) by size-exclusion ultra-performance liquid chromatography and mass spectrometry (SE-UPLC-MS). In some embodiments, the product and one or more mispaired species are detected in a cell culture medium. Exemplary and non-limiting descriptions of multispecific binding proteins are provided herein.

Certain aspects of the present disclosure relate to methods for monitoring production of an antibody or antibody derivative and one or more weight variant species. In some embodiments, the methods comprise detecting an amount of the product (e.g., one or more weight variant species of an antibody or antibody derivative) by size-exclusion ultra-performance liquid chromatography and mass spectrometry (SE-UPLC-MS). In some embodiments, the antibody or antibody derivative and one or more weight variant species are detected in a cell culture medium. The antibody or antibody derivative and one or more weight variant species can represent, e.g., multiple species varying in molecular weight (e.g., with different chemical modifications, such as chemically modified cysteine or other residues, or with different glycoforms). As demonstrated in the Examples infra, the methods described herein in reference to analysis of an antibody, antibody fragment, Fc fusion protein, or multispecific binding protein and one or more mispaired species can be applied to analysis of an antibody or antibody derivative and one or more weight variant species.

In some embodiments, the cell culture medium is a clarified cell culture harvest. For example, the cell culture medium may be one that has been harvested from a cell culture and clarified by tangential flow filtration (TFF), depth filtration, and/or centrifugation. In some embodiments, the methods further comprise separating the cell culture medium or harvest from a cell line producing the product (e.g., an antibody, antibody fragment, Fc fusion protein, or multispecific binding protein and one or more mispaired species). In some embodiments, the cell culture medium is clarified by centrifugation. In some embodiments, the cell culture medium is subjected to SE-UPLC without a prior chromatographic separation. That is to say, in some embodiments, the cell culture medium is one that has not been exposed to prior chromatographic separation. In some embodiments, the cell culture medium is subjected to SE-UPLC without prior protein A affinity chromatography. That is to say, in some embodiments, the cell culture medium is one that has not been contacted with protein A.

In some embodiments, detecting the amount of the product (e.g., an antibody, antibody fragment, Fc fusion protein, or multispecific binding protein and one or more mispaired species) comprises deconvoluting one or more MS spectra obtained by the MS. Methods for deconvolution of MS spectra are known in the art. A non-limiting example of software useful for deconvolution is exemplified infra.

In some embodiments, a relative amount of a multispecific binding protein is detected, e.g., as compared to the amount of one or more mispaired species. For example, the amount of a multispecific binding protein produced can be compared to an amount of one or more individual mispaired species, and/or to an overall amount of mispaired species (e.g., an overall amount of all mispaired species, or a certain subset thereof).

In some embodiments, the MS is intact MS. In some embodiments, the MS is quadrupole time-of-flight (QToF) MS. A variety of QToF MS methods are known in the art. Exemplary and non-limiting parameters for QToF MS are described in the Examples infra.

In some embodiments, the MS is capable of resolving a mass difference of about 1000 Da or less, about 900 Da or less, about 800 Da or less, about 700 Da or less, about 600 Da or less, about 500 Da or less, about 400 Da or less, about 300 Da or less, or about 200 Da or less. In some embodiments, the MS is capable of resolving a mass difference of about 300 Da. For example, in some embodiments, the MS is capable of resolving a mass difference of about 300 Da between a multispecific binding protein and one or more mispaired species, or between two mispaired species. In some embodiments, the MS is capable of resolving a mass difference of about 162 Da. For example, in some embodiments, the MS is capable of resolving a mass difference of about 162 Da between glycoforms, e.g., between a multispecific binding protein or mispaired species and one of more glycoforms.

In some embodiments, the SE-UPLC is denaturing SE-UPLC. In some embodiments, the SE-UPLC is directly coupled to the MS. A variety of SE-UPLC methods are known in the art. Exemplary and non-limiting conditions for SE-UPLC are described in the Examples infra.

In some embodiments, SE-UPLC is performed with a slower initial flow rate, followed by a more rapid flow rate. Without wishing to be bound to theory, it is thought that a slower initial flow rate allows for a more efficient size-based separation of cell culture harvest components, while increasing the flow rate after this initial period enhances the overall speed of the method. In some embodiments, SE-UPLC is performed with an initial flow rate of less than about 0.4 mL/min, followed by a flow rate of greater than or equal to about 0.4 mL/min. In some embodiments, the initial flow rate is less than about 0.4 mL/min, less than about 0.3 mL/min, less than about 0.2 mL/min, or about 0.1 mL/min. In some embodiments, the initial flow rate refers to the first 15, 20, or 25 minutes of SE-UPLC. In some embodiments, SE-UPLC is performed with a flow rate of less than about 0.4 mL/min for the first 25 minutes, followed by a flow rate of greater than or equal to about 0.4 mL/min (e.g., from 25-33 minutes). In some embodiments, SE-UPLC is performed with a flow rate of about 0.1 mL/min for the first 25 minutes, followed by a flow rate of about 0.4 mL/min (e.g., from 25-33 minutes).

In some embodiments, SE-UPLC is performed by diverting part(s) of the liquid chromatography (LC) flow with no protein elution (e.g., 0-10 minutes and/or 24-33 minutes) to waste, thereby providing a more rapid analysis for screening and avoiding contamination of the MS source.

In some embodiments, SE-UPLC is performed using isocratic elution with a mobile phase. For example, in some embodiments, the mobile phase comprises a solution comprising 30:70 acetonitrile:water. In some embodiments, the mobile phase comprises formic acid (FA) and trifluoroacetic acid (TFA). Without wishing to be bound to theory, it is thought that, while TFA is useful for liquid chromatography (LC) separation, it can suppress the MS signal, and therefore a mobile phase comprising a mixture of FA and TFA can allow for effective liquid chromatography (LC) separation while maintaining an adequate signal-to-noise ratio for MS analysis. In some embodiments, the mobile phase comprises about 0.05% formic acid and about 0.05% trifluoroacetic acid (TFA).

Advantageously, the methods provided herein allow for rapid analysis of products, thereby enabling high-throughput screening (e.g., of a multitude of potential producer cell lines). For example, in some embodiments, detection is accomplished in about 30 minutes or less, about 33 minutes or less, about 35 minutes or less, about 40 minutes or less, about 45 minutes or less, or about 60 minutes or less.

In some embodiments, the methods further comprise, prior to SE-UPLC-MS, contacting the product (e.g., an antibody, antibody fragment, Fc fusion protein, or multispecific binding protein and one or more mispaired species) with a protease. In some embodiments, the protease is IdeS or IdeZ, e.g., for analysis of antibody fragments.

In some embodiments, the antibody or antibody derivative comprises a cysteine residue at position 293 (Cys293). In some embodiments, the antibody or antibody derivative and the one or more weight variant species comprise species with a free cysteine (e.g., not disulfide bonded with another cysteine of the antibody or antibody derivative) that has been cysteinylated, N-acetyl cysteinylated, or glutathionylated. In some embodiments, the antibody or antibody derivative is not N-glycosylated (e.g., in the antibody Fc region). In some embodiments, the antibody or antibody derivative comprises a mutation in the Fc region that reduces or eliminates N-glycosylation. In some embodiments, the antibody or antibody derivative comprises an N300A mutation (EU index). In some embodiments, the antibody or antibody derivative is N-glycosylated (e.g., in the antibody Fc region), and the method further comprises (e.g., prior to SE-UPLC-MS), removing the antibody N-glycosylation. In some embodiments, removing the antibody N-glycosylation comprises treating the antibody with a peptide:N-glycosidase enzyme (e.g., PNGase F).

In some embodiments, the one or more weight variant species represent species of the antibody or antibody derivative comprising a chemically modified cysteine residue. In some embodiments, the MS is capable of resolving a mass difference among cysteinylated (119 Da mass shift), N-acetyl cysteinylated (161 Da mass shift), and glutathionylated (305 Da mass shift) species. For example, antibodies and antibody derivatives comprising a free cysteine residue (e.g., a cysteine not disulfide bonded to another cysteine residue of the antibody/antibody derivative) and/or antibodies and antibody derivatives comprising an additional cysteine residue engineered into its Fc region can be useful, e.g., for conjugation of a compound (e.g., a cytotoxic drug to form an antibody drug conjugate). This additional cysteine is unpaired (free) i.e. not engaged in disulfide bonds with other cysteines in the mAb molecule. Previous work had shown that this additional cysteine (Cys293) can form unwanted disulfide bonds with nearby cysteine residues, otherwise known as "disulfide bond scrambling," potentially leading to structural instability of the antibody. Uncontrolled sulfhydryl chemistry may also pose significant manufacturability risk during processing to form the ADC leading to undesired drug conjugation profile. To avoid these risks, it is imperative to have the free cysteine capped with disulfide linked modification such as cysteinylation and glutathionylation by adjusting cell culture conditions. These modifications can be selectively reduced to generate a free cysteine prior to the drug conjugation step. The methods described herein can be used, e.g., to analyze production of an antibody or antibody derivative comprising different weight variant species, such as species comprising a chemically modified cysteine like a cysteine capped with disulfide linked modification such as cysteinylation and glutathionylation.

In some embodiments, the antibody or antibody derivative is N-glycosylated (e.g., in the antibody Fc region), and the one or more weight variant species represent glycoforms of the antibody or antibody derivative. In some embodiments, the MS is capable of resolving a mass difference of about 162 Da between the antibody or antibody derivative and one of more weight variant species that represent glycoforms of the antibody or antibody derivative. In some embodiments, the antibody or antibody derivative is a multispecific antibody. In some embodiments, the antibody or antibody derivative is a monoclonal antibody.

Other aspects of the present disclosure relate to methods for producing an antibody, antibody fragment, Fc fusion protein, or multispecific binding protein. In some embodiments, the methods comprise culturing a cell line comprising one or more polynucleotides encoding the product (e.g., an antibody, antibody fragment, Fc fusion protein, or multispecific binding protein and one or more mispaired species) under conditions suitable for production of the product by a cell line; separating, from the cell line, a cell culture medium comprising the product (e.g., an antibody, antibody fragment, Fc fusion protein, or multispecific binding protein and one or more mispaired species); detecting an amount of the product (e.g., an antibody, antibody fragment, Fc fusion protein, or multispecific binding protein and one or more mispaired species) in the cell culture medium by size-exclusion ultra-performance liquid chromatography and mass spectrometry (SE-UPLC-MS); and (d) removing at least a portion of one or more of the mispaired species from the multispecific binding protein produced by the cell line. In some embodiments, the methods comprise culturing a cell line comprising one or more polynucleotides encoding the product (e.g., an antibody, antibody fragment, Fc fusion protein, or multispecific binding protein and one or more mispaired species) under conditions suitable for production of the product by a cell line; separating, from the cell line, a cell culture medium comprising the product (e.g., an antibody, antibody fragment, Fc fusion protein, or multispecific binding protein and one or more mispaired species); detecting an amount of the product (e.g., an antibody, antibody fragment, Fc fusion protein, or multispecific binding protein and one or more mispaired species) in the cell culture medium by size-exclusion ultra-performance liquid chromatography and mass spectrometry (SE-UPLC-MS); and (d) determining one or both of quality and purity of the multispecific binding protein produced by the cell line. In some embodiments, the methods comprise culturing a cell line comprising one or more polynucleotides encoding the product (e.g., an antibody, antibody fragment, Fc fusion protein, or multispecific binding protein and one or more mispaired species) under conditions suitable for production of the product by a cell line; separating, from the cell line, a cell culture medium comprising the product (e.g., an antibody, antibody fragment, Fc fusion protein, or multispecific binding protein and one or more mispaired species); detecting an amount of the product (e.g., an antibody, antibody fragment, Fc fusion protein, or multispecific binding protein and one or more mispaired species) in the cell culture medium by size-exclusion ultra-performance liquid chromatography and mass spectrometry (SE-UPLC-MS); and (d) determining one or both of quality and purity of the multispecific binding protein produced by the cell line and removing at least a portion of one or more of the mispaired species from the multispecific binding protein produced by the cell line. Any of the exemplary products described herein may find use in these and other methods.

Other aspects of the present disclosure relate to methods for screening a plurality of cell lines for production of a product (e.g., an antibody, antibody fragment, Fc fusion protein, or multispecific binding protein and one or more mispaired species). In some embodiments, the methods comprise detecting an amount of a product (e.g., an antibody, antibody fragment, Fc fusion protein, or multispecific binding protein and one or more mispaired species) produced by a first cell line (e.g., using any of the methods described herein) and detecting an amount of the product (e.g., an antibody, antibody fragment, Fc fusion protein, or multispecific binding protein and one or more mispaired species) produced by a second cell line (e.g., using any of the methods described herein), e.g., different from the first cell line. Any of the exemplary products described herein may find use in these and other methods.

In some embodiments, the methods further comprise comparing the amount of product (e.g., an antibody, antibody fragment, Fc fusion protein, or multispecific binding protein and one or more mispaired species) produced by the first cell line with the amount of product (e.g., an antibody, antibody fragment, Fc fusion protein, or multispecific binding protein and one or more mispaired species) produced by the second cell line; and based on the comparison, selecting the cell line that produced the higher amount of the product. In some embodiments, 2 or more, 3 or more, 4 or more, 5 or more, 10 or more, 20 or more, 30 or more, 40 or more, or 50 or more different cell lines are screened. Advantageously, the methods described herein are rapid and amenable to high-throughput screening.

In some embodiments, the methods further comprise detecting an amount of one or more mispaired species produced by the first cell line and detecting an amount of one or more mispaired species produced by the second cell line. In some embodiments, the methods further comprise, e.g., after detecting the amount of one or more mispaired species produced by the first and second cell lines, comparing the amount of the one or more mispaired species produced by the first cell line with the amount of the one or more mispaired species produced by the second cell line. In some embodiments, based on the comparison, the cell line that produced the higher ratio of multispecific binding protein to one or more mispaired species is selected. In some embodiments, the cell line is selected based on a higher ratio of multispecific binding protein to the amount of one or more individual mispaired species, and/or based on a higher ratio of multispecific binding protein to the overall amount of mispaired species.

In some embodiments, the selected cell line is selected for use as a production cell line.

Multispecific Binding Proteins

Certain aspects of the present disclosure relate to multi-specific binding proteins.

In some embodiments, the multispecific binding protein comprises an association of two or more polypeptide chains comprising at least a first polypeptide chain and a second polypeptide chain different from the first polypeptide chain. For example, in some embodiments, the multispecific binding protein is a bispecific antibody or bispecific Fc fusion protein. In some embodiments, the multispecific binding protein is a trispecific antibody or trispecific Fc fusion protein. In some embodiments, the one or more mispaired species comprise two or more polypeptide chains comprising at least one of the first and second polypeptide chains in an association other than that of the multispecific binding protein.

In some embodiments, the multispecific binding protein is a multispecific antibody comprising a first antibody heavy chain, a first antibody light chain, a second antibody heavy chain different from the first antibody heavy chain, and a second antibody light chain different from the first antibody light chain. In some embodiments, the one or more mis-paired species comprises one or more of: an association of four polypeptide chains of the multispecific antibody that comprises two of the first antibody heavy chains; an asso-ciation of four polypeptide chains of the multispecific anti-body that comprises two of the second antibody heavy chains; an association of four polypeptide chains of the multispecific antibody that comprises two of the first anti-body light chains; and an association of four polypeptide chains of the multispecific antibody that comprises two of the second antibody light chains.

In some embodiments, the multispecific binding proteins comprise four polypeptide chains that form three antigen binding sites that specifically bind to one or more target proteins, wherein a first pair of polypeptides forming the binding protein possess dual variable domains having a cross-over orientation and wherein a second pair of poly-peptides forming the binding protein possess a single vari-able domain.

In some embodiments, the multispecific binding proteins comprise one or two Fc regions fused to one, two, three, or more antigen binding domains or other polypeptides (e.g., an Fc fusion protein). In some embodiments, the multispe-cific binding protein is a dual variable domain (DVD) immunoglobulin, e.g., as described in WO2012061558. In some embodiments, the multispecific binding protein com-prises dual variable domains having a cross-over orientation, e.g., as described in WO2012135345. In some embodiments, the binding protein comprises four polypeptide chains that form four antigen binding sites, wherein two polypeptide chains have a structure represented by the formula:

$$V_{L1}\text{-}L_1\text{-}V_{L2}\text{-}L_2\text{-}C_L \qquad \text{[I]}$$

and two polypeptide chains have a structure represented by the formula:

$$V_{H2}\text{-}L_3\text{-}V_{H1}\text{-}L_4\text{-}C_{H1}\text{-}Fc \qquad \text{[II]}$$

wherein:

$V_{L1}$ is a first immunoglobulin light chain variable domain;

$V_{L2}$ is a second immunoglobulin light chain variable domain;

$V_{H1}$ is a first immunoglobulin heavy chain variable domain;

$V_{R2}$ is a second immunoglobulin heavy chain variable domain;

$C_L$ is an immunoglobulin light chain constant domain;

$C_{H1}$ is the immunoglobulin $C_{H1}$ heavy chain constant domain;

Fc is the immunoglobulin hinge region and $C_{H2}$, $C_{H3}$ immunoglobulin heavy chain constant domains; and $L_1$, $L_2$. $L_3$, and $L_4$ are amino acid linkers; and wherein the polypeptides of formula I and the polypep-tides of formula II form a cross-over light chain-heavy chain pair.

In some embodiments, each of the three antigen binding sites binds a different target (e.g., polypeptide antigen). In some embodiments, the trispecific binding protein com-prises four polypeptide chains that form the three antigen binding sites, wherein a first polypeptide chain comprises a structure represented by the formula:

$$V_{L2}\text{-}L_1\text{-}V_{L1}\text{-}L_2\text{-}C_L \qquad \text{[I]}$$

and a second polypeptide chain comprises a structure represented by the formula:

$$V_{H1}\text{-}L_3\text{-}V_{H2}\text{-}L_4\text{-}C_{H1}\text{-}hinge\text{-}C_{H2}\text{—}C_{H3} \qquad \text{[II]}$$

and a third polypeptide chain comprises a structure rep-resented by the formula:

$$V_{H3}\text{—}C_{H1}\text{-}hinge\text{-}C_{H2}\text{—}C_{H3} \qquad \text{[III]}$$

and a fourth polypeptide chain comprises a structure represented by the formula:

$$V_{L1}\text{—}C_L \qquad \text{[IV]}$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair.

In some embodiments, the polypeptide of formula I and the polypeptide of formula II form a cross-over light chain-heavy chain pair. In some embodiments, $V_{H1}$ and $V_{L1}$ form a first antigen binding site, wherein $V_{H2}$ and $V_{L2}$ form a second antigen binding site, and wherein $V_{H3}$ and $V_{L3}$ form a third antigen binding site.

In some embodiments, the one or more mispaired species comprise one or more of: an association of four polypeptide chains of the binding protein that comprises two polypeptide chains according to formula I; an association of four polypeptide chains of the binding protein that comprises two polypeptide chains according to formula II; an association of four polypeptide chains of the binding protein that comprises two polypeptide chains according to formula III; and an association of four polypeptide chains of the binding protein that comprises two polypeptide chains according to formula IV.

In some embodiments, the multispecific binding proteins are trispecific and/or trivalent. In some embodiments, the multispecific binding proteins are bispecific and/or bivalent.

It is contemplated that any of the antigen binding sites described herein may find use in a trispecific binding protein of the present disclosure, e.g., comprising four polypeptide chains having the structures described supra. For example, in some embodiments, a trispecific binding protein of the present disclosure comprises a VH1 and VL1 domain pair that form a first antigen binding site, a VH2 and VL2 domain pair that form a second antigen binding site, and a VH3 and VL3 domain pair that form a third antigen binding site. In some embodiments, a trispecific binding protein of the present disclosure comprises a VH1 and VL1 domain pair that form a first antigen binding site, a VH2 and VL2 domain pair that form a second antigen binding site that binds a CD3 polypeptide, and a VH3 and VL3 domain pair that form a third antigen binding site. In some embodiments, a trispecific binding protein of the present disclosure comprises a VH1 and VL1 domain pair that form a first antigen binding site that binds a CD28 polypeptide, a VH2 and VL2 domain pair that form a second antigen binding site that binds a CD3 polypeptide, and a VH3 and VL3 domain pair that form a third antigen binding site. In some embodiments, a trispecific binding protein of the present disclosure comprises a VH1 and VL1 domain pair that form a first antigen binding site, a VH2 and VL2 domain pair that form a second antigen binding site that binds a CD3 polypeptide, and a VH3 and VL3 domain pair that form a third antigen binding site that binds a tumor target protein. In some embodiments, a trispecific binding protein of the present disclosure comprises a VH1 and VL1 domain pair that form a first antigen binding site that binds a CD28 polypeptide, a VH2 and VL2 domain pair that form a second antigen binding site that binds a CD3 polypeptide, and a VH3 and VL3 domain pair that form a third antigen binding site that binds an HIV target protein. In some embodiments, a trispecific binding protein of the present disclosure comprises a VH1 and VL1 domain pair that form a first antigen binding site that binds an HIV target protein, a VH2 and VL2 domain pair that form a second antigen binding site that binds an HIV target protein, and a VH3 and VL3 domain pair that form a third antigen binding site that binds an HIV target protein. In some embodiments, a trispecific binding protein of the present disclosure comprises a VH1 and VL1 domain pair that form a first antigen binding site that binds a CD28 polypeptide, a VH2 and VL2 domain pair that form a second antigen binding site that binds a CD3 polypeptide, and a VH3 and VL3 domain pair that form a third antigen binding site that binds a tumor target protein. In some embodiments, a trispecific binding protein of the present disclosure comprises a VH1 and VL1 domain pair that form a first antigen binding site that binds a CD28 polypeptide, a VH2 and VL2 domain pair that form a second antigen binding site that binds a CD3 polypeptide, and a VH3 and VL3 domain pair that form a third antigen binding site that binds a CD38 polypeptide. In some embodiments, a trispecific binding protein of the present disclosure comprises a VH1 and VL1 domain pair that form a first antigen binding site that binds a CD28 polypeptide, a VH2 and VL2 domain pair that form a second antigen binding site that binds a CD3 polypeptide, and a VH3 and VL3 domain pair that form a third antigen binding site that binds a HER2 polypeptide.

In some embodiments, a binding protein of the present disclosure binds one or more tumor target proteins and one or more T cell target proteins. In some embodiments, the binding protein is capable of specifically binding one tumor target protein and two different epitopes on a single T cell target protein. In some embodiments, the binding protein is capable of specifically binding one tumor target protein and two different T cell target proteins (e.g., CD28 and CD3). In some embodiments, the first and second polypeptide chains of the binding protein form two antigen binding sites that specifically target two T cell target proteins, and the third and fourth polypeptide chains of the binding protein form an antigen binding site that specifically binds a tumor target protein. In some embodiments, the target protein is CD38 or HER2. Additional tumor target proteins are provided infra. In some embodiments, the one or more T cell target proteins are one or more of CD3 and CD28.

Exemplary multispecific binding proteins that may be used in the methods of the present disclosure also include, without limitation, those described in International Publication Nos. WO2017074878, WO2017180913, WO2018151841, and WO2019074973.

In some embodiments, the binding protein is a trispecific binding protein. In some embodiments, the trispecific binding protein comprising an antigen binding site that binds a CD38 polypeptide, an antigen binding site that binds a CD28 polypeptide, and an antigen binding site that binds a CD3 polypeptide. In some embodiments, the binding protein is a trispecific binding protein comprising four polypeptides comprising three antigen binding sites, wherein the polypeptide of formula I and the polypeptide of formula II form a cross-over light chain-heavy chain pair (e.g., as described herein). In some embodiments, the VH and VL domains of any of the anti-CD38 antigen binding sites described above represent $V_{H3}$ and $V_{L3}$ and form a third antigen binding site that binds a CD38 polypeptide. In some embodiments, $V_{H1}$ and $V_{L1}$ form a first antigen binding site that binds a CD28 polypeptide, $V_{H2}$ and $V_{L1}$ form a second antigen binding site that binds a CD3 polypeptide, and $V_{H3}$ and $V_{L3}$ and form a third antigen binding site that binds a CD38 polypeptide.

In some embodiments, a binding protein comprising an antigen binding site that binds a HER2 polypeptide is monospecific and/or monovalent, bispecific and/or bivalent, trispecific and/or trivalent, or multispecific and/or multivalent. In some embodiments, a binding protein that comprises an antigen binding site that binds a HER2 polypeptide is a trispecific binding protein comprising four polypeptides that form three antigen binding sites as described supra, wherein $V_{H3}$ and $V_{L3}$ domain pair that form a third antigen binding site that binds a HER2 polypeptide In some embodiments, a binding protein of the present disclosures comprises an antigen binding site that binds a tumor target protein. In some embodiments, the tumor target protein is a CD38 polypeptide (e.g., a human CD38 polypeptide). In some embodiments, the tumor target protein is a HER2 polypeptide (e.g., a human HER2 polypeptide). In some embodiments, a tumor target protein of the present disclosure includes, without limitation, A2AR, APRIL, ATP-Dase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-la), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), $CX3C_L1$ (also known as SCYD1), CXCL12 (also known as SDF1), CXCL13, CXCR3, DNGR-1, ectonucleoside triphosphate diphospho-hydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, MUC-1, NCR3LG1, NKG2D, NTPDase-1, OX40, OX4OL, PD-1H, platelet receptor, PROM1, 5152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In some embodiments, a binding protein of the present disclosures comprises an antigen binding site that binds an HIV target protein. In some embodiments, a binding protein of the present disclosures comprises three antigen binding sites that each bind to an HIV target protein. In some embodiments, the binding proteins specifically bind to one or more HIV target proteins (e.g., as described infra) and one or more target proteins on a T-cell including T cell receptor complex. Examples of target proteins on T cells include but are not limited to CD3 and CD28, among others. In some embodiments, the HIV target protein is glycoprotein 120, glycoprotein 41, or glycoprotein 160. In some embodiments, a binding protein binds one or more of: glycoprotein 120, glycoprotein 41, and glycoprotein 160. Exemplary HIV target proteins include, without limitation, MPER of the HIV-1 gp41 protein, a CD4 binding site of the HIV-1 gp120 protein, a glycan in the V3 loop of the HIV-1 gp120 protein, or a trimer apex of the HIV-1 gp120 protein or gp160. For example, in some embodiments, a binding protein of the present disclosure comprises an antigen binding site that binds a CD4 binding site of the HIV-1 gp120 protein. Exemplary antigen binding sites that bind HIV target proteins contemplated for use herein include, without limitation, those described in International Publication No. WO2017/074878, such as those from antibodies CD4BS "a", CD4BS "b", MPER, MPER 100W, V1N2 "a", V1N2 "b", or V3.

In some embodiments, a binding protein comprising an antigen binding site that binds a CD28 polypeptide is monospecific and/or monovalent, bispecific and/or bivalent, trispecific and/or trivalent, or multispecific and/or multivalent. In some embodiments, a binding protein that comprises an antigen binding site that binds a CD28 polypeptide is a trispecific binding protein comprising four polypeptides that form three antigen binding sites. In some embodiments, a binding protein that comprises an antigen binding site that binds a CD28 polypeptide is a trispecific binding protein comprising four polypeptides that form three antigen binding sites, one of which binds a CD28 polypeptide, and one of which binds a CD3 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a CD38 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a HER2 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a tumor target protein.

In some embodiments of any of the above embodiments, the binding protein is a trispecific binding protein. In some embodiments, the trispecific binding protein comprising an antigen binding site that binds a tumor target protein (including, without limitation, CD38 or HER2), an antigen binding site that binds a CD28 polypeptide, and an antigen binding site that binds a CD3 polypeptide. In some embodiments, the binding protein is a trispecific binding protein comprising four polypeptides comprising three antigen binding sites, wherein the polypeptide of formula I and the polypeptide of formula II form a cross-over light chain-heavy chain pair (e.g., as described herein). In some embodiments, the VH and VL domains of any of the anti-CD28 antigen binding sites described above represent $V_{H1}$ and $V_{L1}$ and form a first antigen binding site that binds a CD28 polypeptide. In some embodiments, $V_{H1}$ and $V_{L1}$ and form a first antigen binding site that binds a CD28 polypeptide, $V_{H2}$ and Vu form a second antigen binding site that binds a CD3 polypeptide, and $V_{H3}$ and $V_{L3}$ and form a third antigen binding site that binds a tumor target protein (including, without limitation, CD38 or HER2).

In some embodiments, a binding protein comprising an antigen binding site that binds a CD3 polypeptide is monospecific and/or monovalent, bispecific and/or bivalent, trispecific and/or trivalent, or multispecific and/or multivalent. In some embodiments, a binding protein that comprises an antigen binding site that binds a CD3 polypeptide is a trispecific binding protein comprising four polypeptides that form three antigen binding sites. In some embodiments, a binding protein that comprises an antigen binding site that binds a CD3 polypeptide is a trispecific binding protein comprising four polypeptides that form three antigen binding sites, one of which binds a CD28 polypeptide, and one of which binds a CD3 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a CD38 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a HER2 polypeptide. In some embodiments, a binding protein that comprises an antigen binding site that binds a CD3 polypeptide is a trispecific binding protein comprising four polypeptides that form three antigen binding sites, one of which binds a CD28 polypeptide, one of which binds a CD3 polypeptide, and one of which binds a tumor target protein.

In some embodiments, the binding protein is a trispecific binding protein. In some embodiments, the trispecific binding protein comprising an antigen binding site that binds a tumor target protein (including, without limitation, CD38 or HER2), an antigen binding site that binds a CD28 polypeptide, and an antigen binding site that binds a CD3 polypeptide. In some embodiments, the binding protein is a trispecific binding protein comprising four polypeptides comprising three antigen binding sites, wherein the polypeptide of formula I and the polypeptide of formula II form a cross-over light chain-heavy chain pair (e.g., as described herein). In some embodiments, $V_{H2}$ and $V_{L2}$ and form a second antigen binding site that binds a CD3 polypeptide. In some embodiments, $V_{H1}$ and $V_{L1}$ form a first antigen binding site that binds a CD28 polypeptide, $V_{H2}$ and $V_{L2}$ and form a second antigen binding site that binds a CD3 polypeptide, and $V_{H3}$ and $V_{L3}$ form a third antigen binding site that binds a tumor target protein (including, without limitation, CD38 or HER2).

Linkers

In some embodiments, the linkers $L_1$, $L_2$, $L_3$, and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$, and $L_4$ in one binding protein may all have the same amino acid sequence or may all have different amino acid sequences.

Examples of suitable linkers include, for example, GGGGSGGGGS (SEQ ID NO:1), GGGGSGGGGSGGGGS (SEQ ID NO: 2), S, RT, TKGPS (SEQ ID NO:3), GQPKAAP (SEQ ID NO: 4), GGSGSSGSGG (SEQ ID NO: 5), and DKTHT (SEQ ID NO:6), as well as those disclosed in International Publication Nos. WO2017/074878 and WO2017/180913. The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length.

In some embodiments, $L_1$, $L_2$, $L_3$ and $L_4$ each independently are zero amino acids in length or comprise a sequence selected from the group consisting of GGGGSGGGGS (SEQ ID NO:1), GGGGSGGGGSGGGGS (SEQ ID NO: 2), S, RT, TKGPS (SEQ ID NO: 3), GQPKAAP (SEQ ID NO: 4 and GGSGSSGSGG (SEQ ID NO: 5). In some embodiments, $L_1$, $L_2$, $L_3$ and $L_4$ each independently comprise a sequence selected from the group consisting of GGGGSGGGGS (SEQ ID NO:1) GGGGSGGGGSGGGGS (SEQ ID NO: 2), S, RT, TKGPS (SEQ ID NO: 3), GQP-KAAP (SEQ ID NO: 4), and GGSGSSGSGG (SEQ ID NO: 5). In some embodiments, $L_1$ comprises the sequence GQP-KAAP (SEQ ID NO: 4), $L_2$ comprises the sequence TKGPS (SEQ ID NO:3), $L_3$ comprises the sequence S, and $L_4$ comprises the sequence RT.

In some embodiments, at least one of $L_1$, $L_2$, $L_3$ or $L_4$ comprises the sequence DKTHT (SEQ ID NO:6). In some embodiments, $L_1$, $L_2$, $L_3$ and $L_4$ comprise the sequence DKTHT (SEQ ID NO:6).

Fc Regions and Constant Domains

In some embodiments, a binding protein of the present disclosure comprises a second polypeptide chain further comprising an Fc region linked to $C_{H1}$, the Fc region comprising an immunoglobulin hinge region and $C_{H2}$ and $C_{H3}$ immunoglobulin heavy chain constant domains. In some embodiments, a binding protein of the present disclosure comprises a third polypeptide chain further comprising an Fc region linked to $C_{H1}$, the Fc region comprising an immunoglobulin hinge region and $C_{H2}$ and $C_{H3}$ immunoglobulin heavy chain constant domains. In some embodiments, a binding protein of the present disclosure comprises a second polypeptide chain further comprising an Fc region linked to $C_{H1}$, the Fc region comprising an immunoglobulin hinge region and $C_{H2}$ and $C_{H3}$ immunoglobulin heavy chain constant domains, and a third polypeptide chain further comprising an Fc region linked to $C_{H1}$, the Fc region comprising an immunoglobulin hinge region and $C_{H2}$ and $C_{H3}$ immunoglobulin heavy chain constant domains.

In some embodiments, a binding protein of the present disclosure comprises a full-length antibody heavy chain or a polypeptide chain comprising an Fc region. In some embodiments, the Fc region is a human Fc region, e.g., a human IgG1, IgG2, IgG3, or IgG4 Fc region. In some embodiments, the Fc region includes an antibody hinge, $C_{H1}$, $C_{H2}$, $C_{H3}$, and optionally $C_{H4}$ domains. In some embodiments, the Fc region is a human IgG1 Fc region. In some embodiments, the Fc region is a human IgG4 Fc region. In some embodiments, the Fc region includes one or more of the mutations described infra. In some embodiments, the Fc region is an Fc region of one of the heavy chain polypeptides (e.g., polypeptide 2 or 3) of a binding protein shown in Table 4. In some embodiments, the heavy chain constant region is a constant region of one of the heavy chain polypeptides (e.g., polypeptide 2 or 3) of a binding protein shown in Table 4. In some embodiments, the light chain constant region is a constant region of one of the light chain polypeptides (e.g., polypeptide 1 or 4) of a binding protein shown in Table 4.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In some embodiments, a binding protein of the present disclosure (e.g., a trispecific binding protein) comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino acid substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349, 366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349, 366, 368, and 407 of human IgG1 or IgG4 according to EU Index. In some embodiments, the amino acid substitutions are Y349C, T366S, L368A, and Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366 and optionally 354 of human IgG1 or IgG4 according to EU Index, wherein the amino acid substitutions are T366W or T366Y and optionally S354C; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366 and optionally 354 of human IgG1 or IgG4 according to EU Index, wherein the amino acid substitutions are T366W or T366Y and optionally S354C.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution at position corresponding to position 366 of human IgG1 or IgG4 according to EU Index, wherein the amino acid substitution is T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366, 368, and/or 407 and of human IgG1 or IgG4 according to EU Index, wherein the amino acid substitutions are T366S, L368A, and/or Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366, 368, and/or 407 and of human IgG1 or IgG4 according to EU Index, wherein the amino acid substitutions are T366S, L368A, and/or Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution at position corresponding to position 366 of human IgG1 or IgG4 according to EU Index, wherein the amino acid substitution is T366W.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the first and/or second Fc regions are human IgG1 Fc regions. In some embodiments, the first and/or second Fc regions are human IgG4 Fc regions.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 354, 366, and 409 of human IgG4 according to EU Index, wherein the amino acid substitutions are S228P, S354C, T366W, and R409K; and wherein the third polypeptide chain further comprises a second Fc region linked to CH1, the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 349, 366, 368, 407, and 409 of human IgG4 according to EU Index, wherein the amino acid substitutions are S228P, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 354, 366, and 409 of human IgG4 according to EU Index, wherein the amino acid substitutions are S228P, S354C, T366W, and R409K.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235, 354, and 366 of human IgG4 according to EU Index, wherein the amino acid substitutions are F234A, L235A, S354C, and T366W; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234, 235, 349, 366, 368, and 407 of human IgG4 according to EU Index, wherein the amino acid substitutions are F234A, L235A, Y349C, T366S, L368A, and Y407V. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 234, 235, 349, 366, 368, and 407 of human IgG4 according to EU Index, wherein the amino acid substitutions are F234A, L235A, Y349C, T366S, L368A, and Y407V; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 234, 235, 354, and 366 of human IgG4 according to EU Index, wherein the amino acid substitutions are F234A, L235A, S354C, and T366W.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the Fc regions of the second and the third polypeptide chains are human IgG4 Fc regions, and the Fc regions each comprise amino acid substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A.

In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 234, 235, 354, 366, and 409 of human IgG4 according to EU Index, wherein the amino acid substitutions are S228P, F234A, L235A, S354C, T366W, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 349, 366, 368, 407, and 409 of human IgG4 according to EU Index, wherein the amino acid substitutions are S228P, F234A, L235A, Y349C, T366S, L368A, Y407V, and R409K. In some embodiments, the second polypeptide chain further comprises a first Fc region linked to CH1, wherein the first Fc region is a human IgG4 Fc region comprising an immunoglobulin hinge region and CH2 and CH3 immunoglobulin heavy chain constant domains, wherein the first Fc region comprises amino acid substitutions at positions corresponding to positions 228, 234, 235, 349, 366, 368, 407, and 409 of human IgG4 according to EU Index, wherein the amino acid substitutions are S228P, F234A, L235A, Y349C, T366S, L368A, Y407V, and R409K; and wherein the third polypeptide chain further comprises a second Fc region linked to CH1, wherein the second Fc region is a human IgG4 Fc region comprising an immunoglobulin hinge region and CH2 and CH3 immunoglobulin heavy chain constant domains, wherein the second Fc region comprises amino acid substitutions at positions corresponding to positions 228, 234, 235, 354, 366, and 409 of human IgG4 according to EU Index, wherein the amino acid substitutions are S228P, F234A, L235A, S354C, T366W, and R409K.

In some embodiments, the Fc region is a human IgG4 Fc region comprising one or more mutations that reduce or eliminate FcγI and/or FcγII binding. In some embodiments, the Fc region is a human IgG4 Fc region comprising one or more mutations that reduce or eliminate FcγI and/or FcγII binding but do not affect FcRn binding. In some embodiments, the Fc region is a human IgG4 Fc region comprising amino acid substitutions at positions corresponding to positions 228 and/or 409 of human IgG4 according to EU Index. In some embodiments, the amino acid substitutions are S228P and/or R409K. In some embodiments, the Fc region is a human IgG4 Fc region comprising amino acid substitutions at positions corresponding to positions 234 and/or 235 of human IgG4 according to EU Index. In some embodiments, the amino acid substitutions are F234A and/or L235A. In some embodiments, the Fc region is a human IgG4 Fc region comprising amino acid substitutions at positions corresponding to positions 228, 234, 235, and/or 409 of human IgG4 according to EU Index. In some embodiments, the amino acid substitutions are S228P, F234A, L235A, and/or R409K. In some embodiments, the Fc region is a human IgG4 Fc region comprising amino acid substitutions at positions corresponding to positions 233-236 of human IgG4 according to EU Index. In some embodiments, the amino acid substitutions are E233P, F234V, L235A, and a deletion at 236. In some embodiments, the Fc region is a human IgG4 Fc region comprising amino acid mutations at substitutions corresponding to positions 228, 233-236, and/or 409 of human IgG4 according to EU Index. In some embodiments, the amino acid mutations are S228P; E233P, F234V, L235A, and a deletion at 236; and/or R409K.

In some embodiments, the Fc region comprises one or more mutations that reduce or eliminate Fc receptor binding and/or effector function of the Fc region (e.g., Fc receptor-mediated antibody-dependent cellular phagocytosis (ADCP), complement-dependent cytotoxicity (CDC), and/or antibody-dependent cellular cytotoxicity (ADCC)).

In some embodiments, the Fc region is a human IgG1 Fc region comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298, 299, and/or 300 of human IgG1 according to EU Index. In some embodiments, the amino acid substitutions are S298N, T299A, and/or Y300S.

In some embodiments, a binding protein of the present disclosure comprises one or more mutations to improve stability, e.g., of the hinge region and/or dimer interface of IgG4 (See e.g., Spiess, C. et al. (2013) *J. Biol. Chem.* 288:26583-26593). In some embodiments, the mutation comprises substitutions at positions corresponding to positions 228 and 409 of human IgG4 according to EU Index, wherein the amino acid substitutions are S228P and R409K. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, a binding protein of the present disclosure comprises knob and hole mutations and one or more mutations to improve stability. In some embodiments, the first and/or second Fc regions are human IgG4 Fc regions.

In some embodiments, the Fc region is a human IgG1 Fc region comprising one or more amino acid substitutions at positions corresponding to positions 234, 235, and/or 329 of human IgG1 according to EU Index. In some embodiments, the amino acid substitutions are L234A, L235A, and/or P329A. In some embodiments, the Fc region is a human IgG1 Fc region comprising amino acid substitutions at positions corresponding to positions 298, 299, and/or 300 of human IgG1 according to EU Index. In some embodiments, the amino acid substitutions are S298N, T299A, and/or Y300S.

Nucleic Acids and Vectors

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, MOLECULAR CLONING: A LABORATORY MANUAL (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40

(SV40), and the like), from heterologous eukaryotic promoters (such as the actin promoter, an immunoglobulin promoter, from heat-shock promoters, and the like), the CAG-promoter (Niwa et al., Gene 108(2):193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Host Cells

Other aspects of the present disclosure relate to a host cell (e.g., an isolated host cell) comprising one or more isolated polynucleotides, vectors, and/or vector systems described herein. For example, a host cell or cell line may be used to produce a product of the present disclosure.

In some embodiments, an isolated host cell of the present disclosure is cultured in vitro. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293™ cells, Chinese hamster ovary (CHO) cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NS0 and Sp2/0 cells).

In some embodiments, a host cell or cell line of the present disclosure is cultured in a continuous cell culture, e.g., in a stirred tank bioreactor. In some embodiments, a host cell or cell line of the present disclosure is cultured in a batch cell culture. Suitable stirred tank and batch cell culture equipment and techniques are known in the art; exemplary and non-limiting descriptions are provided in the Examples infra. Exemplary conditions and techniques suitable for production of any of the products described herein using a host cell or cell line described herein (e.g., supra) are known in the art.

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell. Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

EXAMPLES

The Examples that follow are illustrative of specific embodiments of the disclosure, and various uses thereof. They are set forth for explanatory purposes only, and should not be construed as limiting the scope of the invention in any way.

Example 1: Identification and Clonal Variation of Chain Mispairing for Asymmetric Trispecific Binding Proteins IgG-like multi-specific antibodies with asymmetric constructs have become widely used formats for therapeutic applications in recent years. Correct assembly of the subunits in this class of therapeutics is a critical quality attribute (CQA) with direct impact on biological activity. Thus, early development efforts (e.g., clone selection) must be guided by information on potential chain mispairing to enable timely decision making and risk mitigation.

Mispaired antibodies can possess sub-optimal levels of the expected biological activity, and are considered product-related impurities. Removal of such mAb-related impurities requires additional purification steps post protein A (ProA) column, adding to the cost and timeline of process development. Therefore, any potential chain mispairing must be identified and monitored during early development, starting with cell line development. This calls for a high throughput analytical platform that enables screening a large number of samples for mis-mispairing levels with a quick turnaround time.

Intact protein mass spectrometry has been used for identification and relative quantitation of mispaired species in bispecific IgGs. Several different intact protein MS approaches based on reversed phase separation or size exclusion liquid chromatography for denaturing and native MS analysis have been reported (Wang, C. et al. *MAbs* 2018, 10 (8), 1226-1235; Schaefer, W. et al. *MAbs* 2016, 8 (1), 49-55; Schachner, L. et al. *Anal Chem* 2016, 88 (24), 12122-12127; Yin, Y. et al. *MAbs* 2016, 8 (8), 1467-1476). These approaches require the antibody be purified typically through Protein A affinity, prior to LC-MS analysis.

The following Examples describe a high throughput analytical platform consisting of denaturing size exclusion liquid chromatography (SEC) coupled with QToF MS for intact MS analysis of mAb species, such as the trispecific binding protein shown in FIG. 1A. This intact mass method can be performed directly in on the clarified harvest fluid with no prior purification or sample preparation. This method can be performed directly on the cell culture harvest fluid prior to Protein A purification to provide first-hand and unbiased information on the types and distribution of mAb-related species generated by the cells, giving insight into the performance and characteristics of the clones and growth conditions. This analytical platform has enabled screenings of large numbers of CHO (Chinese Hamster Ovary) cell clones expressing different tsAb constructs for mispairing and half antibody levels. Results from this intact mass analysis method, particularly early in development, facilitate the selection of CHO clones that produce tsAbs of suitable product quality.

Materials and Methods

Antibody Expression and Purification

Trispecific antibodies (tsAbs) were generated by co-expression of all four subunits in a single CHO host cell system using batch culture in the spin tubes or the fed-batch process in ambr® bioreactor system. Titer was determined on harvest fluid using Octet with ProA biosensors. Clarified cell culture harvest samples were stored frozen at −80° C. prior to mass spectrometry analysis. Purification of the tsAbs from the clarified cell culture fluids was performed using Protein A spin columns in a 96-well plate format using a Tecan liquid handling system, followed by concentration measurement using Octet.

IdeS Digestion of Antibodies

To a 10 µL solution of tsAb at a concentration of ~2 mg/mL, 20 µL of 25 mM Tris buffer pH 7.2 was added. The sample was mixed with 1.5 µL IdeS enzyme solution (66.6 unit/µL) from Genovis Inc. (Cambridge, MA, USA) followed by incubation at 37° C. for two hours.

Size-Exclusion Chromatography (SEC) for Mass Spectrometry (MS)

The size exclusion liquid chromatography (LC) separation was performed using a UPLC BEH SEC Column, 1.7 µm, 200 Å, 4.6×300 mm controlled by an Acquity UPLC H-Class (Waters Corp., Milford, MA, United States). For ProA purified antibody samples, 0.1% trifluoroacetic acid (TFA) in 30:70 acetonitrile:water at the flow rate of 0.2 mL/min for 15 minutes and for clarified harvest samples, 0.05% formic acid (FA) and 0.05% TFA in 30:70 acetonitrile:water at the flow rate of 0.1 mL/min (from 0 to 25 minutes) and 0.4 ml/min (from 25 to 33 minutes), in isocratic mode was used as the mobile phase. Both FA and TFA were LC-MS grade from Sigma (St. Louis, MO, United States). The LC-MS water and acetonitrile were from Thermo Fisher Scientific (Waltham, MA, United States).

Mass Spectrometry

The liquid chromatography (LC) was coupled to a Xevo G2 QToF mass spectrometer (Waters Corp., Milford, MA, United States) for online intact MS data acquisition in sensitivity mode and in the m/z range of 500-4000 using the following source parameters: 3 kV capillary voltage, 40 V sampling cone voltage, 2.5 V extraction cone voltage, 150° C. source temperature, 500° C. desolvation temperature, 50 L/hr cone gas flow, 800 L/hr desolvation gas flow, 6 V collision energy.

Data Analysis

The acquired LC-MS raw files were batch-processed using Byos® (Protein Metrics Inc.) for deconvolution and relative quantitation.

Results

Figure 1B:
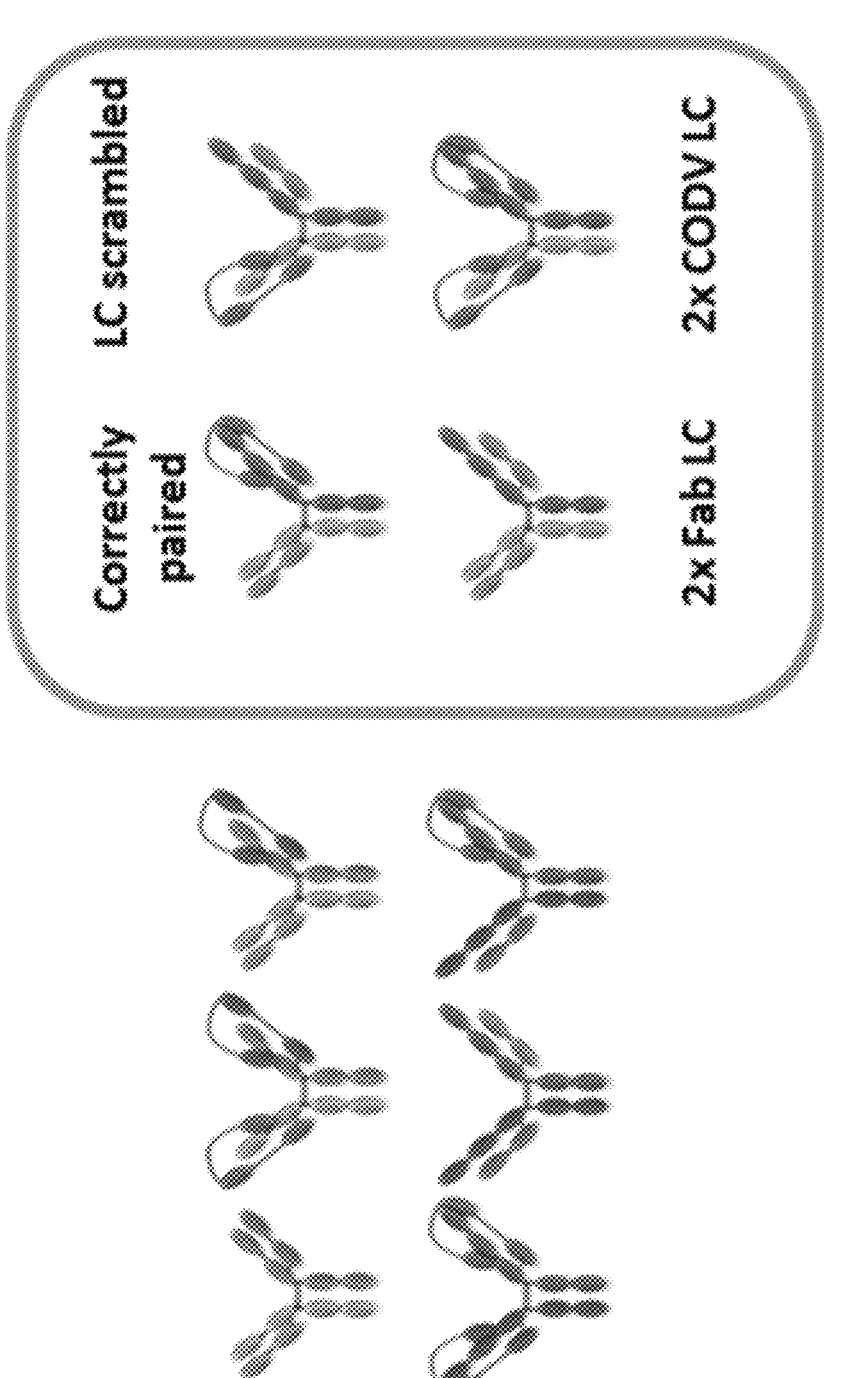
FIG. 1B illustrates species resulting from heavy chain (left) or light chain (right) mispairing. On left, shown are species that result from mispairing of two Fab heavy chains (top) or two CODV heavy chains (bottom). On right, shown are species that result from mispairing of two Fab light chains (bottom left), two CODV light chains (bottom right), or mispairing of Fab and CODV light chains to the wrong heavy chains (top right), as well as the correctly paired trispecific binding protein (top left).

Mispairing of heavy and light chains in tri-specific antibodies results in mass shifts from the expected mass of the correctly paired species, readily detectable by intact protein mass spectrometry. The only exception is the potential light chain scrambled molecules which have the same mass as the correctly paired structure and are thus not distinguishable by mass spectrometry (FIG. 1B).

Intact MS analysis of cell culture harvest fluid is challenged by the complex matrix and calls for effective chromatographic separation on-line with MS detection. Specifically tsAb species suffer from ion suppression by the overwhelming amount of free CODV (~36 kDa) and Fab (~23 kDa) light chains in the harvest and their inherently low ionization efficiency due to their large size (up to 210 kDa for some mis-paired species). Therefore, optimization of chromatography parameters including flow rate, mobile phase modifiers and its organic content, SEC column pore size, and protein load on the column as well as MS source parameters was undertaken during SE-UPLC-Intact MS method development in order to obtain high quality MS data from direct injection of the harvest fluid with no sample preparation.

An initial workflow included automated ProA purification of tsAb from clarified harvest followed by denaturing SEC-LC coupled with QToF MS for intact MS data acquisition. Denaturing SEC allows for fast (15 minutes) and efficient desalting as well as separation of tsAbs from over-expressed light chains that often co-purify with mAbs.

Figure 2A:
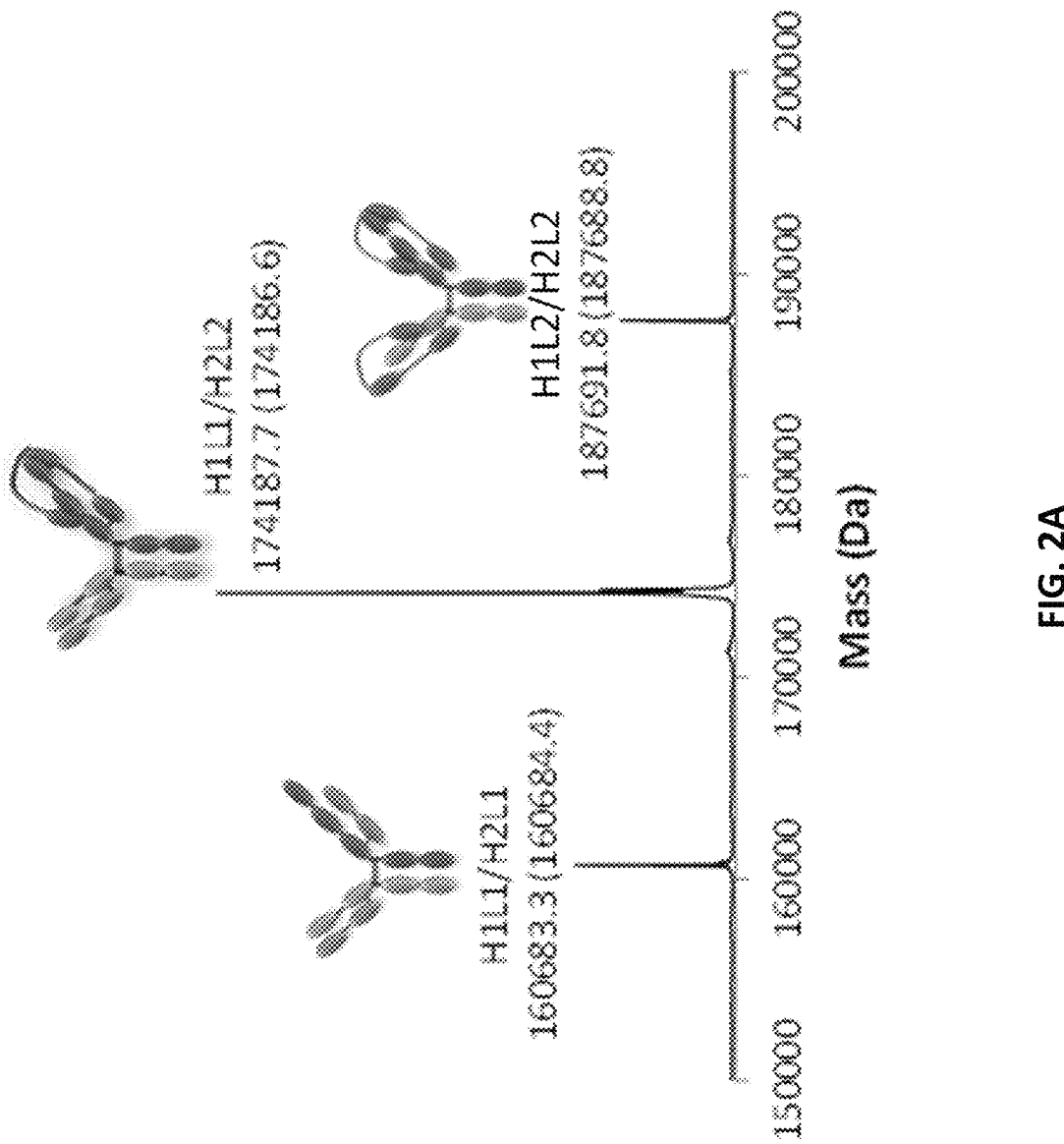
FIGS. 2A & 2B show deconvoluted mass spectrometry (MS) spectra for intact (FIG. 2A) and F(ab')2 fragments in IdeS-digested (FIG. 2B) anti-CD38 trispecific binding proteins, with different species labeled. Species depicted include correctly paired trispecific binding protein (H1L1/H2L2), mispaired species with two Fab light chains (H1L1/H2L1), and mispaired species with two CODV light chains (H1L2/H2L2). Annotations show experimental mass vs. theoretical mass (in parenthesis).
Figure 2B:
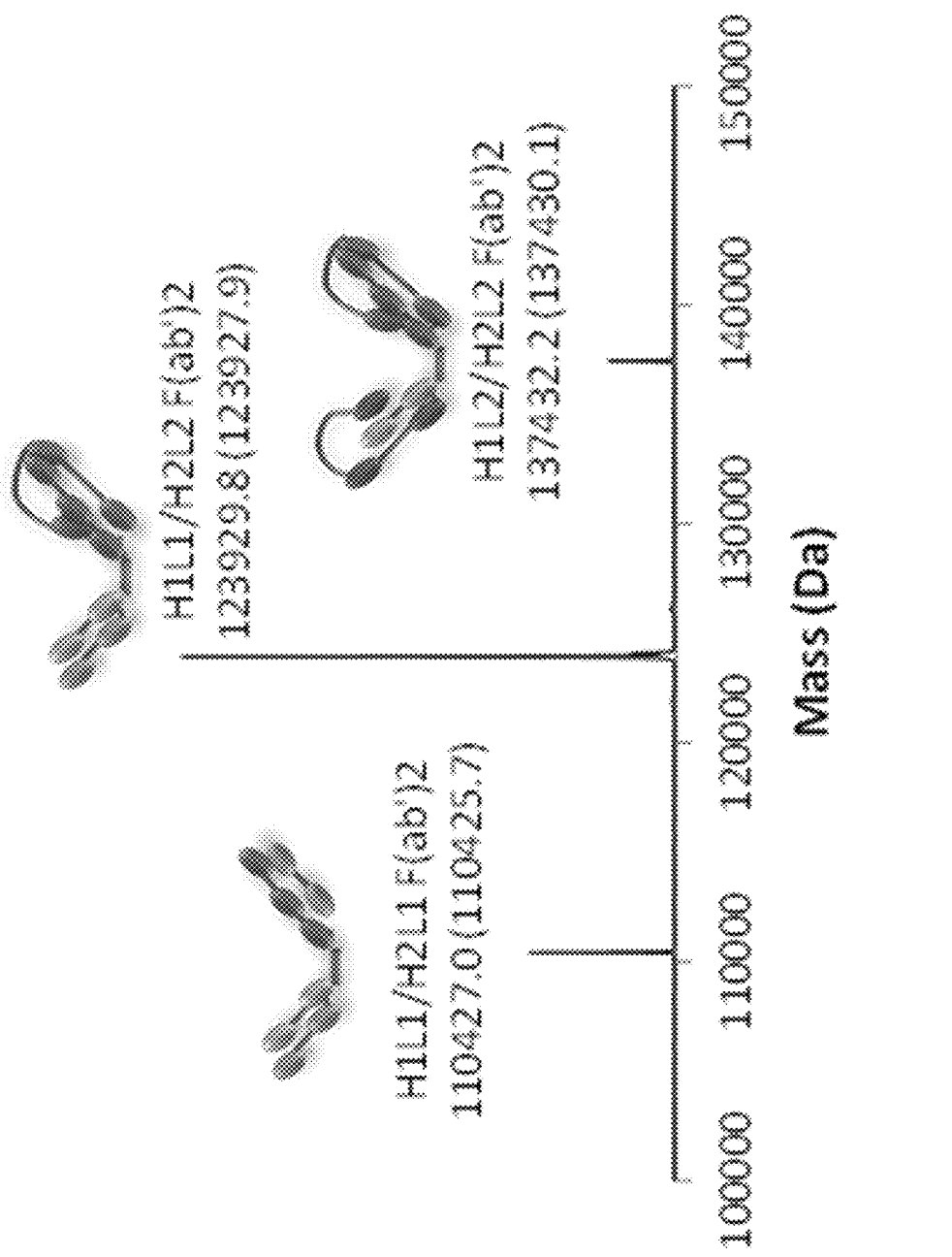

FIG. 2A shows the deconvoluted mass spectrum for a CD38 TCE tsAb, with the mass at 174188 Da corresponding to the desired assembly, H1L1/H2L2. Two other masses observed at 160683 Da and 187692 Da match the theoretical masses of light chain mispaired species H1L1/H2L1 and H1L2/H2L2 respectively. In order to further verify structural assignment of species, the tsAb sample was digested with IdeS, a cysteine protease that digests antibodies at a specific site below the hinge, generating a pool of F(ab')2 and Fc/2 fragments. As seen in FIG. 2B, three different Fab fragments with the same mass shift pattern observed in the intact molecules, appear after IdeS digestion, further confirming the light chain mispairing assignment.

Cell line development for protein therapeutics including antibodies is the foundation of early stage development. A major goal is to generate a stable monoclonal cell line (commonly CHO cells) that can consistently express the target recombinant protein at high quantity and with desired product quality attributes such as glycosylation, charge heterogeneity, etc. (Chusainow, J. et al. *Biotechnol Bioeng* 2009, 102 (4), 1182-96). In the context of multi-specific antibodies, potential mispairing of subunits is a critical quality attribute (CQA) that needs to be monitored during selection of pools and final production clones.

Intact MS analysis of ProA purified materials from 38 clones of CHO cells expressing anti-CD38 TCE using the denaturing SEC-intact MS method was undertaken to determine the types and relative levels of product-related impurities, including mispaired chains and half antibodies that co-purify with the desired tsAb form. The relative levels of different species were calculated based on mass intensities after deconvolution of the combined MS spectra acquired across the tsAb chromatographic peak. While different IgG-related species can vary widely in mass, especially half antibodies compared to full tsAb structures, and thus in their ionization efficiencies, MS-based relative quantitation of species is an effective tool for comparing and ranking clones based on their mispairing and ½ antibody levels.

Figure 3A:
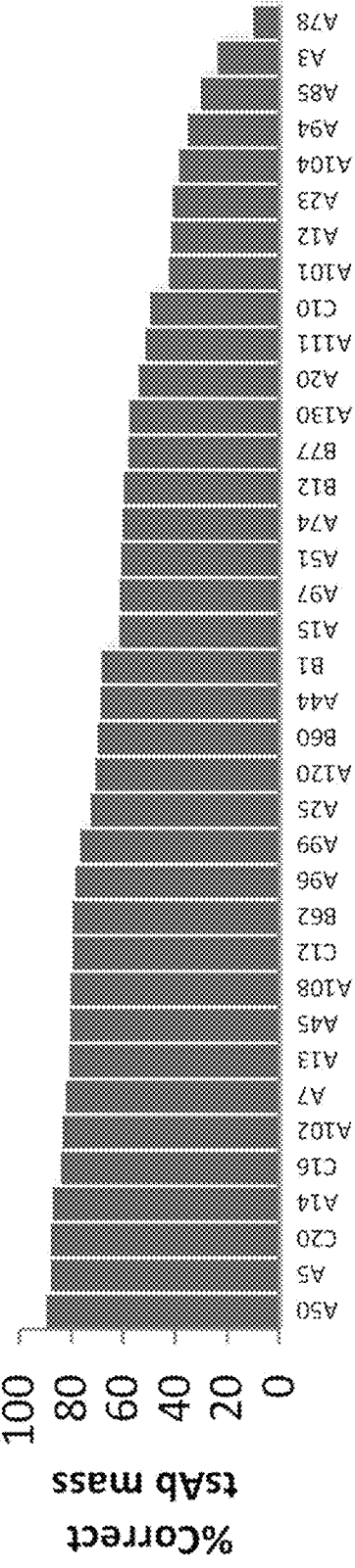
FIGS. 3A & 3B show production of trispecific binding protein from a series of clones.
Figure 3B:
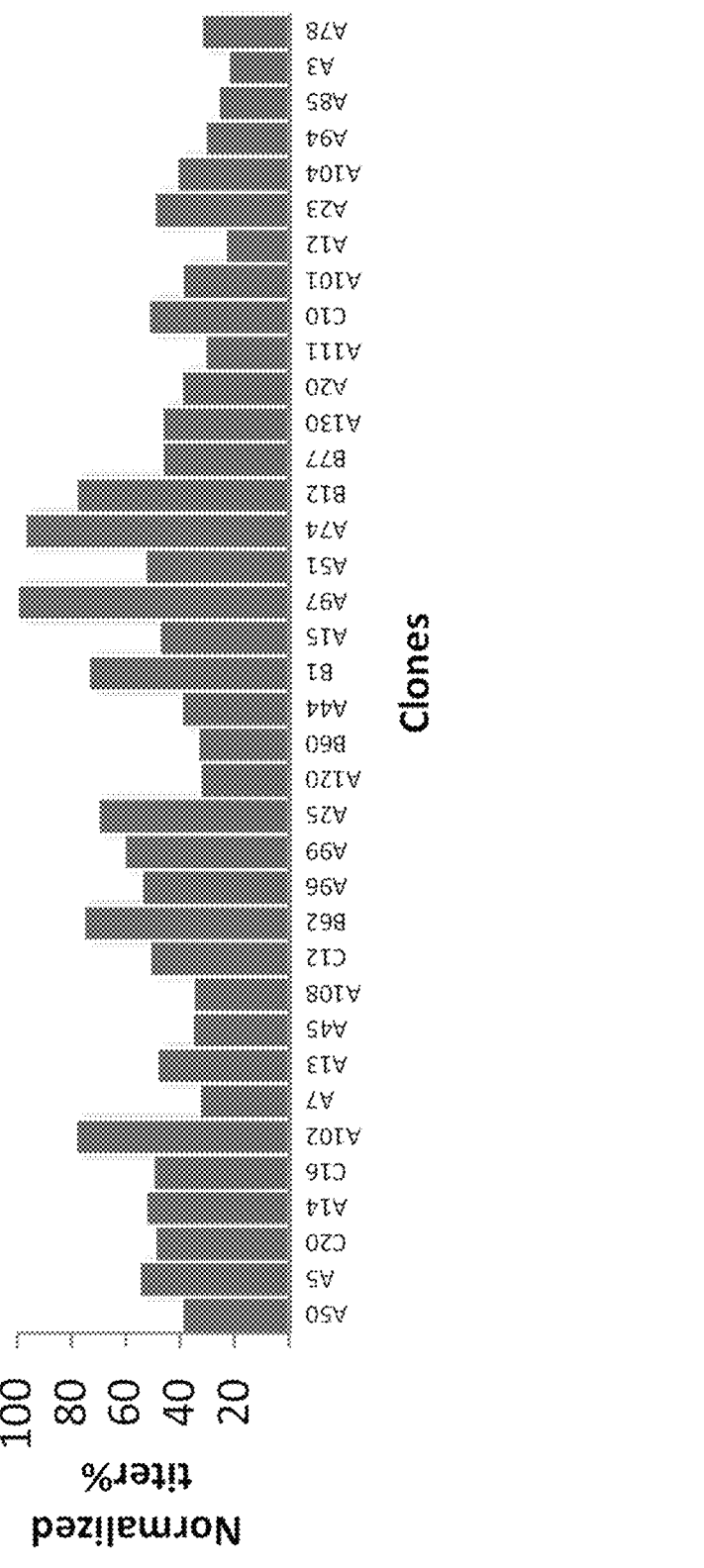
Figure 3C:
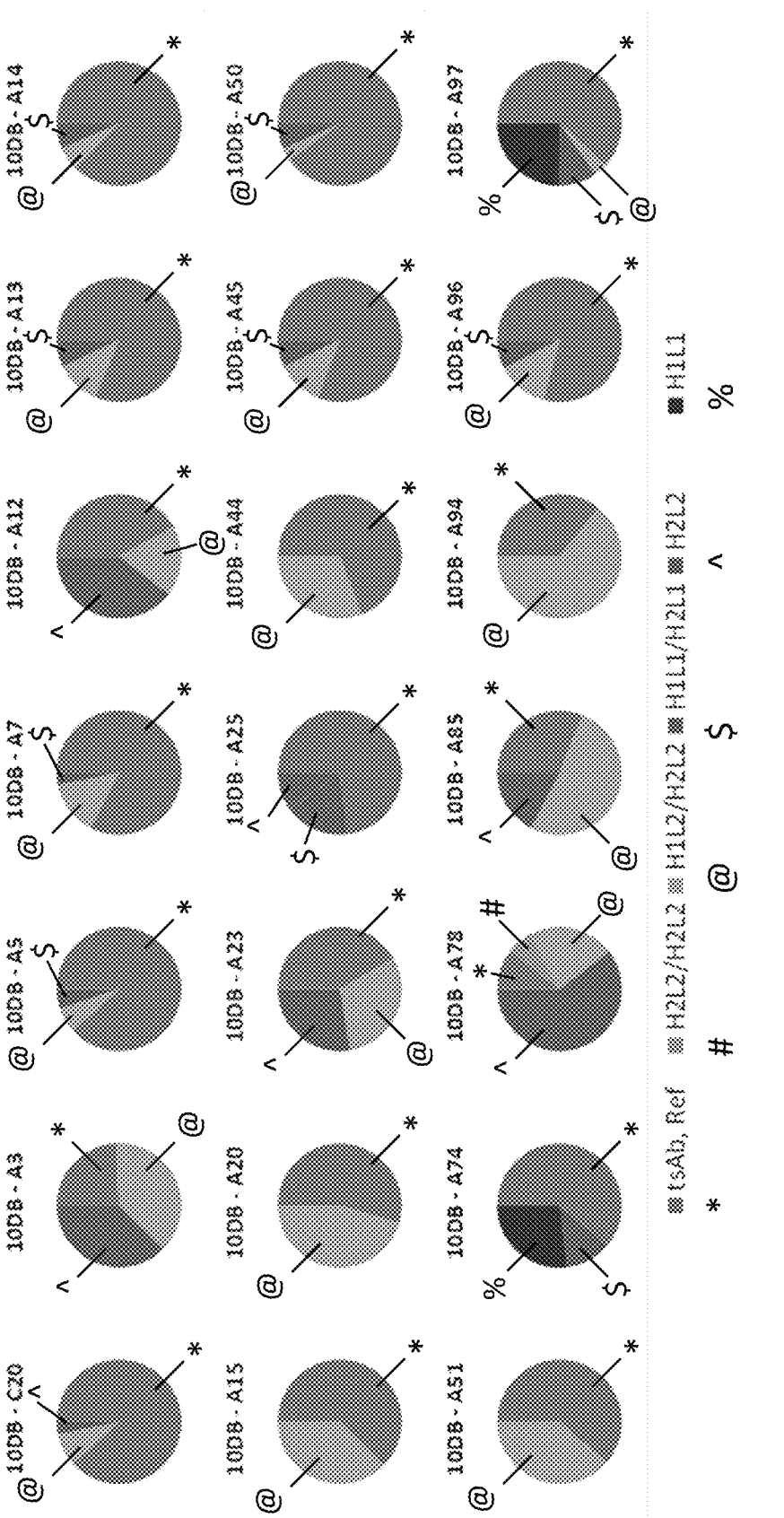
FIG. 3C shows pie charts depicting contributions of mispaired and half antibody impurities, as well as correctly paired species, in randomly selected subset of anti-CD38 trispecific binding protein-producing clones generated by batch culture.

FIG. 3A shows the % purity (i.e., the percentage of the correct mass) in different clones of an anti-CD38 TCE construct grown using batch CHO cell culture. A high degree of variability in purity, ranging from 90% to 10%, was observed among clones. Furthermore, relative levels of mispaired species and half antibodies varied significantly from clone to clone, as shown in FIG. 3C. In addition, aligning purity results with clones' productivity values (FIG. 3B), measured by titer, demonstrates the absence of correlation between the two, meaning highly productive clones can potentially yield a high degree of mispaired and incompletely assembled mAb species.

These results indicate the importance of screening tsAb clones for mispairing levels and using that information in conjunction with productivity and other cell culture parameters for cell line development and selection of the best production clones.

Example 2: Direct Intact MS Analysis of Clarified Harvest

In order to decrease the cost and lead time of the clone screening and streamline the workflow, the denaturing SEC-MS method parameters were optimized to enable intact MS measurement of mAb species directly in the clarified cell culture fluid, generated during cell line development, bypassing any prior purification or sample manipulation.

Intact MS analysis of cell culture fluid is challenged by the complex matrix, especially the presence of nonionic surfactants such as Pluronic F-68, commonly added to the media to protect cells from hydrodynamic damage, which can lead to co-elution and ion suppression during MS analysis. In addition, tsAb species suffer from ion suppression by the overwhelming amount of free CODV (~36 kDa) and Fab (~23 kDa) light chains over-expressed in the harvest as well as tsAbs' inherently low ionization efficiency due to their large size (up to 210 kDa for some mispaired species). Chromatographic separation of proteins from surfactants on reversed phase (RP) stationary phases commonly used for intact protein MS can be quite challenging if not impossible, due to the hydrophobicity of both types of species. Additionally a given RP-LC method exhibits different selectivity behaviors for different tsAb depending on the amino acid sequences and may not be used as a platform method for multiple constructs of tri-specific antibodies.

In this Example, SEC-LC under denaturing condition was successfully employed for size-based separation of antibody species from small molecules and surfactants in clarified cell culture fluids. Liquid chromatography parameters including flow rate, mobile phase modifiers and organic content as well as MS source parameters were optimized for acquisition of high quality MS data on tsAb species in the harvest, comparable to ProA purified material. The optimized denaturing SEC method efficiently separated mAb-related species including tsAb and over-expressed CODV light chain

US 12,618,853 B2

Figure 4A:
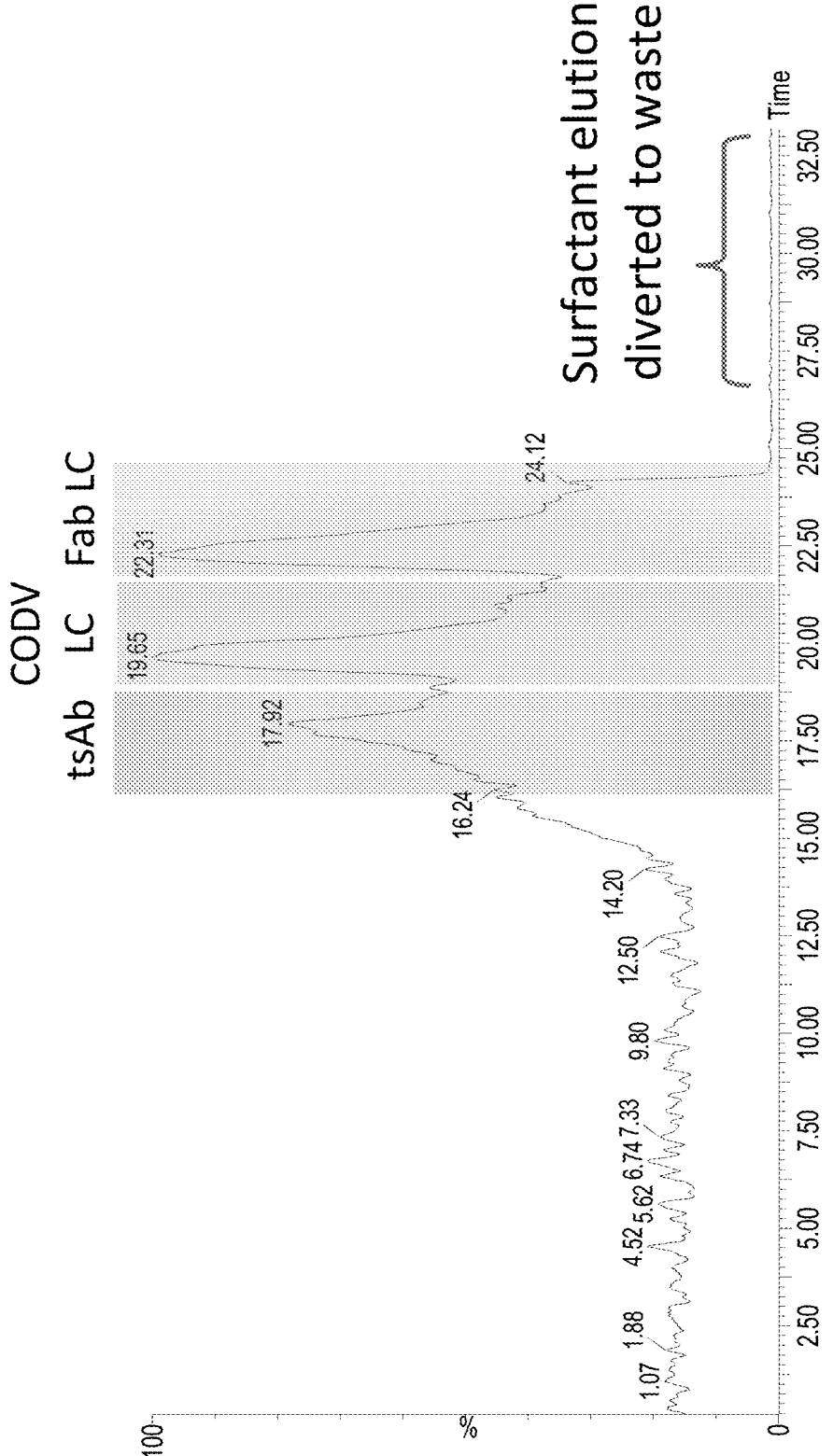
FIGS. 4A-4C show analysis of trispecific binding proteins by SEC-intact MS.
Figure 4B:
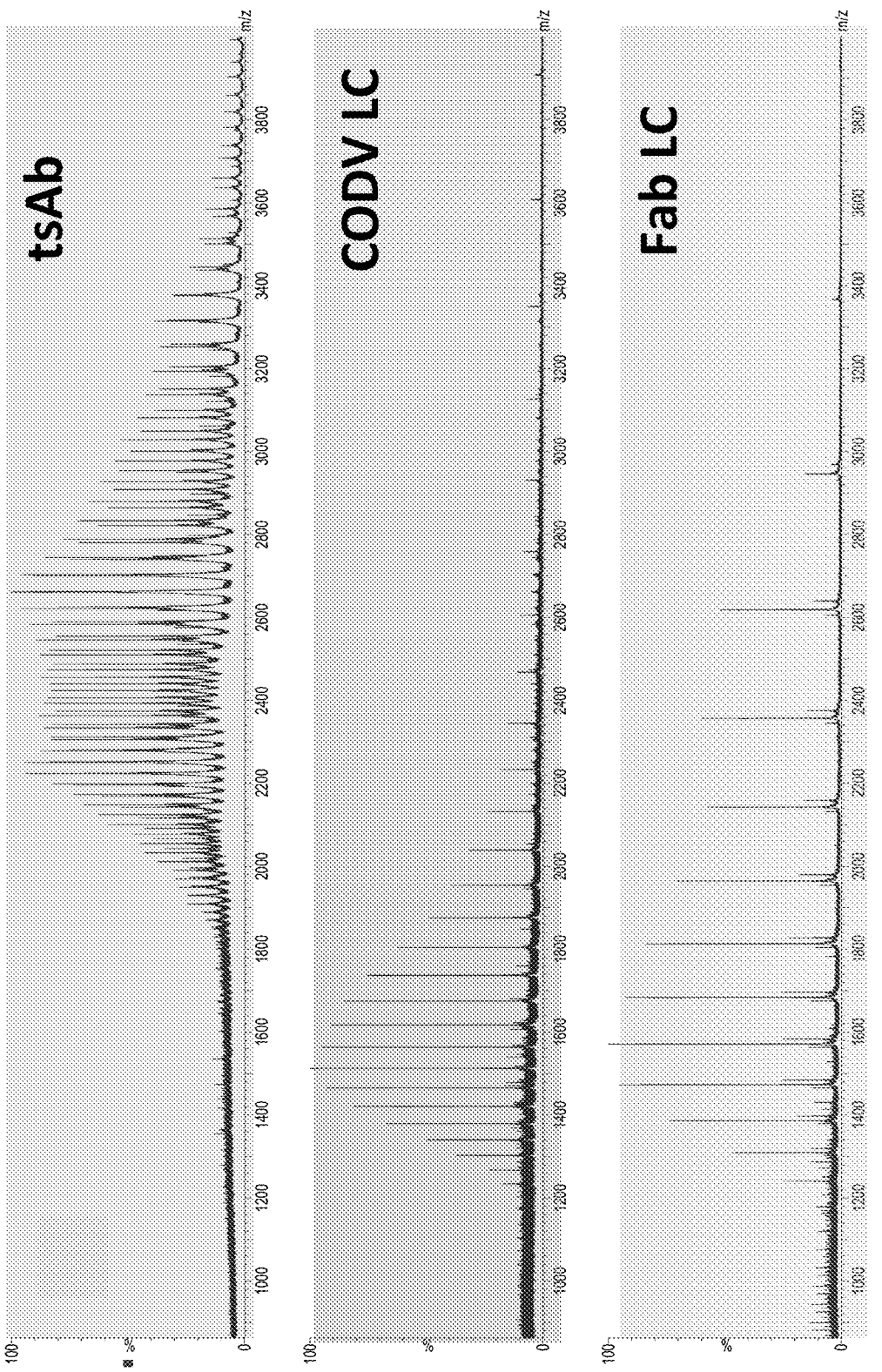

45 and Fab light chain from each other and from surfactant species, as seen in the base peak chromatogram in FIGS. 4A & 4B.

The surfactants elute latest in the chromatogram and the flow is diverted to waste to avoid contamination of MS source (FIG. 4A). This SEC-MS method is a non-product specific platform and allows for rapid and high throughput screening of large number of clones across different tsAb constructs. In addition, the method that has been developed can be applied to other mAb related modalities including Fc-less antibody formats such as scFv2 and Fab fusion proteins (Brinkmann, U. and Kontermann, R. E. *MAbs* 2017, 9 (2), 182-212), which may not be purified using automated ProA purification systems.

Figure 4C:
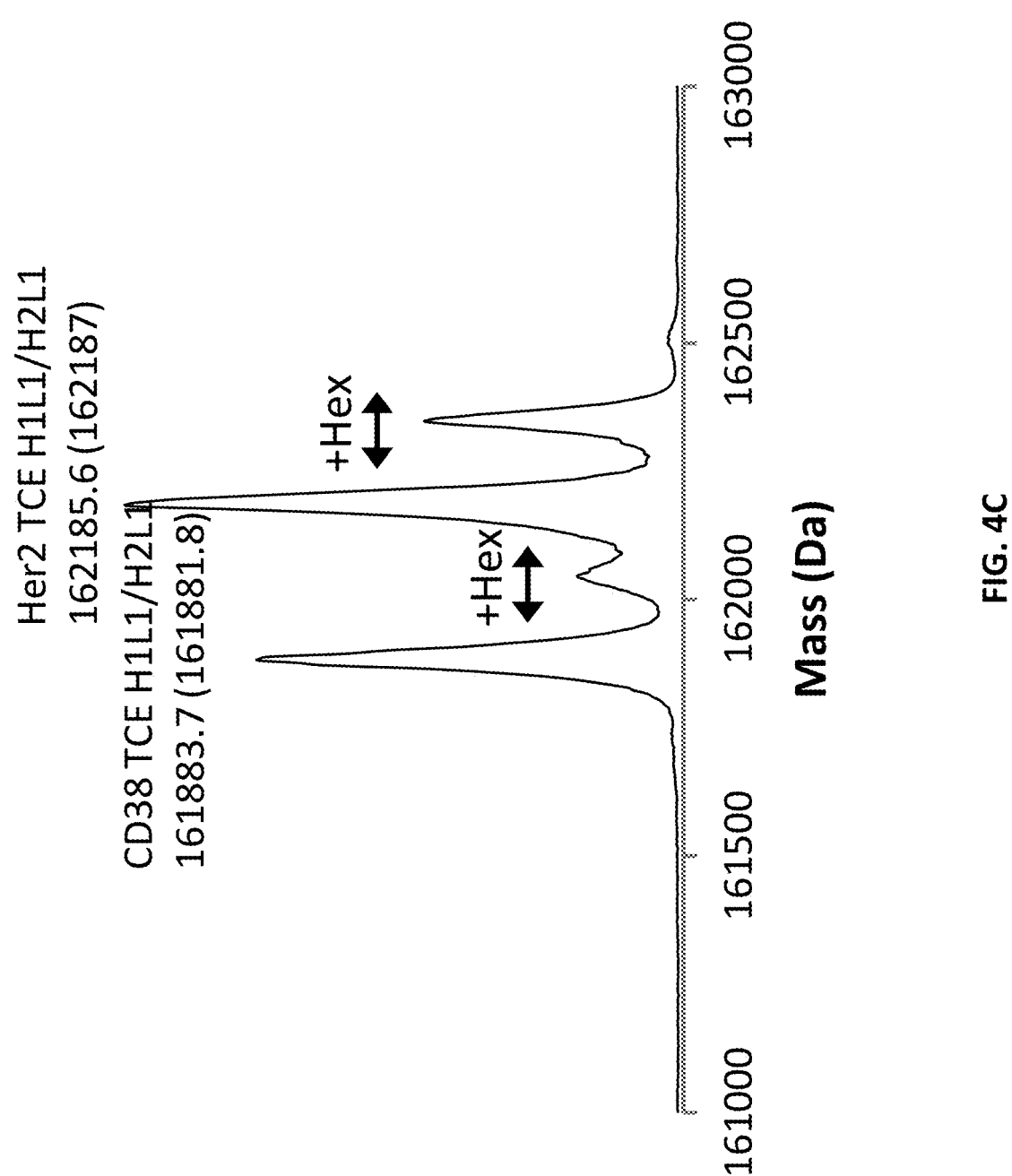

The smallest mass difference between two mispaired species in the anti-CD38 TCE construct is 810 Da and in anti-HER2 TCE construct is 1095 Da, well below the mass resolving power of the method. To demonstrate the capability of the method to resolve mispaired species closer in mass, clarified harvest samples from both constructs were mixed at 1:1 ratio to generate a more complex mixture of mispaired species. Both samples contained H1L1/H2L1 species with a difference in theoretical mass values of ≈302 Da for CD38 TCE and anti-HER2 TCE. As seen in FIG. 4C, online SEC-MS analysis of the harvest fully resolved these two species and their glycoforms, marked by +162 Da mass shifts.

Figure 5A:
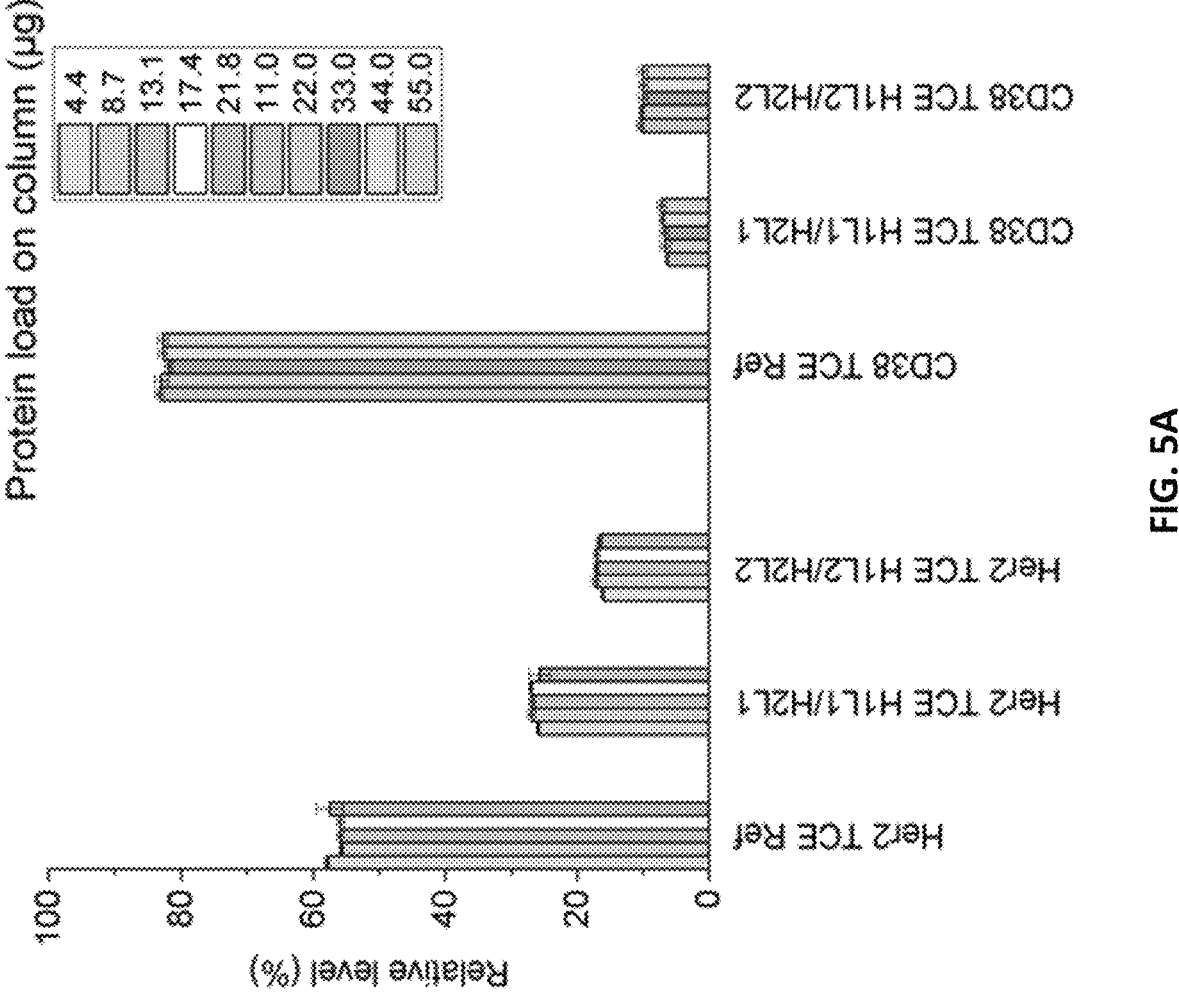
FIG. 5A shows relative quantitation of correctly paired and mispaired species obtained for different column load (μg protein) from 4.4-21.8 μg for anti-HER2 trispecific binding protein and 11.0-55.0 μg for anti-CD38 trispecific binding protein, demonstrating the robustness and reliability of this method for analysis of low and high titer harvest samples. For anti-HER2 trispecific binding protein, column loads are shown as 4.4 μg, 8.7 μg, 13.1 μg, 17.4 μg, and 21.8 μg (left to right). For anti-CD38 trispecific binding protein, column loads are shown as 11.0 μg, 22.0 μg, 33.0 μg, 44.0 μg, and 55.0 μg (left to right).

Next, the repeatability, reliability and robustness of the MS signal were evaluated using clarified harvest fluids of two different tsAb constructs: anti-HER2 TCE anti-CD38 TCE with titer values of 435 and 1100 µg/mL respectively. FIG. 5A shows the relative levels of three different tsAb assemblies are consistent across different column loads achieved by increasing injection volume from 10 to 50 µL. These results demonstrate the robustness and reliability of the MS quantitation over the range of 4-55 µg column loads. Therefore, the online SEC-MS with fixed injection volume of clarified harvest can be used for clones with low and high titers, typically in the range of 100-1100 µg/mL. The repeatability of the method evaluated by triplicate LC-MS analysis at each protein load level across two tsAb constructs in FIGS. 4A-4C returned % RSD values below 10% (Table A).

46

The harvest SEC-MS method was utilized for high throughput screening of 50 anti-HER2 TCE clones. In this study, the correctly assembled molecule (175576 Da) was found to be the major form while light chain mispaired species H1L1/H2L1 (162187 Da) and H1L2/H2L2 (188965 Da) were detected at various levels in all tested samples. No or very low levels of half antibody was detected in the tested clones. Similar to anti-CD38 TCE, no correlation between mispairing levels and clone productivity was observed. (FIGS. 5D & 5E).

Example 3: Effect of Cell Culture Growth Conditions on Chain Mispairing

Two different sets of studies were conducted to investigate the effect of cell growth conditions on chain mispairing and half antibody formation in tsAbs.

In the first study, clones of anti-CD38 TCE were grown under a) batch culture and harvested on day 10 and b) and c) two different growth conditions in ambr® microbioreactor. SEC-Intact MS analysis (ProA purified materials) showed variations in the distribution of mispaired and half antibodies in each clone grown under three different conditions (FIGS. 6C-6E). However clone ranking based on total level of impurities generally remained unchanged regardless of growth condition, as seen in FIG. 6C.

Similar findings were made in the study of the anti-HER2 TCE, where clarified harvest fluid from selected clones grown under batch culture condition (Day 10 harvest) and in ambr® microbioreactor were analyzed the by SEC-LC-Intact MS for their relative mispairing levels. While the distribution of mispaired species in each given clone varies between batch culture and ambr conditions (FIGS. 6F & 6G), clone ranking based on total mispairing was generally similar between the two growth conditions (FIG. 6B). These results underscore the importance and validity of initial clone selection based on mispairing data despite the inevitable changes in process conditions in the later stages of drug development.

It is noteworthy that in both studies, there was a greater variation in the yield of correctly paired tsAb between

TABLE A

Relative levels of mis-paired and reference masses and precision results for triplicate analysis of anti-CD38 TCE and anti-HER2 TCE harvest samples at different column loads.

| tsAb construct | Harvest injection volume (µL) | Column load (µg protein) | Ref. mass Mean | Ref. mass % RSD | H1L1/H2L1 Mean | H1L1/H2L1 % RSD | H1L2/H2L2 Mean | H1L2/H2L2 % RSD |
|---|---|---|---|---|---|---|---|---|
| anti-HER2 TCE | 10 | 4.4 | 57.9 | 0.5 | 26.0 | 0.7 | 16.2 | 1.1 |
| | 20 | 8.7 | 55.7 | 0.4 | 27.0 | 1.8 | 17.3 | 2.8 |
| | 30 | 13.1 | 55.9 | 0.8 | 26.9 | 1.7 | 17.2 | 2.0 |
| | 40 | 17.4 | 55.8 | 1.0 | 27.0 | 1.0 | 17.1 | 2.6 |
| | 50 | 21.8 | 57.5 | 3.5 | 25.8 | 6.3 | 16.7 | 2.3 |
| anti-CD38 TCE | 10 | 11.0 | 83.3 | 0.7 | 6.3 | 2.6 | 10.4 | 4.3 |
| | 20 | 22.0 | 83.0 | 1.2 | 6.6 | 10.4 | 10.2 | 3.1 |
| | 30 | 33.0 | 81.9 | 0.7 | 6.8 | 9.3 | 10.0 | 6.4 |
| | 40 | 44.0 | 82.7 | 0.7 | 7.0 | 6.0 | 10.0 | 6.2 |
| | 50 | 55.0 | 82.8 | 0.9 | 7.2 | 8.8 | 10.0 | 6.5 |

60

Figure 5B:
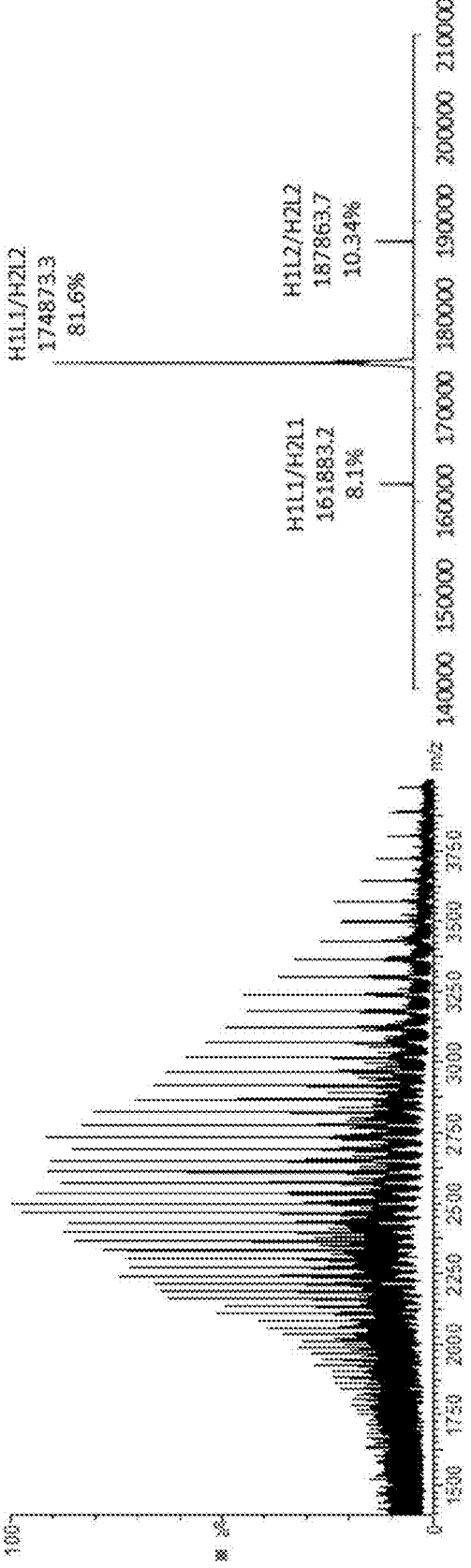
FIGS. 5B & 5C show raw and deconvoluted mass spectra obtained by SEC-LC-MS analysis of clarified harvest (FIG. 5B) and ProA purified (FIG. 5C) anti-CD38 trispecific binding protein showing comparability of the two methods. Annotations on the deconvoluted spectra show the experimental masses and % intensities of each species.
Figure 5C:
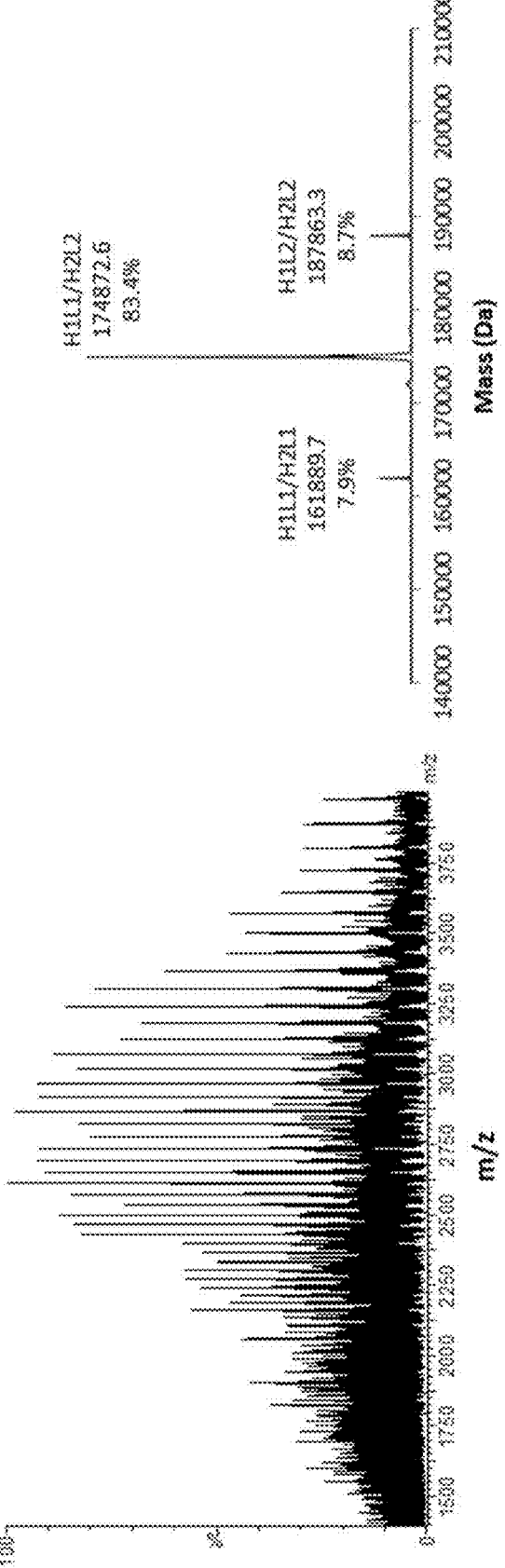
Figure 5D:
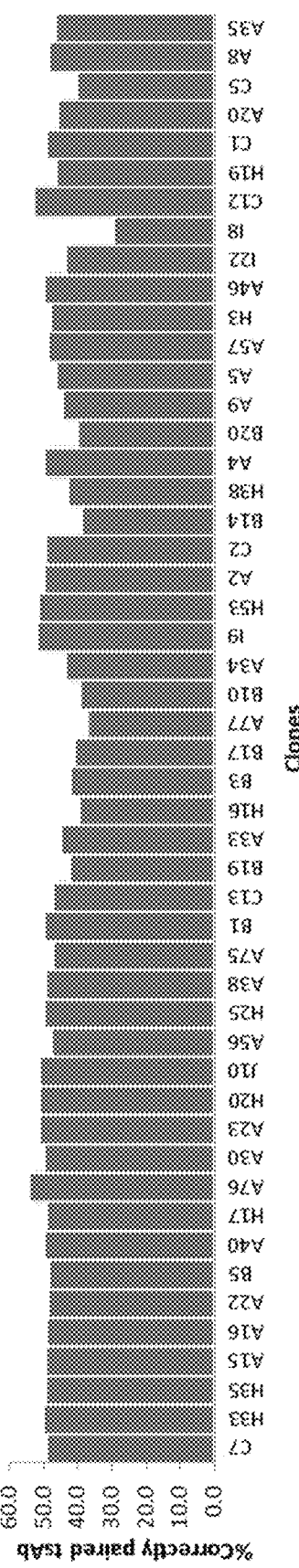
FIGS. 5D & 5E show ranking of anti-HER2 trispecific binding protein-producing clones based on percentage of correct tsAb mass (purity) (FIG. 5D) and productivity measured by titer for the same clones (FIG. 5E).
Figure 5E:
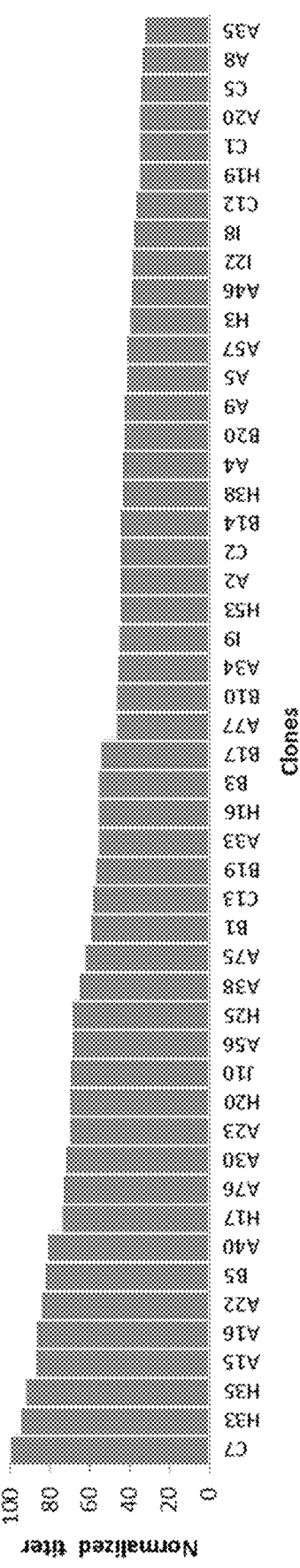
Figure 6A:
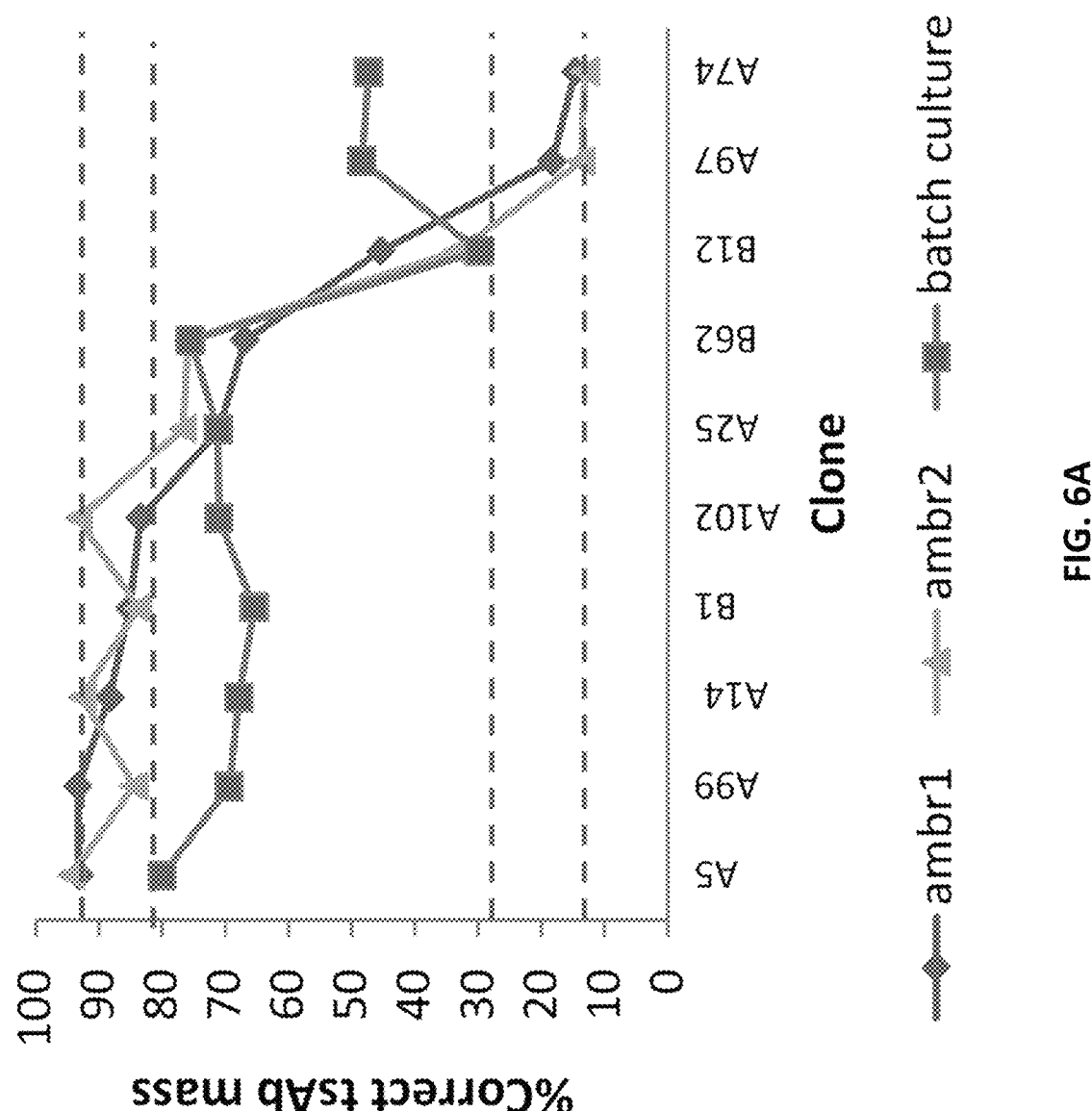
FIGS. 6A & 6B show yield of correct tsAb mass in different clones of anti-CD38 trispecific binding protein (FIG. 6A) and anti-HER2 trispecific binding protein (FIG. 6B) grown under different cell culture conditions (ambr or batch, as indicated).
Figure 6B:
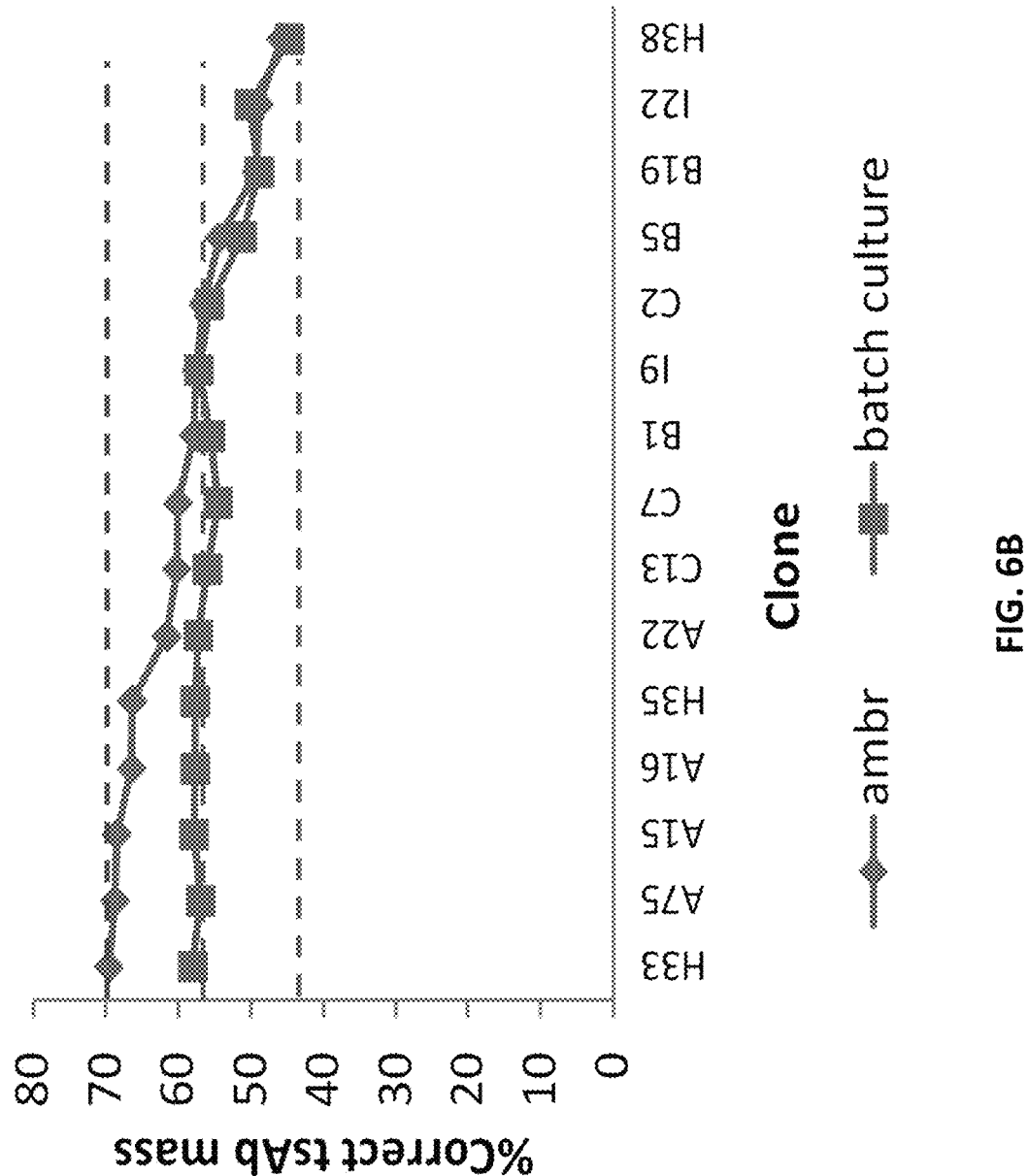
Figure 6C:
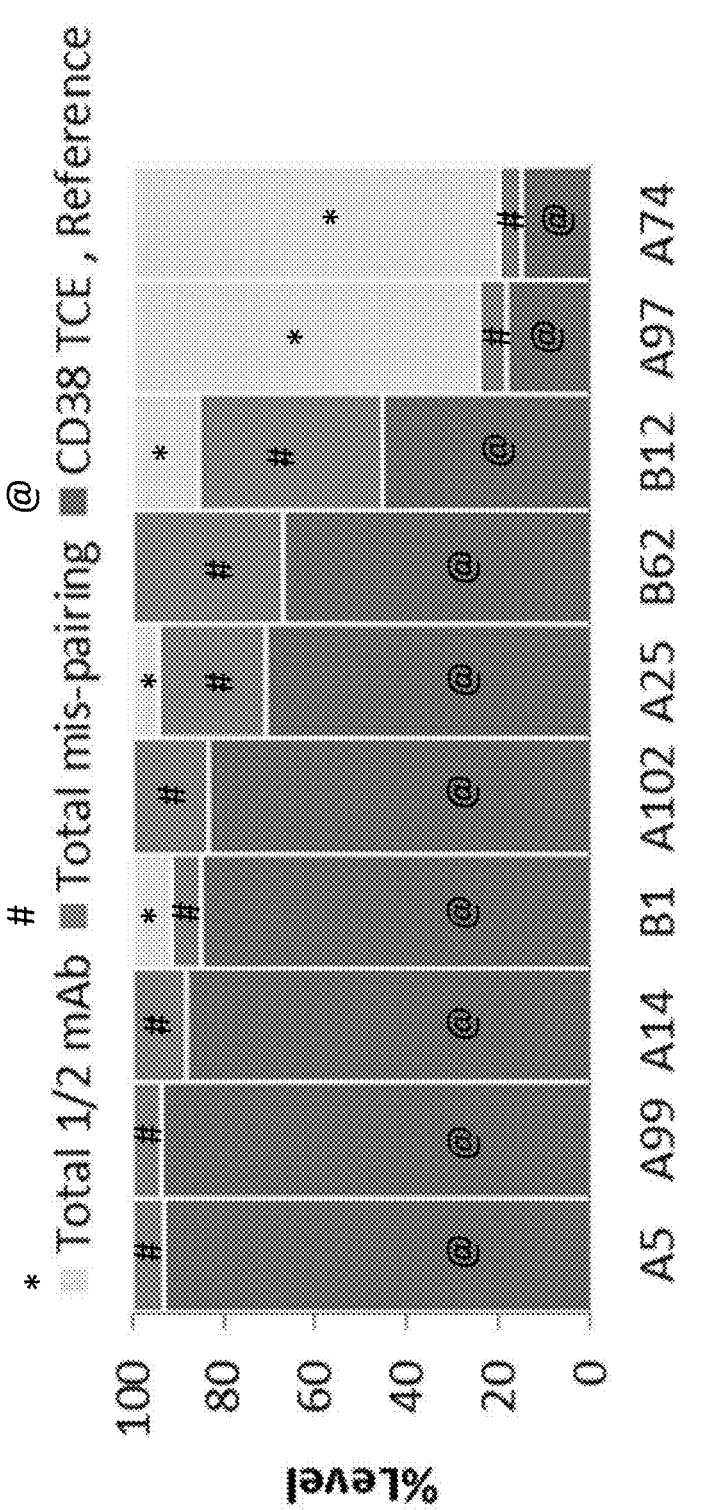
FIGS. 6C-6E show the effects of different growth conditions on chain mispairing and half antibody levels in anti-CD38 TCE clones grown under two different ambr conditions (FIGS. 6C & 6D) and batch culture conditions (FIG. 6E).
Figure 6D:
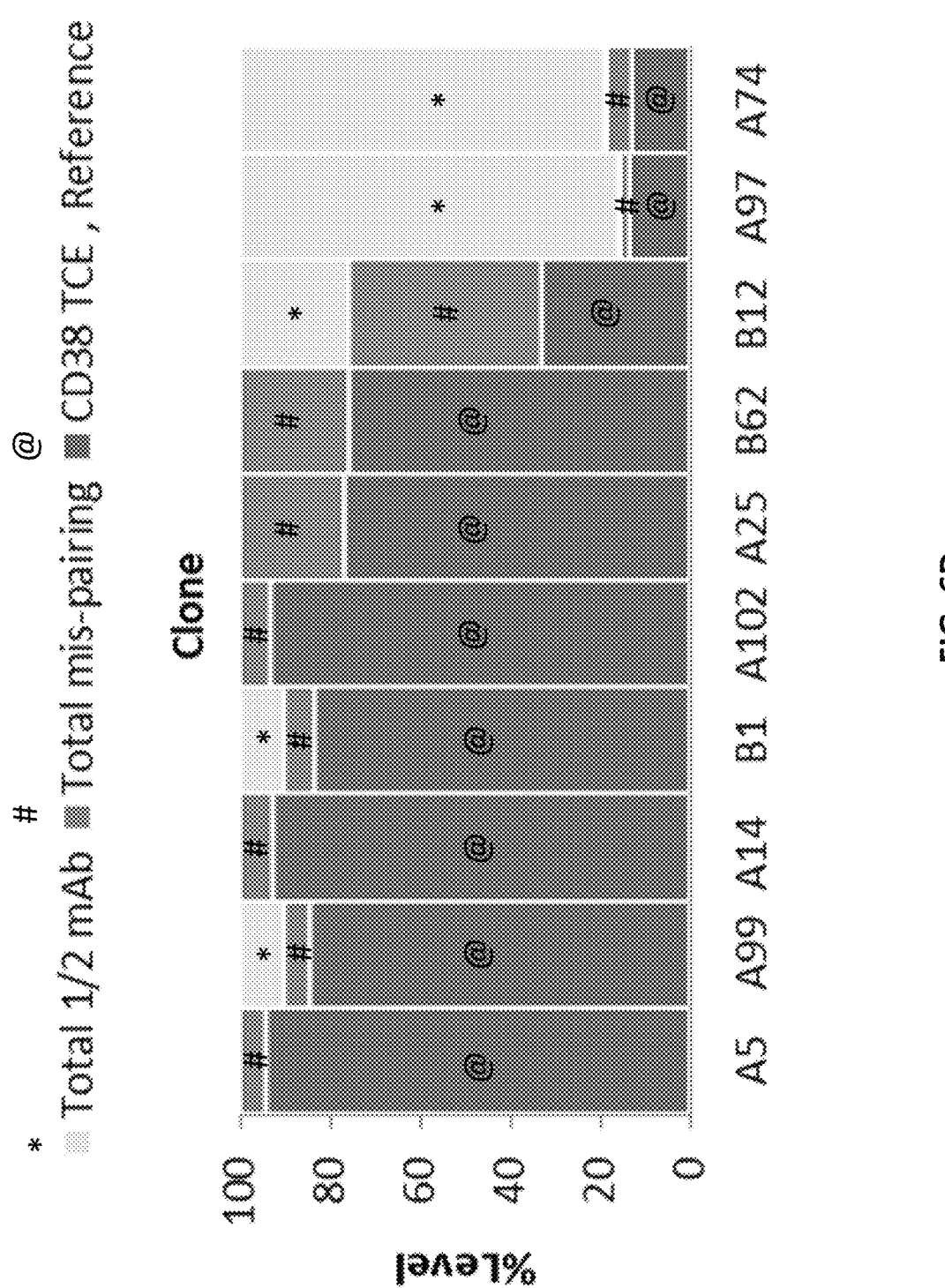
Figure 6E:
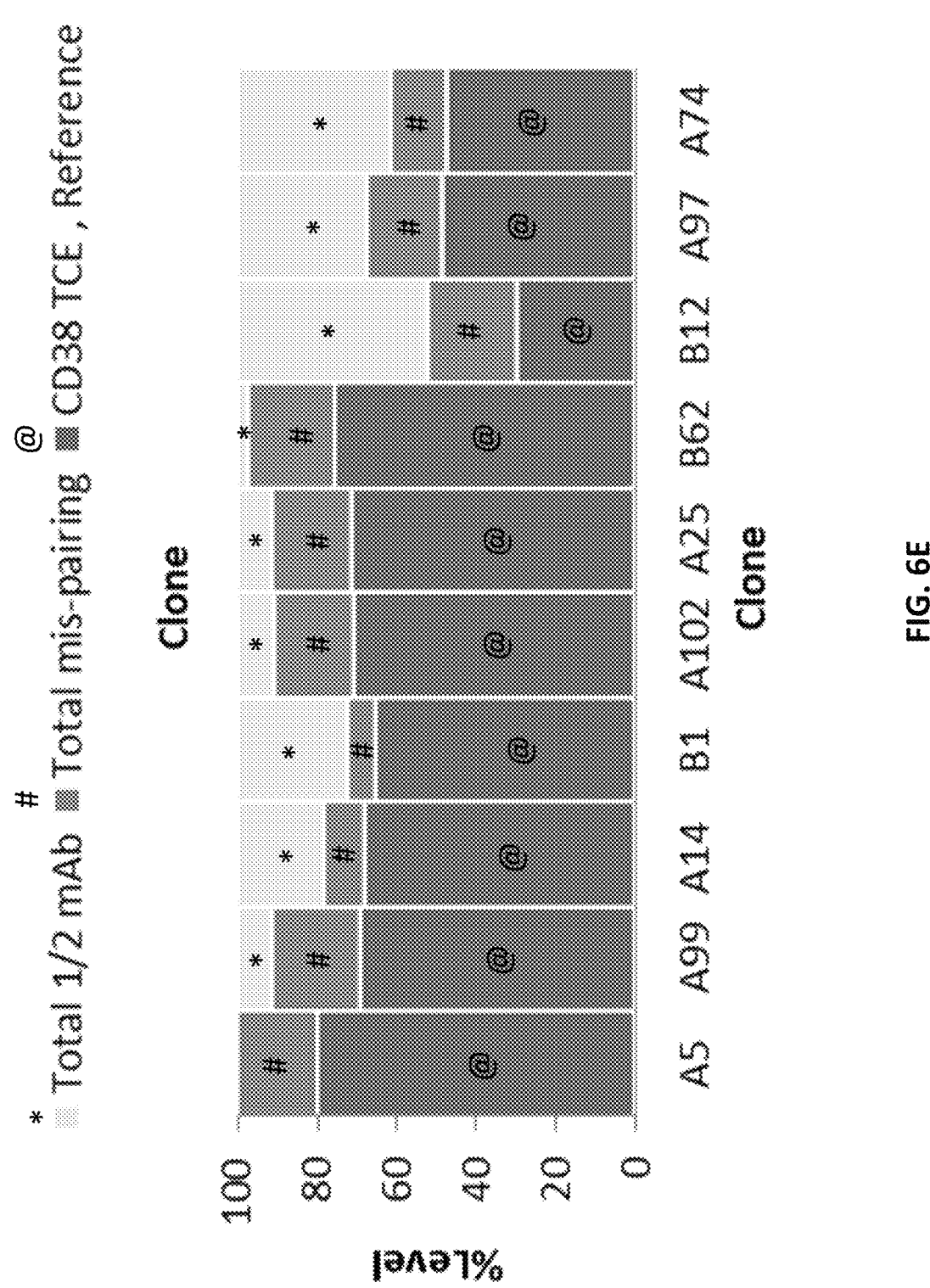
Figure 6F:
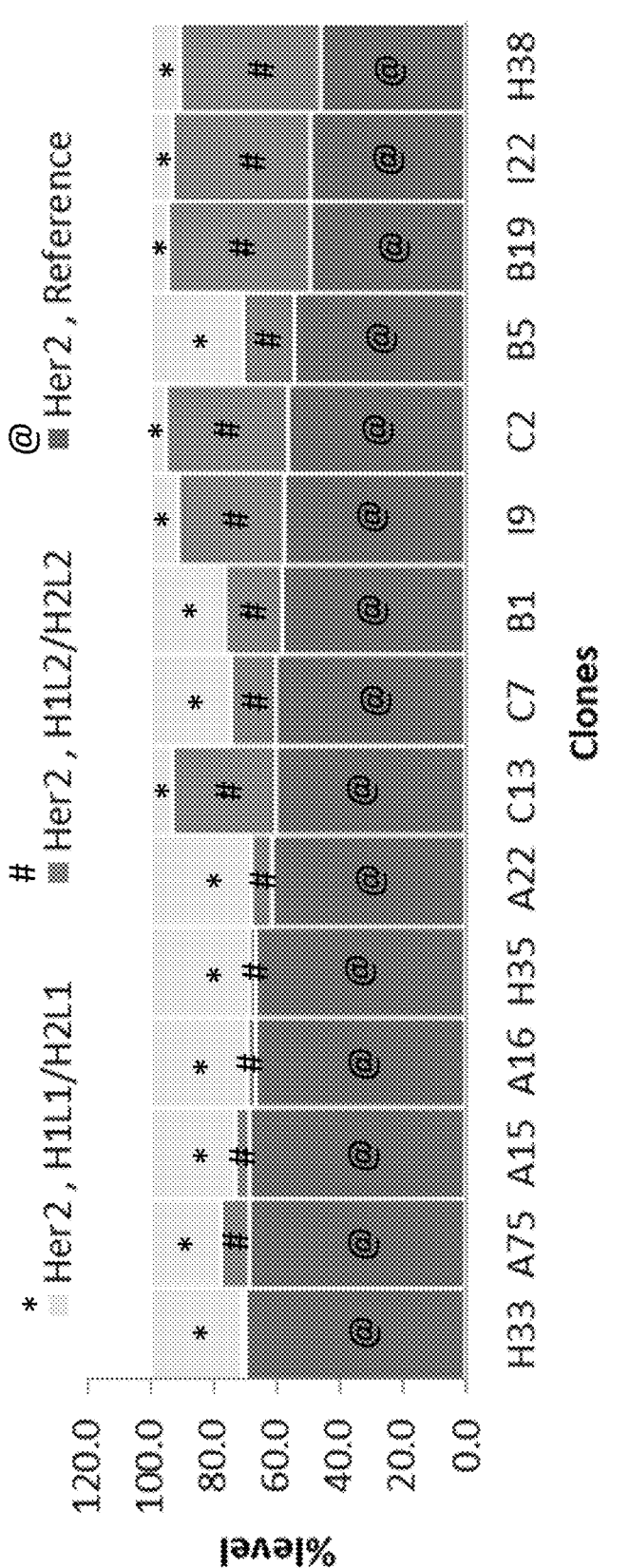
FIGS. 6F & 6G show the effects of different growth conditions on chain mispairing levels in anti-HER2 TCE clones grown under ambr (FIG. 6F) or batch (FIG. 6G) culture conditions.
Figure 6G:
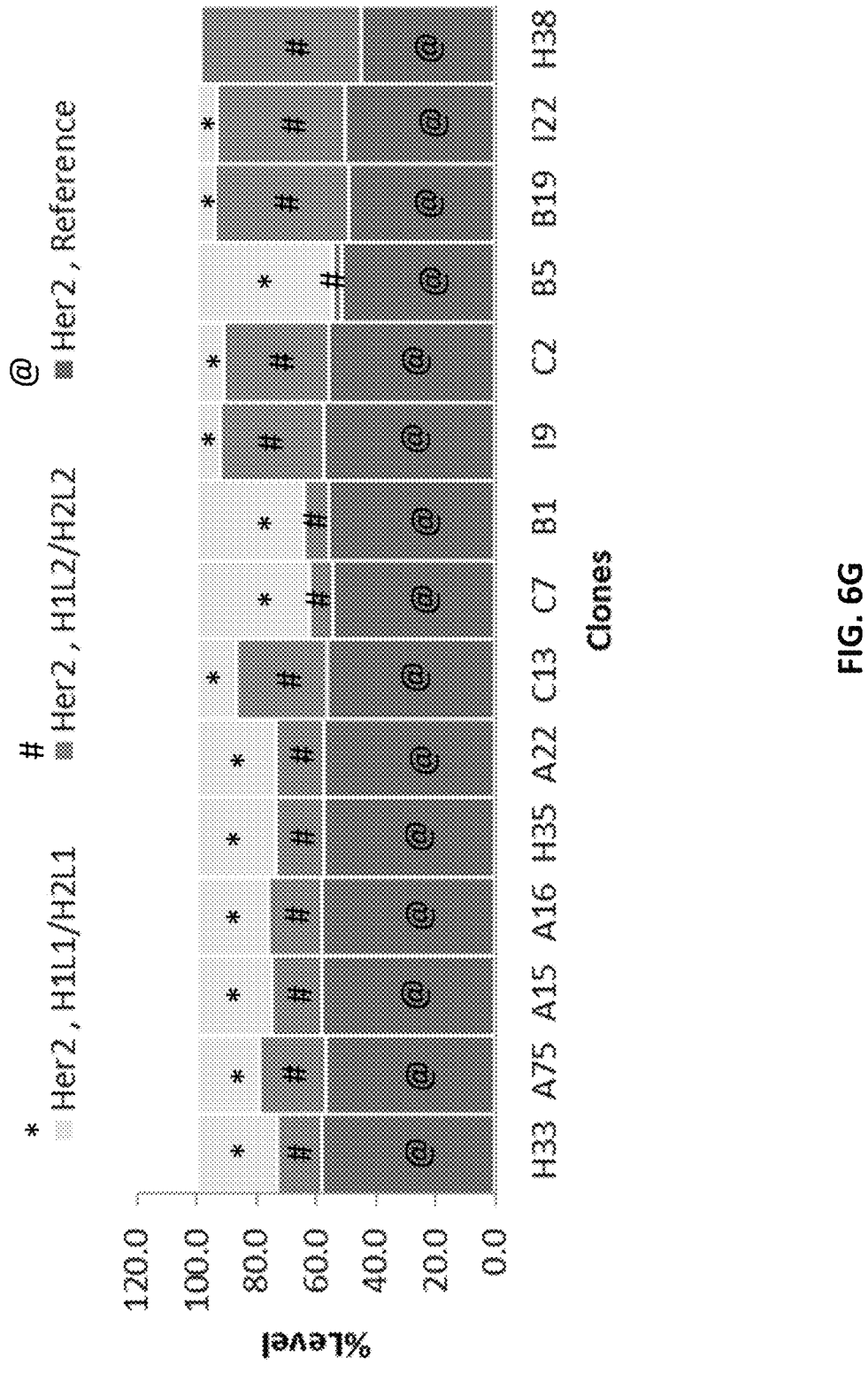

In addition, comparing the results of mispairing quantitation obtained by SEC-LC-Intact MS analysis of clarified harvest and ProA purified materials showed close agreement between the two methods, further confirming the suitability of direct intact MS analysis of harvest for mispairing determination (FIGS. 5B & 5C).

clones grown in ambr® compared to batch culture; marked by % Purity ranges of 10-90% vs 47-80% in CD38 TCE and 46-70% vs 45-58% for anti-HER2 TCE (FIGS. 6A & 6B). Interestingly in both cases, the top clones seemed to perform better, suggested by 10-20% higher purity, in ambr bioreactor than batch culture.

Conclusions

Figure 7:
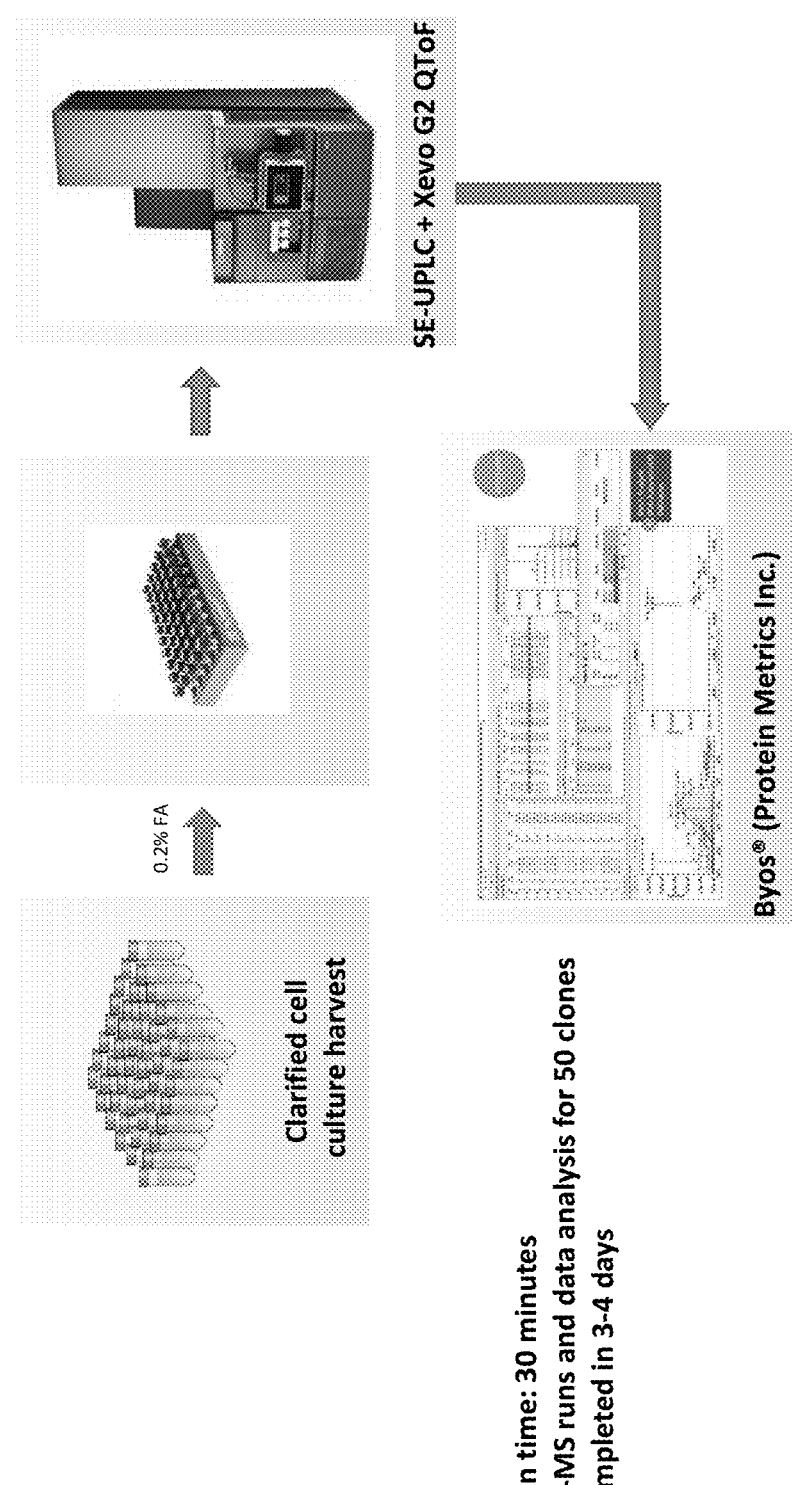
FIG. 7 illustrates an exemplary workflow for high-throughput, intact MS, in accordance with some embodiments. In addition to the high-throughput capability, additional advantages include: (1) no need for protein A purification, saving time and cost; (2) more direct insights into cell line performance by providing information on potential wasted biomass on free chains, half antibodies, and other subspecies that may not pass protein A purification; and (3) applicability to Fc-less modalities, such as Fabs, scFvs, and other antibody fragments.

Mis-assembled species are commonly occurring product-related impurities during manufacturing of multi-specific antibodies that lead to decreased production yield and necessitate costly purification steps as well as robust analytical methods for early stage monitoring. In the above Examples, a high throughput analytical platform based on denaturing SEC-LC-Intact MS for identification and relative quantitation of chain mispairing and other IgG-related species was described. The developed method allows for intact MS analysis of mAb-related species directly in the clarified harvest bypassing time consuming and expensive ProA purification and buffer exchange steps (FIG. 7). Intact MS analysis of two different tsAb constructs; anti-CD38 TCE and anti-HER2 TCE from different clones of CHO cells showed variations in the level of correctly paired tsAb yield from clone to clone with no apparent correlation between clone's productivity (titer) and mispairing. In addition, different growth conditions may affect types and distribution of the impurities but not the quality ranking of the clones, confirming validity of initial clone selection based on mispairing data despite the inevitable changes in process conditions in the later stages of drug development.

Example 4: Intact Mass Analysis of Harvest for Trispecific Binding Proteins

Intact protein mass spectrometry has been used for identification and relative quantitation of biotherapeutics, their variants and product-related impurities by others in the past. Several different intact protein MS approaches based on reversed phase separation or size exclusion LC for denaturing and native MS analysis have been reported (Xu, L. et al. (2017) *Science* 358:85-90; Ridgway, J. B. et al. (1996) *Protein Eng.* 9:617-621; Wang, C. et al. (2018) *MAbs* 10:1226-1235; Schaefer, W. et al. (2016) *MAbs* 8:49-55). These approaches require the antibody be purified typically through Protein A affinity, prior to LC-MS analysis.

The Examples above describe a high throughput analytical platform consisting of denaturing size exclusion liquid chromatography (SEC) coupled with QToF mass spectrometry for intact MS analysis of chain mispairing in trispecific antibodies (tsAb). See also Tousi, F. et al. (2020) *Anal. Chem.* 92:2764-2769. This intact mass method can be performed directly on the clarified harvest fluid with no prior purification or sample preparation. This analytical platform has enabled screenings of large numbers of CHO (Chinese Hamster Ovary) cell clones expressing different tsAb constructs, for their levels of mispaired species and half antibody. Results from this intact mass analysis method, particularly early in development, facilitate the selection of CHO clones that produce tsAbs of acceptable product quality.

Examples 4 and 5 describe applications of the same analytical method to the clone selection for different mAb-related constructs: an anti-HIV\CD28\CD3 trispecific antibody (Example 4), and a cysteine engineered monoclonal antibody (mAb) (Example 5).

Materials and Methods

Size-Exclusion Chromatography (SEC)

The size exclusion LC separation was performed using a UPLC BEH SEC Column, 1.7 µm, 200 Å, 4.6×300 mm controlled by an Acquity UPLC H-Class (Waters Corp., Milford, MA, United States). A solution of 0.05% formic acid (FA) and 0.05% TFA in 30:70 acetonitrile:water at the flow rate of 0.1 mL/min (from 0 to 25 minutes) and 0.4 ml/min (from 25 to 33 minutes), in isocratic mode was used as the mobile phase. The volume of 50 µL of clarified harvest was directly injected to the LC-MS system using an Acquity autosampler set to 4° C. Both FA and TFA were LC-MS grade from Sigma (St. Louis, MO, United States). The LC-MS water and acetonitrile were from Thermo Fisher Scientific (Waltham, MA, United States).

Mass Spectrometry (MS)

The LC was coupled to a Xevo G2 (or G2XS) QToF mass spectrometer (Waters Corp., Milford, MA, United States) for online intact MS data acquisition in sensitivity mode and in the m/z range of 500-4000. Electrospray ionization (ESI) parameters for Xevo G2 instrument included: 3 kV capillary voltage, 40 V sampling cone voltage, 2.5 V extraction cone voltage, 150° C. source temperature, 500° C. desolvation temperature, 50 L/hr cone gas flow, 800 L/hr desolvation gas flow and 6 V collision energy. The ESI parameters for Xevo G2XS were as follows: 3 kV capillary voltage, 200 V sampling cone voltage, 150° C. source temperature, 150 source offset, 250° C. desolvation temperature, 50 L/hr cone gas flow, 800 L/hr desolvation gas flow and 6 V collision energy.

Data Analysis

The acquired LC-MS raw files were batch-processed using Byos® (Protein Metrics Inc.) for deconvolution, annotation and relative quantitation.

Results

Figure 8A:
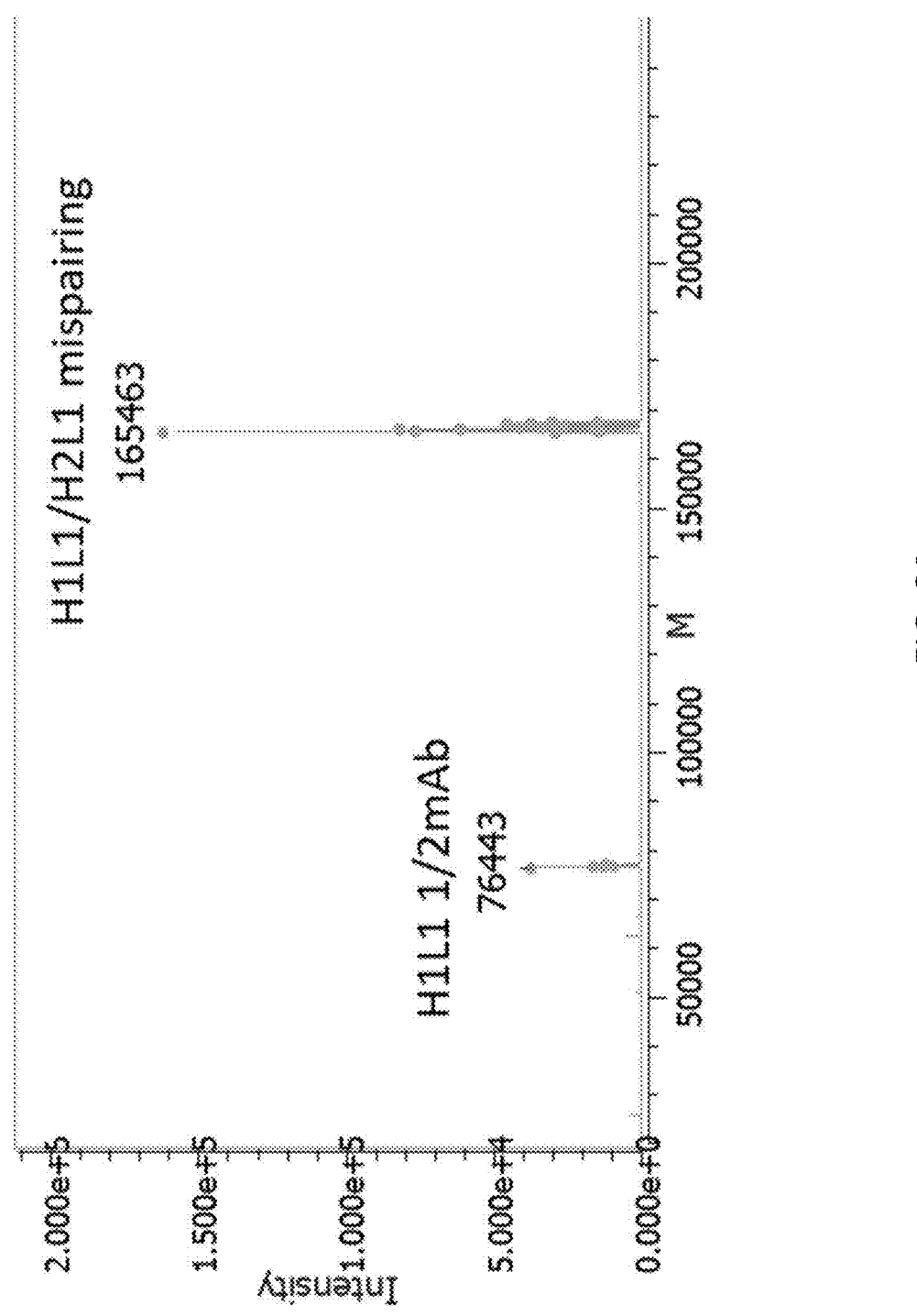
FIGS. 8A & 8B show the deconvoluted intact mass spectra obtained for anti-HIV\CD28\CD3 trispecific antibody-producing cell clones with the highest and lowest levels of chain mispairing, respectively.
Figure 8B:
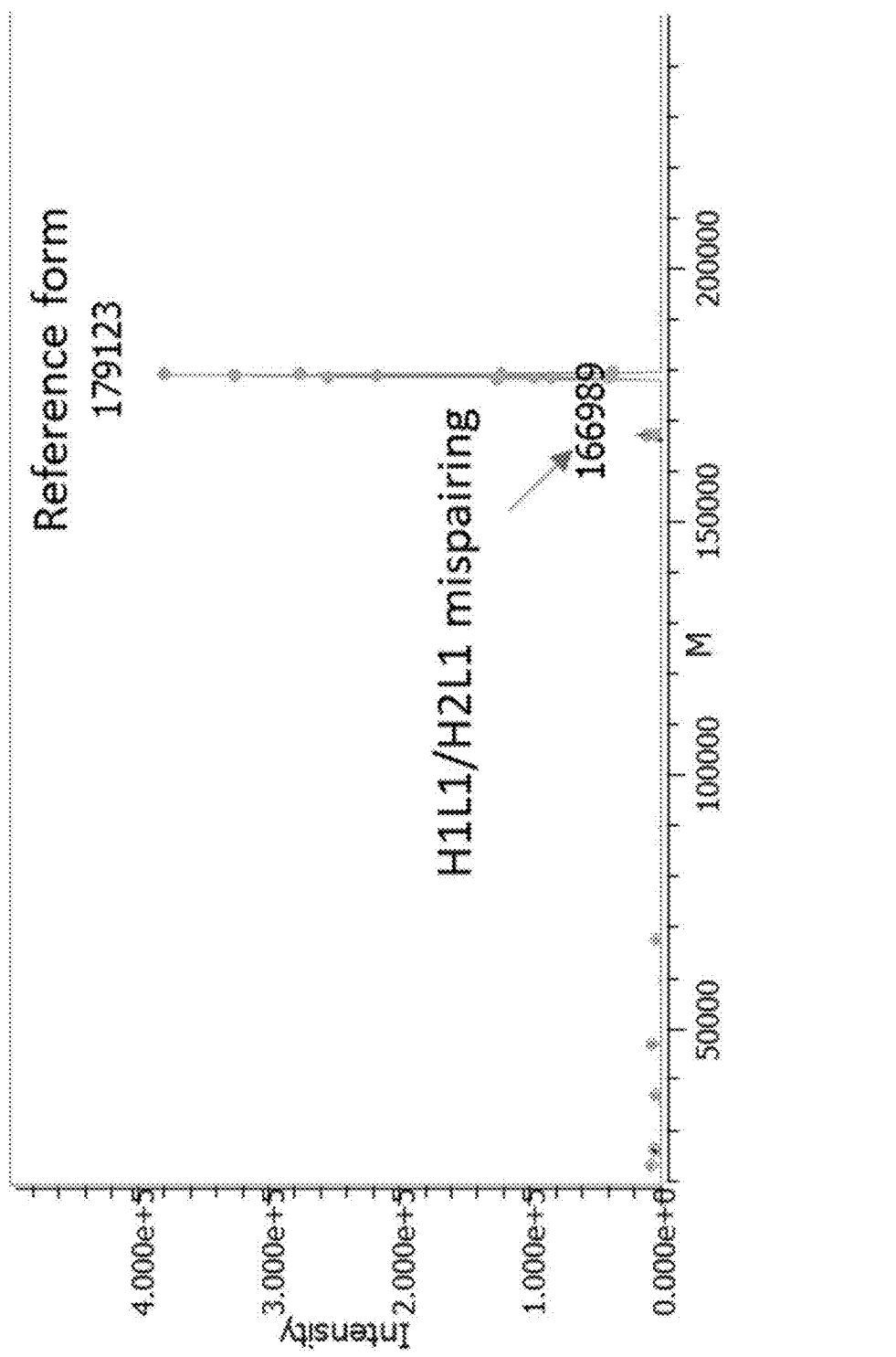

Clarified cell culture harvest samples from 50 clones of CHO cells expressing anti-HIV\CD28\CD3 tsAb were analyzed using the above described denaturing SEC-Intact MS method. Upon analyzing the acquired MS .raw files, high degree of variability in levels of mispairing (%) was observed among the tested clones, ranging from as low as 1% to 100% mispairing. H1L1/H2L1 (165-167 kDa) was the dominant mis-paired species. Small number of clones contained H1L2/H2L2 mis-paired form. H2L2/H2L2 homodimer was detected in a few clones. Half antibodies (H1L1 and H2L2) were present in some clones, but at low levels. Unlike trispecific antibodies tested before, no significant amount of H1L2/H2L2 type of mispairing was detected in HIV TCE clones. FIGS. 8A & 8B show the deconvoluted intact mass spectra for anti-HIV\CD28\CD3 clones with the highest and lowest levels of chain mispairing respectively.

Figure 9A:
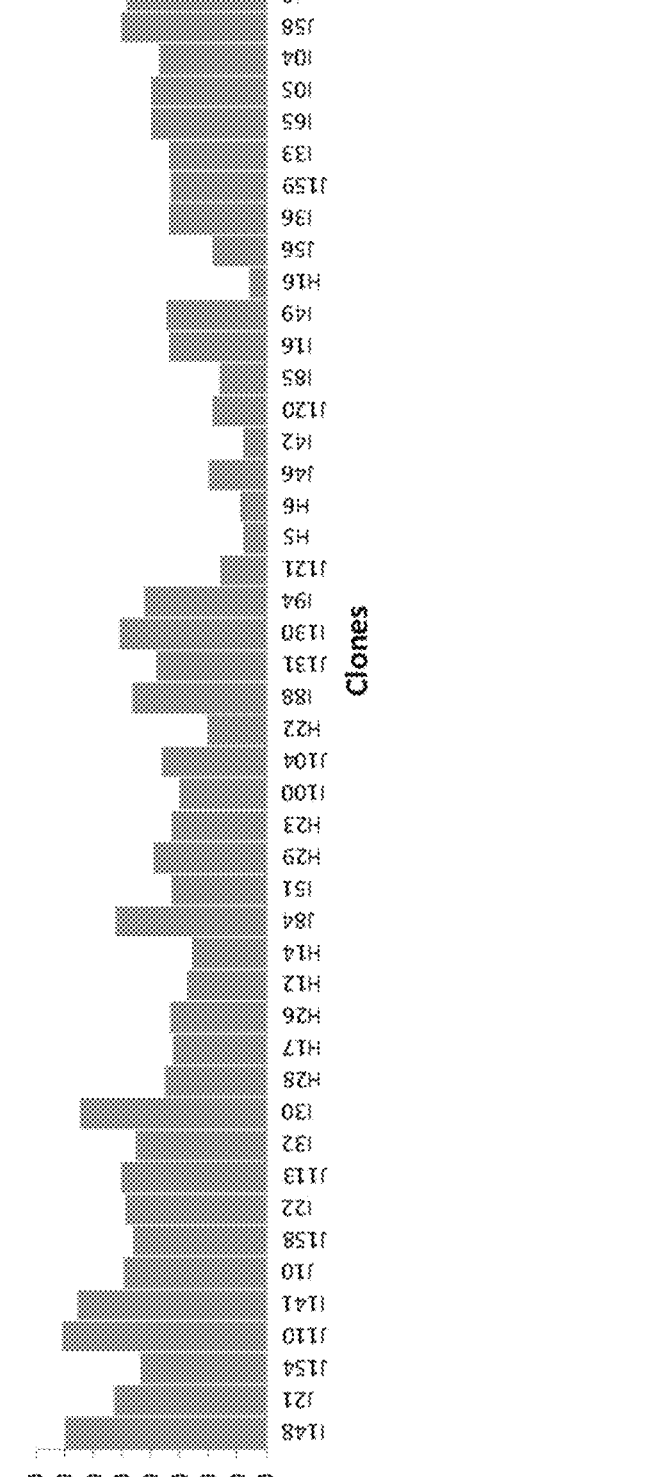
FIGS. 9A & 9B show productivity (assessed by titer, μg/mL.
Figure 9B:
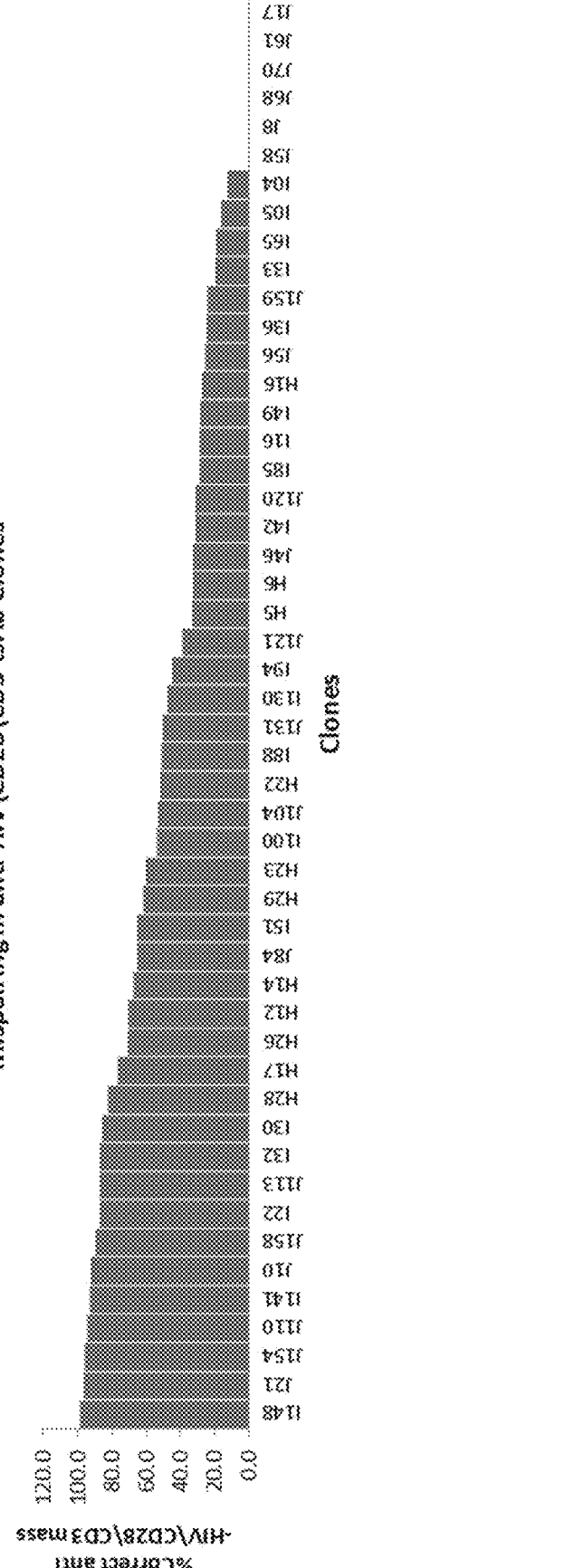

FIGS. 9A & 9B show the clones' productivity measured by protein A titer and relative levels of correct mass for 50 cell clones producing anti-HIV\CD28\CD3 trispecific grown under batch culture conditions during clone selection step as part of the cell line development. The results of mispairing analysis in conjunction with the productivity data allowed for selection of the clones with highest titer as well as lowest levels of chain mispairing. Interestingly, several clones with relatively high productivities showed 0% of correctly paired tsAb, as seen in the right end of the column graphs in FIG. 9B.

Figure 10A:
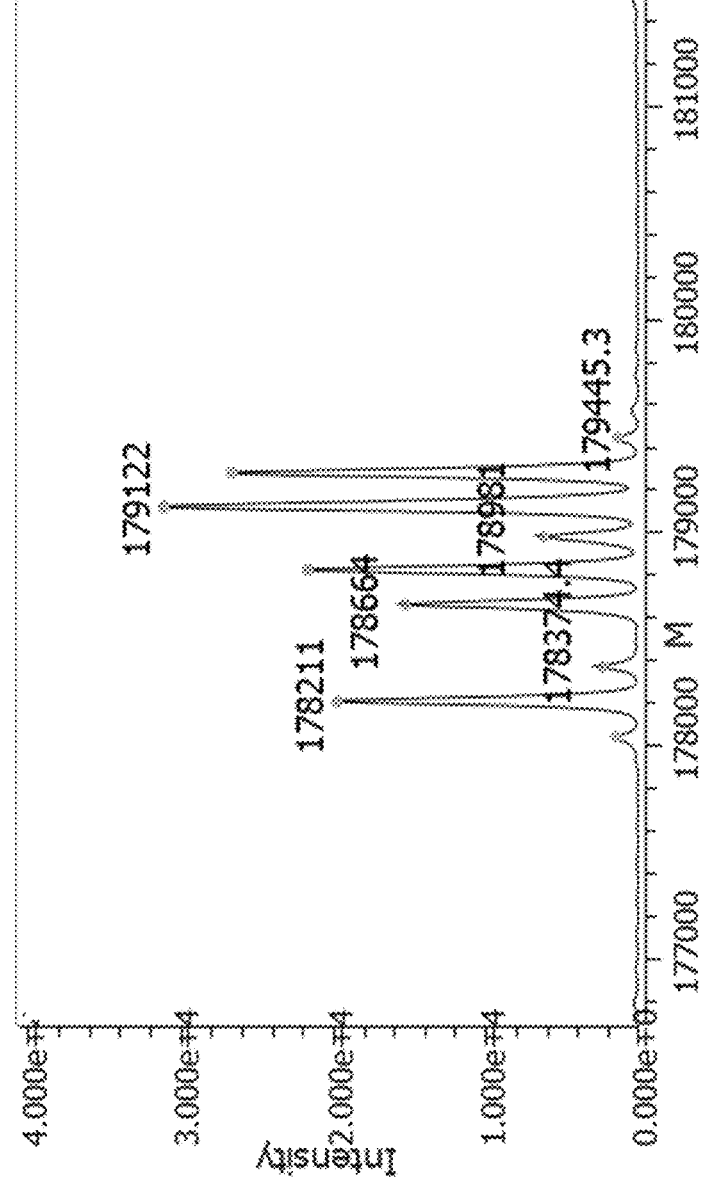
FIGS. 10A & 10B show the detailed glycan profiles obtained for the reference mass (H1L1/H2L2) in a selected clone producing anti-HIV\CD28\CD3 trispecific antibody. The clone was cultured under two different conditions: in a spin tube (batch condition.
Figure 10B:
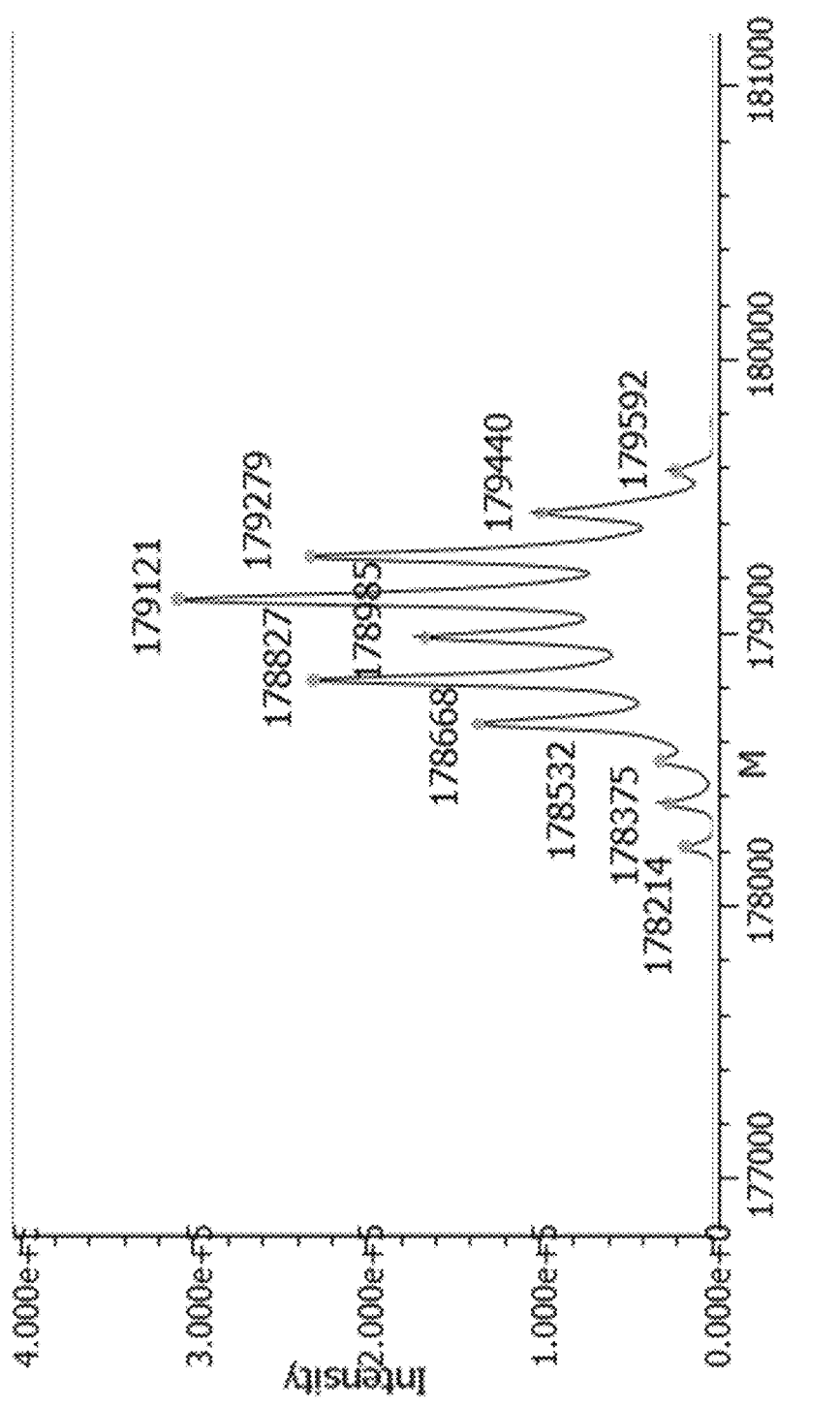

Superb chromatographic separation combined with utilizing a highly sensitive mass spectrometer allowed unraveling of the extremely heterogenous glycan profile at the intact level, due to the presence of sialylated N-glycans on the Fab LC in addition to the usual heavy chain Fc N-glycans. This allows for quickly monitoring N-glycosylation profiles of the clones without the need to perform more elaborate glycan analysis using typically labor-intensive and time-consuming methods. As an example, FIGS. 10A & 10B show the detailed glycan profile for the reference mass (H1L1/H2L2) in a selected clone producing anti-HIV\CD28\CD3 cultured under two different conditions:

1-in a spin tube (batch condition) and 2-in an ambr15 bioreactor (fed-batch condition) respectively, showing the shift towards more galactosylated and sialylated N-glycans evident from the shift towards higher mass values. Due to the extreme glycan heterogeneity added by the light chain glycosylation, the molecular weight of the reference form (H1L1/H2L2) and H1L1/H2L1 mispaired form span over the range of 1000 Da and 2000 Da respectively. The glycoform assignment for the intact anti-HIV\CD28\CD3 reference form is detailed in Table 1.

TABLE 1

| Glycoform assignment observed for trispecific antibody. | | | |
| --- | --- | --- | --- |
| Observed mass (Da) | Theoretical mass (Da) | Δmass (Da) | ID |
| 178214 | 178210 | 4 | H1L1/H2L2 (G0F/G0F/G0) |
| 178375 | 178372 | 3 | +Gal |
| 178532 | 178534 | −2 | +Gal |
| 178668 | 178663 | 5 | 178372 Da + NeuAc |
| 178827 | 178825 | 2 | +Gal |
| 178985 | 178987 | −2 | +Gal |
| 179121 | 179116 | 5 | 178827Da + NeuAc |
| 179279 | 179278 | 1 | +Gal |
| 179440 | 179440 | 0 | +Gal |
| 179592 | 179586 | 6 | +Fuc |

Example 5: Intact Mass Analysis of Harvest for Cysteine-Engineered Antibody

This product is a thiomAb, i.e., an antibody comprising an additional cysteine residue engineered into its Fc region useful, e.g., for conjugation of a compound (e.g., a cytotoxic drug to form an antibody drug conjugate). This additional cysteine is unpaired (free) i.e. not engaged in disulfide bonds with other cysteines in the mAb molecule. Previous work had shown that this additional cysteine (Cys293) can form unwanted disulfide bonds with nearby cysteine residues, otherwise known as "disulfide bond scrambling," potentially leading to structural instability of the antibody. Uncontrolled sulfhydryl chemistry may also pose significant manufacturability risk during processing to form the ADC leading to undesired drug conjugation profile. To avoid these risks, it is imperative to have the free cysteine capped with disulfide linked modification such as cysteinylation and glutathionylation by adjusting cell culture conditions. These modifications can be selectively reduced to generate a free cysteine prior to the drug conjugation step.

Figure 11A:
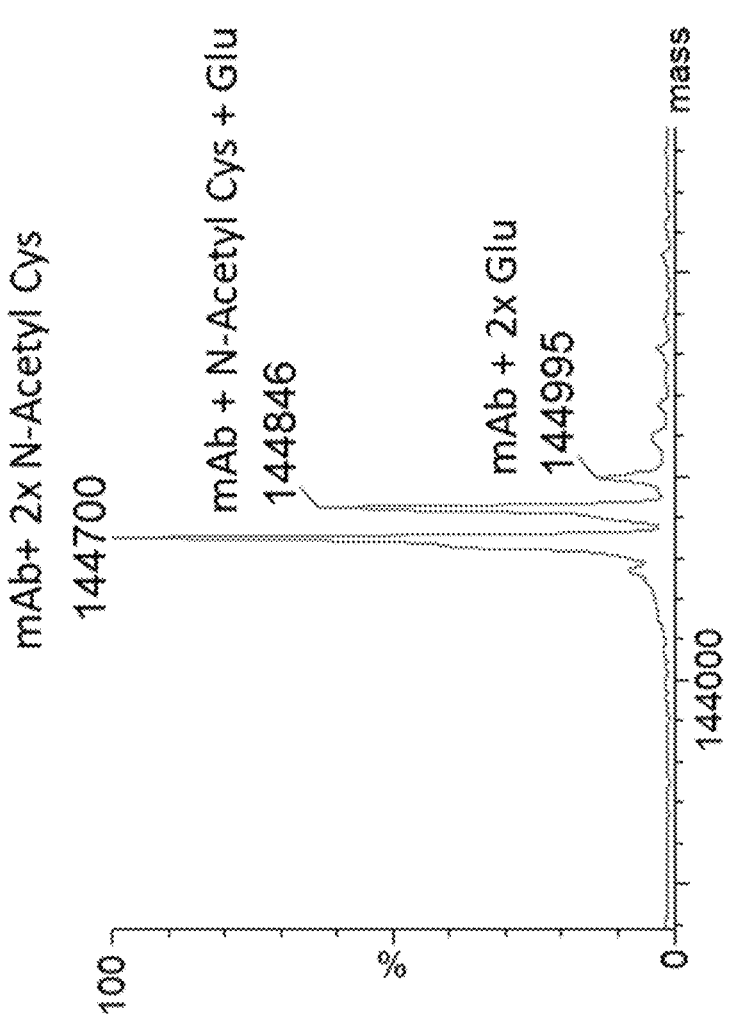
FIGS. 11A & 11B show MS analysis of harvests of antibodies with an engineered cysteine (Cys293) for cysteine capping status.

In this example, the developed denaturing SEC-Intact MS of cell culture harvest has been used for rapid screening of clones for their capping status of Cys293 during cell line development. The first thiomAb candidate studied had a N300A mutation in the Fc region which ablated Fc N-glycosylation. Non-existence of glycans allowed for identification of Cys293 capping by direct intact MS analysis of the harvest without the need for any sample manipulation (FIG. 11A).

Figure 11B:
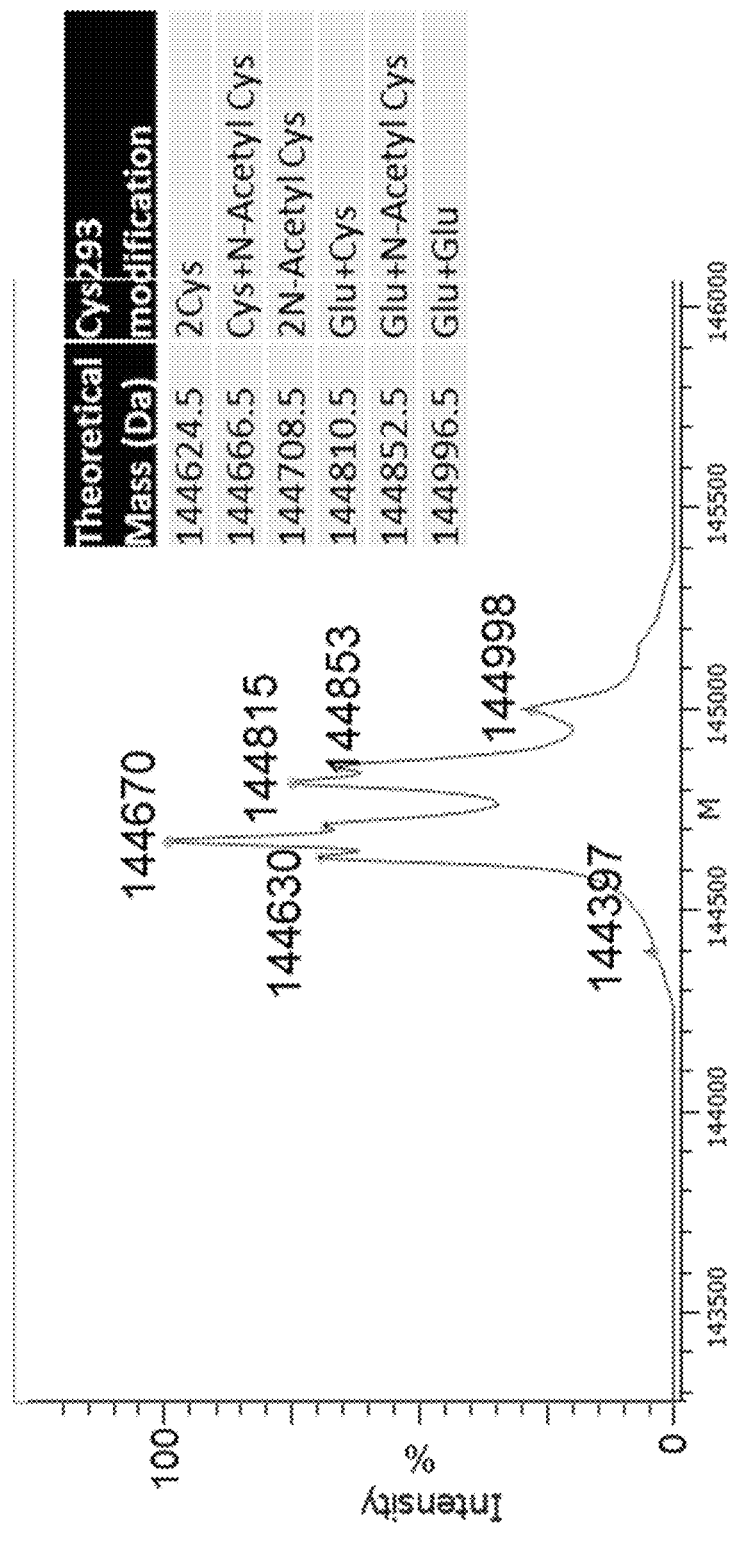

However, the second thiomAb candidate with a typical Fc N-glycosylation profile showed a highly complex pattern in the intact MS data due to the presence of multiple capping species including N-acetyl cysteinylation (+161 Da) that interfered with the mass shift due to addition of hexose monosaccharide residues (+162 Da) to the N-glycans. To circumvent this problem and facilitate data interpretation, clarified harvest from the second candidate was treated with PNGase F to remove N-glycans under native condition. The deglycosylated harvest was subsequently subjected to SEC-Intact MS as before. FIG. 11B shows the deconvoluted intact mass spectrum obtained for the second candidate after deglycosylation, with three types of capping modifications identified: Cysteinylation (Cys) with +119 Da mass shift, N-Acetyl cysteinylation (N-acetyl Cys) with +161 Da mass shift, and Glutathionylation (Glu) with +305 Da mass shift. Screening 22 clones of CHO cells expressing the thiomAb with this method showed 100% capping of the engineered cysteine in all tested clones.

What is claimed is:

1. A method for monitoring production of a multispecific antibody and one or more mispaired species thereof, the method comprising:

separating a cell culture harvest that comprises a multispecific antibody and one or more mispaired species thereof from a cell line that produces the multispecific antibody and the one or more mispaired species thereof, wherein the separation does not comprise chromatographic separation or protein A affinity chromatography;

without prior chromatographic separation or protein A affinity chromatography, separating and detecting, by denaturing size-exclusion ultra-performance liquid chromatography with online mass spectrometry (SE-UPLC-MS), the multispecific antibody and the one or more mispaired species thereof from the cell culture harvest; wherein, prior to SE-UPLC-MS, the cell culture harvest has been clarified by tangential flow filtration (TFF), depth filtration, and/or centrifugation; and wherein the mass spectrometry (MS) is quadrupole time-of-flight (QToF) MS, thereby monitoring production of the multispecific antibody and one or more mispaired species thereof;

wherein the multispecific antibody comprises a first antibody heavy chain, a first antibody light chain, a second antibody heavy chain different from the first antibody heavy chain, and a second antibody light chain different from the first antibody light chain; and wherein the one or more mispaired species comprise two or more polypeptide chains of the multispecific antibody in a species other than that of the multispecific antibody.

2. The method of claim 1, wherein the one or more mispaired species comprises one or more of:

(i) a species that comprises two of the first antibody heavy chains of the multispecific antibody;

(ii) a species that comprises two of the second antibody heavy chains of the multispecific antibody;

(iii) a species that comprises two of the first antibody light chains of the multispecific antibody; and (iv) a species that comprises two of the second antibody light chains of the multispecific antibody.

3. The method of claim 1, wherein detecting the amount of the multispecific antibody and the one or more mispaired species thereof comprises deconvoluting one or more MS spectra obtained by the MS.

4. The method of claim 1, wherein the MS is intact MS.

5. The method of claim 1, wherein SE-UPLC is performed using isocratic elution with a mobile phase.

6. The method of claim 1, wherein detection is accomplished in about 33 minutes or less.

7. The method of claim 1, wherein the MS is capable of resolving a mass difference of about 300 Da between the multispecific antibody and the one or more mispaired species thereof, or between two mispaired species.

8. The method of claim 1, wherein the MS is capable of resolving a mass difference of about 162 Da between the multispecific antibody or mispaired species thereof and one of more glycoforms.

9. A method for monitoring production of an antibody or antibody fragment and one or more weight variant species thereof, the method comprising:

separating a cell culture harvest that comprises an antibody or antibody fragment and one or more weight variant species thereof from a cell line that produces the antibody or antibody fragment and the one or more weight variant species thereof, wherein the separation does not comprise chromatographic separation or protein A affinity chromatography;

without prior chromatographic separation or protein A affinity chromatography, separating and detecting, by denaturing size-exclusion ultra-performance liquid chromatography with online mass spectrometry (SE-UPLC-MS), the antibody or antibody fragment and the one or more weight variant species thereof from the cell culture harvest; wherein, prior to SE-UPLC-MS, the cell culture harvest has been clarified by tangential flow filtration TFF), depth filtration, and/or centrifugation; and wherein the mass spectrometry (MS) is quadrupole time-of-flight (QToF) MS, thereby monitoring production of the antibody or antibody fragment and one or more weight variant species thereof;

wherein the antibody or antibody fragment and one or more weight variant species thereof differ in molecular weight.

10. The method of claim 9, wherein the antibody or antibody fragment and the one or more weight variant species thereof comprise species with a free cysteine that has been cysteinylated, N-acetyl cysteinylated, or glutathionylated.

11. The method of claim 9, wherein the antibody or antibody fragment and the one or more weight variant species thereof comprise species comprising a chemically modified cysteine residue.

12. The method of claim 9, wherein the antibody or antibody fragment and one or more weight variant species thereof differ in molecular weight by at least 119 Da.

13. The method of claim 9, wherein the method is capable of resolving a mass difference among cysteinylated, N-acetyl cysteinylated, and glutathionylated species.

14. The method of claim 9, wherein the antibody or antibody fragment and the one or more weight variant species thereof comprise glycoforms of the antibody or antibody derivative.

15. The method of claim 9, wherein the antibody or antibody fragment and one or more weight variant species thereof differ in molecular weight by at least 162 Da.

16. The method of claim 9, wherein the method is capable of resolving a mass difference between the antibody or antibody fragment and one of more weight variant species thereof that represent glycoforms of the antibody or antibody fragment.

17. A method for monitoring production of a multispecific binding protein and one or more mispaired species thereof, the method comprising:

separating a cell culture harvest that comprises a multispecific binding protein and one or more mispaired species thereof from a cell line that produces the multispecific binding protein and the one or more mispaired species thereof, wherein the separation does not comprise chromatographic separation or protein A affinity chromatography;

without prior chromatographic separation or protein A affinity chromatography, separating and detecting, by denaturing size-exclusion ultra-performance liquid chromatography with online mass spectrometry (SE-UPLC-MS), the multispecific binding protein and the one or more mispaired species thereof from the cell culture harvest; wherein, prior to SE-UPLC-MS, the cell culture harvest has been clarified by tangential flow filtration (TFF), depth filtration, and/or centrifugation; and wherein the mass spectrometry (MS) is quadrupole time-of-flight (QToF) MS, thereby monitoring production of the multispecific binding protein and one or more mispaired species thereof;

wherein the multispecific binding protein comprises four polypeptide chains that form the three antigen binding sites, wherein a first polypeptide chain of the multispecific binding protein comprises a structure represented by the formula:

$$V_{L2}\text{-}L_1\text{-}V_{L1}\text{-}L_2\text{-}C_L \qquad \text{[I]}$$

and a second polypeptide chain of the multispecific binding protein comprises a structure represented by the formula:

$$V_{H1}\text{-}L_3\text{-}V_{H2}\text{-}L_4\text{-}C_{H1}\text{-}\text{hinge}\text{-}C_{H2}\text{-}C_{H3} \qquad \text{[II]}$$

and a third polypeptide chain of the multispecific binding protein comprises a structure represented by the formula:

$$V_{H3}\text{-}C_{H1}\text{-}\text{hinge}\text{-}C_{H2}\text{-}C_{H3} \qquad \text{[III]}$$

and a fourth polypeptide chain of the multispecific binding protein comprises a structure represented by the formula:

$$V_{L3}\text{-}C_L \qquad \text{[IV]}$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair, wherein $V_{H1}$ and $V_{L1}$ form a first antigen binding site, wherein $V_{H2}$ and $V_{L2}$ form a second antigen binding site, and wherein $V_{H3}$ and $V_{L3}$ form a third antigen binding site; and wherein the one or more mispaired species comprise two or more polypeptide chains of the multispecific binding protein in a species other than that of the multispecific binding protein.

18. The method of claim 17, wherein the one or more mispaired species comprises one or more of:

(i) a species that comprises two of the first polypeptide chains of the multispecific binding protein;

(ii) a species that comprises two of the second polypeptide chains of the multispecific binding protein;

(iii) a species that comprises two of the third polypeptide chains of the multispecific binding protein; and (iv) a species that comprises two of the fourth polypeptide chains of the multispecific binding protein.

\* \* \* \* \*